United States Patent
Rezvani et al.

(10) Patent No.: US 11,154,572 B2
(45) Date of Patent: Oct. 26, 2021

(54) METHODS OF TREATMENT WITH NATURAL KILLER CELLS MATCHED FOR KILLER IMMUNOGLOBULIN RECEPTOR TYPE

(71) Applicant: Board of Regents, The University of Texas System, Austin, TX (US)

(72) Inventors: Katy Rezvani, Houston, TX (US); Elizabeth Shpall, Houston, TX (US); Enli Liu, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 247 days.

(21) Appl. No.: 15/579,330

(22) PCT Filed: Jun. 6, 2016

(86) PCT No.: PCT/US2016/036024
§ 371 (c)(1),
(2) Date: Dec. 4, 2017

(87) PCT Pub. No.: WO2016/197108
PCT Pub. Date: Dec. 8, 2016

(65) Prior Publication Data
US 2018/0353544 A1 Dec. 13, 2018

Related U.S. Application Data

(60) Provisional application No. 62/171,520, filed on Jun. 5, 2015.

(51) Int. Cl.
| | |
|---|---|
| *A61K 35/17* | (2015.01) |
| *A61P 35/02* | (2006.01) |
| *A61K 31/4525* | (2006.01) |
| *A61K 39/00* | (2006.01) |
| *C07K 14/725* | (2006.01) |
| *C07K 16/28* | (2006.01) |
| *C07K 14/705* | (2006.01) |
| *C07K 14/47* | (2006.01) |
| *A61P 37/06* | (2006.01) |
| *A61K 31/675* | (2006.01) |

(52) U.S. Cl.
CPC ............ *A61K 35/17* (2013.01); *A61P 35/02* (2018.01); *A61P 37/06* (2018.01); *C07K 14/4748* (2013.01); *C07K 14/7051* (2013.01); *C07K 14/70521* (2013.01); *C07K 16/28* (2013.01); *A61K 31/4525* (2013.01); *A61K 31/675* (2013.01); *A61K 2300/00* (2013.01); *C07K 2319/02* (2013.01); *C07K 2319/03* (2013.01)

(58) Field of Classification Search
None
See application file for complete search history.

(56) References Cited

U.S. PATENT DOCUMENTS

2014/0328812 A1 11/2014 Campana et al.

FOREIGN PATENT DOCUMENTS

| WO | WO 2014-037422 | 3/2014 |
| WO | WO 2015-154012 | 10/2015 |

OTHER PUBLICATIONS

Edwards et al (JMB, 2003, 334: 103-118) (Year: 2003).*
Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Torres and Casadevall (Trend. Immunol., 2008, 29(2): 91-97) (Year: 2008).*
Vitale et al (Eur. J. Immunol. 2014, 44: 1582-1592) (Year: 2014).*
Holmes et al (J. Immunol. 2011, 186: 1538-1545) (Year: 2011).*
Dahlberg et al (Front. Immunol. 2015, 6: pp. 1-19) (Year: 2015).*
Olsen, M (Overview of Hematologic Malignancies. Hematologic Malignancies in Adults, Pittsburgh, PA, Oncology Nursing Society, 2013: 1-17) (Year: 2013).*
Boissel et al., "Comparison of mRNA and lentiviral based transfection of natural killer cells with chimeric antigen receptors recognizing lymphoid antigens," *Leuk. Lymphoma*, 53(5):958-965, 2012, abstract only.
Cany et al., "Natural killer cells generated from cord blood hematopoietic progenitor cells efficiently target bone marrow-residing human leukemia cells in NOD/SCID/IL2Rg(null) mice," *PLoS One*, 8(6):e64384, 2013, abstract only.
Cooley et al., "Donor killer cell Ig-like receptor B haplotypes, recipient HLA-C1, and HLA-C mismatch enhance the clinical benefit of unrelated transplantation for acute myelogenous leukemia," *J. Immunol.*, 192(10):4592-4600, 2014, abstract only.
Hoyos et al., "Engineering CD19-specific T lymphocytes with interleukin-15 and a suicide gene to enhance their anti-lymphoma/leukemia effects and safety," Leukemia, 24(6):1160-1170, 2010.
International Preliminary Report on Patentability issued in corresponding PCT Application No. PCT/US16/036024, dated Dec. 5, 2017.
International Search Report and Written Opinion issued in corresponding PCT Application No. PCT/US16/036024, dated Sep. 8, 2016.

(Continued)

*Primary Examiner* — G. R. Ewoldt
*Assistant Examiner* — Marianne DiBrino
(74) *Attorney, Agent, or Firm* — Norton Rose Fulbright US LLP

(57) ABSTRACT

The present invention concerns methods of treating a disease such as leukemia in a subject by administering natural killer (NK) cells. In particular aspects, HLA-C1-licensed KIR2DL2/3 and KIR2DS2 NK cells are administered to a subject with an HLA-C genotype either homozygous or heterozygous for the C1 allele, or HLA-C2 licensed cells are administered to a subject with an HLA-C genotype homozygous for the C2 allele. In further aspects, the NK cells are genetically modified to express a chimeric antigen receptor and interleukin 15.

18 Claims, 41 Drawing Sheets

(56) References Cited

OTHER PUBLICATIONS

Kim et al., "Licensing of natural killer cells by host major histocompatibility complex class I molecules," Nature, 436(4):709-713, 2005.
Marin et al., "KIR2DS1 genotype predicts for complete cytogenetic response and survival in newly diagnosed chronic myeloid leukemia patients treated with imatinib," *Leukemia*, 26:296-302, 2012.
Schpall "The Future of Cord Blood Cellular Therapy," Powerpoint Presentation at 2014 Annual Meeting, International Society for Cellular Therapy, Apr. 2014.
Shah et al., "Antigen Presenting Cell-Mediated Expansion of Human Umbilical Cord Blood Yields Log-Scale Expansion of Natural Killer Cells with Anti-Myeloma Activity," *PLoS One*, 8(10):e76781, 2013.
Singh et al., "Redirecting Specificity of T-Cell Populations For CD19 Using the Sleeping Beauty System," *Cancer Research*, 68:2961-2971, 2008.
Singh et al., "Reprogramming CD19-specific T cells with IL-21 signaling can improve adoptive immunotherapy of B-lineage malignancies," *Cancer Research*, 71:3516-3527, 2011.
Spanholtz et al., "Clinical-Grade Generation of Active NK Cells from Cord Blood Hematopoietic Progenitor Cells for Immunotherapy Using a Closed-System Culture Process," *PLoS* One, 6(6):e20740, 2011.
Wu et al., "Lenalidomide Enhances Natural Killer Cell and Monocyte-Mediated Antibody-Dependent Cellular Cytotoxicity of Rituximab-Treated CD20+ Tumor Cells," *Clin. Cancer Res.*, 14(14):4650-4657, 2008.
Greta Maria Paola Giordano Attianese, et al; "In vitro and in vivo model of a novel immunotherapy approach for chronic lymphocytic leukemia by anti-CD23 chemeric antigen receptor"; Blood. May 5, 2011; 117(18) 4736-4745.
Bonnefoy, et al; "Antibodies against CD23, deriavatives thereof and therapeutic utilization of the same"; ncbi.nih.gov; Genbank BD232452. 1; Nov. 4, 2005.
Bonnefoy, et al; "Antibodies against CD23, derivatives thereof and therapeutic utilization of the same"; ncbi.nih.gov; GenBank BD232451. 1; Nov. 4, 2005.
Olivier Cochet, et al; "Intracellular Expression of an Antibody Fragment-Neutralizing p21 Ras Promotes Tumor Regression"; Cancer Research 58. 1170-1176; Mar. 15, 1998.
Jose A. Figueroa, et al; "Chimeric Antigen Receptor Engineering: A Right Step in the Evolution of Adoptive Cellular Immunotherapy"; International Reviews of Immunology, ISSN: 0883-0185 / 1563-5244; Apr. 22, 2015.
Saar Gill, et al; "Chimeric Antigen Receptor T Cell Therapy: 25 Years in the Making"; Blood Reviews; Elsevier.com; 2016; 157-167.
Mahesh Jonnalagadda, et al; Chimeric Antigen Receptors With Mutated IgG4 Fc Spacer Avoid Fc Receptor Binding and Improve T Cell Persistence and Antitumor Efficacy; Molecular Therapy, vol. 23, No. 4; 757-768; Apr. 2015.
A. Klimka, et al; "An anti-CD30 single-chain Fv Selected by Phage Display and Fused to Pseudomonas Exotoxin A (Ki-4(scFv)-ETA') is a Potent Immunotoxin Against a Hodgkin-Derived Cell Line"; British Journal of Cancer 80(8); 1214-1222; 1999.
Shannon L. Maude, et al; "CD19 Targeted Chimeric Antigen Receptor T-Cell Therapy for Acute Lymphoblastic Leukemia"; Blood 125(26); 4017-4023; Jun. 25, 2015.
Ian C. Nicholson, et al; "Construction and Characterisation of a Functional DC19 Specific Single Chain Fv Fragment for Immunotherapy of B Lineage Leukaemia and Lymphoma"; Molecular Immunology, vol. 34. No. 16-17; pp. 1157-1165; 1997.
Sara Orgad, et al; "Single Chain Antibody Against the Common Epitope of Mutant p53 restores wild-type activity to mutant p53 protein"; Elsevier, FEBS Letters 579 (2005) 5609-5615.
LM Pericieous, et al; "Characterisation and Internalisation of Recombinant Humanised HMFG-I antibodies against MUCI"; British Journal of Cancer (2005) 93, 1257-1266.
Daming Shan, et al: "Characterization of scFv-Ig Constructs Generated from the Anti-CD20 mAb 1F5 Using Linker Peptides of Varying Lengths"; J. Immunol 1999; 162: 6859-6595.
Saar Gill, et al; "Going Viral: Chimeric Antigen Receptor T-Cell Therapy for Hematological Malignancies"; Immunological Reviews: 2015; vol. 263: 68-89.
Sarah Tettamanti, et al; "Targeting of Acute Myeloid Leukaemia by Cytokine-Induced Killer Cells Redirected with a Novel CD123-Specific Chimeric Antigen Receptor"; British Journal of Haematology, 2013, 161, 389-401.

\* cited by examiner

METHODS OF TREATMENT WITH NATURAL KILLER CELLS MATCHED FOR KILLER IMMUNOGLOBULIN RECEPTOR TYPE

This application is a national phase application under 35 U.S.C. § 371 of International Application No. PCT/US2016/036024, filed Jun. 6, 2016, which claims the benefit of U.S. Provisional Patent Application No. 62/171,520, filed Jun. 5, 2015, each of which is incorporated herein by reference, in its entirety.

BACKGROUND OF THE INVENTION

1. Field of the Invention

The present invention relates generally to the fields of medicine, immunology, cell biology, and molecular biology. In certain aspects, the field of the invention concerns immunotherapy. More particularly, embodiments described herein concern methods of treatment with natural killer cells engineered to express chimeric antigen receptors (CARs).

2. Description of Related Art

Understanding the role of the immune system in the control of cancer and the mechanisms mediating immune evasion remains one of the most challenging questions in tumor immunology. Malignancies, such as acute lymphoblastic leukemia (ALL), chronic lymphocytic leukemia (CLL), acute myeloid leukemia (AML), myelodysplastic syndrome (mDS), chronic myelogenous leukemia (CML), multiple myeloma, Hodgkin's lymphoma, and non-Hodgkin lymphoma, are often incurable with chemotherapy. Thus, allogeneic hematopoietic stem cell transplantation (HSCT) is the sole curative treatment for many hematologic cancers. However, only 30%-40% of patients who require an allograft will have a human leukocyte antigen (HLA)-identical sibling donor (Khouri et al., 2004), and many patients, particularly those with minority racial/ethnic backgrounds, will lack an identified, suitably matched unrelated volunteer donor.

For patients lacking HLA-matched donors, cord blood (CB) is being used increasingly as a stem cell source for allotransplant in high-risk hematologic malignancies The genetically diverse CB units and the less stringent requirements for HLA matching made possible by umbilical cord blood have greatly extended access to stem cell transplantation (Ruggeri et al., 2002). However, CB transplantation (CBT) has a number of disadvantages, including delayed hematopoietic recovery that imposes higher risks of life-threatening infections and disease progression or relapse. Thus, strategies that could eliminate minimal residual disease after CBT, before the recipient regains full immune competence, would be instrumental in widening the appeal of CBT as a clinically efficacious procedure. The use of donor lymphocyte infusions (DLI), which can augment antileukemic and antiviral immunity after HSCT, has the potential to overcome many of these limitations. However, this approach is frequently associated with graft-versus-host disease (GVHD), and is not feasible after CBT due to the small size of the cryopreserved units and anonymity of the donor.

As the first lymphocyte subset to reconstitute the peripheral blood after stem cell transplantation, NK cells play an important role in mediating the graft-versus-leukemia (GVL) effect and therefore offer attractive options for improving the outcome of CBT. In the allogeneic transplant setting, the ability of an NK cell to recognize and kill transformed cells is governed by a complex regulatory system, based on interactions between killer immunoglobulin receptors (KIR) and their ligands. Briefly, HLA class I molecules can serve as ligands for both inhibitory and activating KIRs, leading to enormous variability in KIR-HLA ligand repertoire of NK cells (Rocha et al., 2004). Thus, there is an unmet need to exploit NK cell alloreactivity in CBT by identifying specific patterns of interaction between MR and their HLA ligands, and relating the results to transplantation outcome.

SUMMARY OF THE INVENTION

The present disclosure provides methods for the treatment of a disease or disorder by the administration of a therapeutically effective amount of NK cells that express a specific killer immunoglobulin-like receptor to a subject with a particular HLA-C genotype. In one embodiment, NK cells expressing HLA-C1-licencsed KIR2DL2/3 and KIR2DS2 are administered to a subject with an HLA-C genotype either homozygous or heterozygous for the C1 allele. In other embodiments, NK cells expressing HLA-C2-licensed KIR2DL1 and KIR2DS1 are administered to a subject with an HLA-C genotype that is homozygous for the C2 allele. In certain embodiments, the NK cells are genetically engineered to express interleukin-15 (IL-15) and/or a chimeric antigen receptor (CAR) specific for a particular tumor antigen (e.g., CD19).

In one embodiment, a method is provided of treating a disease or disorder in a subject in need thereof comprising administering to the subject a therapeutically effective amount of natural killer (NK) cells, wherein (a) the subject has been determined to have an HLA-C genotype either homozygous or heterozygous for the C1 allele and the NK cells express HLA-C1-licensed KIR2DL2/3 and KIR2DS2; or (b) the subject has been determined to have an HLA-C genotype that is homozygous for the C2 allele and the NK cells express HLA-C2-licensed KIR2DL1 and KIR2DS1.

In certain aspects of the embodiments, the HLA-C genotype of a patient is determined. For example, a patient can be determined to have an HLA-C genotype either homozygous or heterozygous for the C1 allele. In some aspects, the patient is determined to have an HLA-C genotype either homozygous or heterozygous for the C1 allele and the NK cells express HLA-C1-licensed KIR2DL2/3 and KIR2DS2. In other aspects, the patient is determined to have an HLA-C genotype that is homozygous for the C2 allele and the NK cells express HLA-C2-licensed KIR2DL1 and KIR2DS1.

In further aspects of the embodiments, the NK cells are derived from umbilical CB or peripheral blood.

In certain aspects, the NK cells are genetically modified. In particular aspects, the NK cells are genetically modified to express IL-15. In further aspects, the NK cells are genetically modified to express a recombinant CAR. In particular aspects, the CAR can comprise an intracellular signaling domain, a transmembrane domain, and/or an extracellular domain. In certain aspects, DNA encoding the CAR is integrated into the genome of the cell.

In some aspects, the extracellular domain of the CAR comprises an antigen binding region. In certain aspects, the antigen binding region may be a F(ab')2, Fab', Fab, Fv, or scFv. In a further aspect, the antigen binding region binds a tumor associated antigen. For example, the tumor associated antigen may be CD19, CD20, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, EGFRvIII, or VEGFR2.

In certain aspects, the intracellular signaling domain is a T-lymphocyte activation domain. In some aspects, the intracellular signaling domain may comprise CD3ξ, CD28, OX40/CD134, 4-1BB/CD137, FcεRIγ, ICOS/CD278, ILRB/CD122, IL-2RG/CD132, DAP molecules, CD70, cytokine receptor, CD40, or a combination thereof. In certain aspects, the transmembrane domain comprises CD28 transmembrane domain, IgG4Fc hinge, Fc regions, CD4 transmembrane domain, the CD3ξ transmembrane domain, cysteine mutated human CD3ξ domain, CD16 transmembrane domain, CD8 transmembrane domain, or erythropoietin receptor transmembrane domain.

In further aspects, the NK cells are genetically modified to express an inducible suicide gene. In particular aspects, the suicide gene may be caspase 9. In certain aspects, the embodiments provide a method that further comprises administering to the subject a small molecule to induce apoptosis of the NK cells. For example, the small molecule may be AP20187.

In further aspects of the embodiments, methods are provided for administering a second therapeutic agent. In some aspects, the second therapeutic agent may comprise T cells, an immunomodulatory agent, a monoclonal antibody, or a chemotherapeutic agent. In some aspects, the immunomodulatory agent is lenalidomide. In other aspects, the monoclonal antibody is rituximab, ofatumumab, or lumiliximab. In some aspects, the chemotherapeutic agent is fludarabine or cyclophosphamide.

In certain aspects, the disease or disorder is a cancer, an immunodeficiency disease, an autoimmune disease, a B cell malignancy, or an infection. In some aspects, the cancer is a leukemia. In particular aspects, the leukemia may be an acute lymphoblastic leukemia (ALL), chronic lymphocytic leukemia (CLL), acute myelogenous leukemia (AML), or a chronic myelogenous leukemia (CML). In some aspects, the subject is a human. In certain specific aspects, the disease or disorder is a cancer and the patient is in remission.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In FIG. 3A, at the 4 month time point, the top line represents "HLA-C2/C2", the middle line represents "HLA-C1/C2", and the bottom line represents "HLA-C1/C1". In FIG. 3B, at the 4 month time point, the top line represents "HLA-C1/C1", the middle line represents "HLA-C1/C2", and the bottom line represents "HLA-C2/C2".

In FIG. 4B, within each pair of boxes, the left (lower) box represents "Single KIR2DL1/S2 expressing NK cells" and the right (upper) box represents "Single KIR2DL2/L3/S2 expressing NK cells".

In FIG. 5A, at the 6 month time point, the top line represents "HLA-C1-neg", the middle line represents "KIR2DS2-neg", and the bottom line represents "HLA-C1-KIR2DL2/L3/S2-pos". In FIG. 5B, at the 8 month time point, the top line represents "HLA-C1/x-KIR2DL2/L3/S2-pos", the middle line represents "HLA-C1-neg", and the bottom line represents "KIR2DS2-neg".

In FIG. 6A, the top line represents "HLA-C2-neg or KIR2DS2-neg" and the bottom line represents "HLA-C2-KIR2DL1/S1-pos". In FIG. 6B, at the 4 month time point, the top line represents "HLA-C2-KIR2DL1/S1-pos" and the bottom line represents "HLA-C2-neg or KIR2DS2-neg".

In FIGS. 7A, 7B, 7E and 7F, the top line represents "Recipient HLA-C2 homozygous", the middle line represents "Recipient HLA-C1/x; graft negative for HLA-C1 or KIR2DS2", and the bottom line represents "Recipient HLA-C1/x; graft HLA-C1-KIR2DL2/L3/S2+". In FIGS. 7C, 7D, 7G and 7H, the top line represents "Recipient HLA-C1/x; graft HLA-C1-KIR2DL2/L3/S2+", the middle line represents "Recipient HLA-C1/x; graft negative for HLA-C1 or KIR2DS2", and the bottom line represents "Recipient HLA-C2 homozygous".

In FIG. 9A, the top line represents Graft negative for HLA-C1 or KIR2DS2 and the bottom line represents Graft HLA-C1-KIR2DL2/L3/S2+. In FIG. 9B, at the 2 month time point, the top line represents Graft HLA-C1-KIR2DL2/L3/S2+ and bottom line represents Graft negative for HLA-C1 or KIR2DS2. In FIG. 9C, the top line represents Graft HLA-C1-KIR2DL2/L3/S2+ and bottom line represents Graft negative for HLA-C1 or KIR2DS2. In FIG. 9D, at the 2 month time point, the top line represents Graft HLA-C1-KIR2DL2/L3/S2+ and bottom line represents Graft negative for HLA-C1 or KIR2DS2.

DESCRIPTION OF ILLUSTRATIVE EMBODIMENTS

Figure 1A:
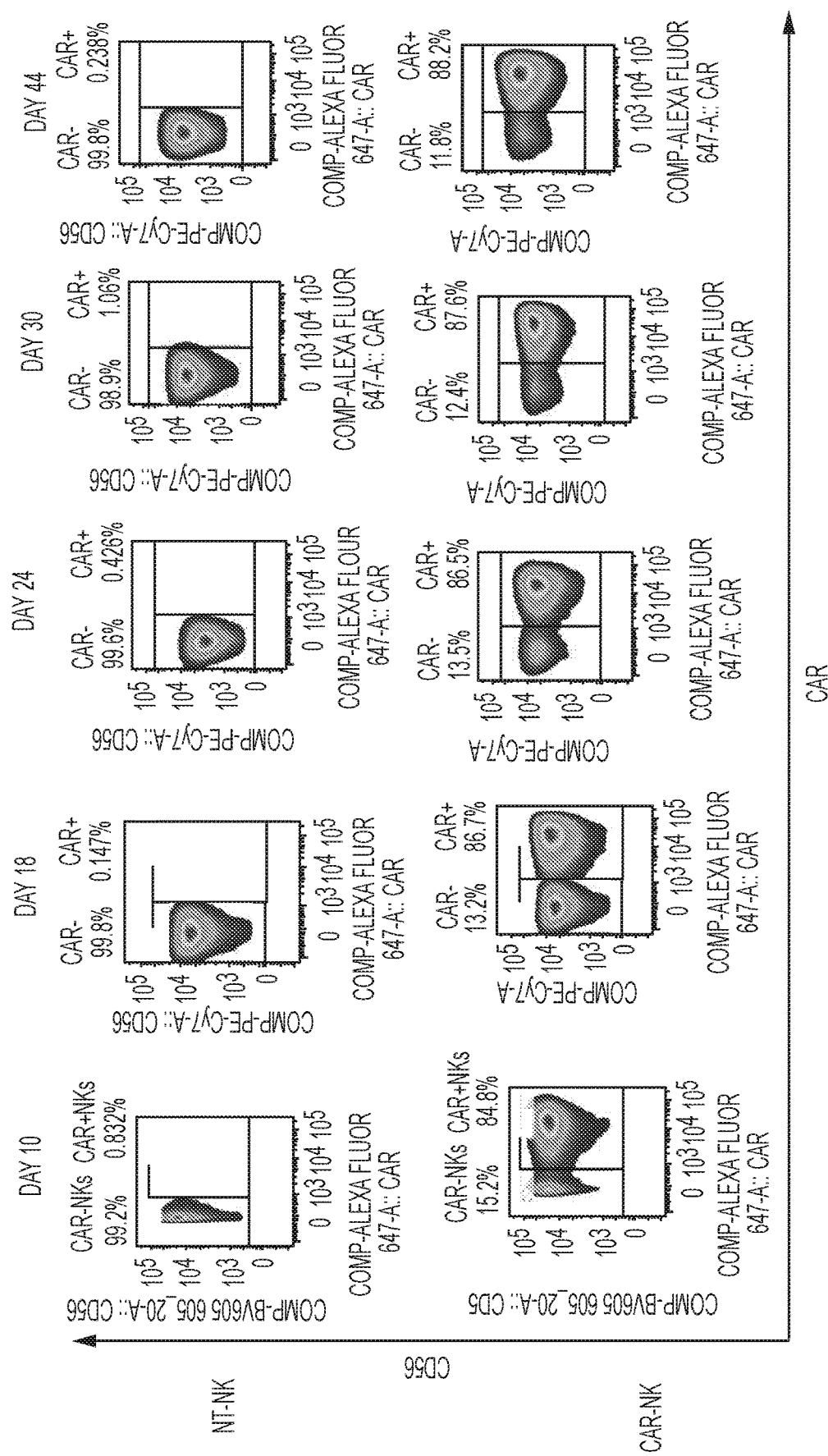
FIGS. 1A-1I: (A) CB NK cells were stably transduced with SFG.iCASP9.2A.CAR.CD19-28z.2A.OhIL-12. Cell analysis for CD56 and CAR are shown from Day 10 to Day 44. (B) Histograms show NK receptor expression on ex vivo-expanded cord blood versus peripheral blood NK cells. NK receptors include KIR2DL2/DL3, KIR2DL1, NGK2A, NKP30, NKP44, and NKP46. (C) aAPC-expanded NK cells maintain an Eomes$^{hi}$ and T-bet$^{hi}$ phenotype. (D) Human CAR-transduced cord blood derived-NK cells proliferate more efficiently than non-transduced CB-derived NK cells following expansion with clones 9.mbIL-21 and IL-2 200 U/mL. (E) Human CAR-transduced CB-NK cells do not display markers of exhaustion, such as downregulation of eomesodermin and T-bet, or up-regulation of KLRG1. (F) CAR-transduced CB-NK cells show increased IFN-γ cytokine production against K562 or CD19$^+$ (Raji) cells. (G) NK cells co-expressing CAR.19-IL-15-iCasp9 form functional synapses with CD19$^+$ CLL cells. Cells are stained for Perforin, Phalloidin, and CAR and imaged by confocal microscopy. (H) CAR.19-IL-15-iCasp9 transduced CB-NK cells are more efficient at killing primary CD19$^+$ tumor cells. Percent lysis of tumor cells is shown at varying effector: target ratios of K562, Raji, and CLL cells. (I) The activity of cord blood-derived NK cells against primary CLL cells is enhanced with lenalidomide (Revlimid).

Leukemia cells evade NK-mediated immune surveillance by actively modulating NK cell function and phenotype, through the release of immunomodulatory molecules such as IL-10 and TGF-β1. The present disclosure concerns methods of enhancement of NK cell function against diseases and disorders, such as leukemia. Methods provided herein include strategies to expand NK cells based on their co-culture with genetically-modified leukemic cells that express cytokines and co-stimulatory molecules. Particularly, the NK cells can be derived from fresh or frozen CB. The present methods ensure reliable expansion and activation of NK cells and can be implemented in a GMP-grade large-scale setting.

In exemplary methods to redirect NK cell specificity and enhance their in vivo persistence, NK cells were transduced with CARs directed against tumor antigens, such as CD19, which is a molecule expressed on lymphoid malignant cells. Particularly, the CAR comprises CD28 and CD3ζ intracellular signaling domains. The cells may further comprise interleukin (IL-15) to enhance the in vivo persistence and survival of NK cells following their administration to a subject. In certain aspects, the administration of the NK cells is by adoptive transfer.

Although NK cell alloreactivity is known to be regulated by the balance of inhibitory and activating NK cell receptors, such as killer-cell immunoglobulin-like receptor (KIR), the combination of these factors with the best therapeutic effect is unknown. To address this issue, the present study analyzed donor NK cell MR genotypes and clinical data for a large cohort of cord blood transplant patients. HLA ligands and genotypes that are most closely associated with outcome in patients undergoing cord blood transplantation (CBT) for hematologic cancers were studied. It was found that a patient with HLA-C1/C1 or C1/C2 genotype, receiving NK cells licensed for inhibitory KIR2DL2/DL3 and activating KIR2DS2 genotypes, confers a superior outcome compared to any other MR-HLA ligand combination. Thus, in certain aspects of the present disclosure, subjects with an HLA-C1/C1 or HLA-C1/C2 genotype are given NK cells licensed for KIR2DL2/3 and expressing KIR2DS2, and patients with an HLA-C2/C2 genotype are given NK cells licensed for KIR2DL1 and expressing KIR2DS1.

Thus, aspects of the present disclosure provide methods for the treatment of a disease, such as cancer, by the administration of NK cells licensed for a particular MR genotype. In some aspects, NK cells are engineered with a viral vector to redirect their specificity to recognize tumor antigens. In certain methods, the construct includes cytokines to support the growth and survival of the genetically modified NK cells following adoptive transfer and/or a suicide gene should untoward toxicity occur in the recipient, allowing immediate destruction of the NK cells.

I. DEFINITIONS

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of cord blood-derived NK cells for the purpose of treating cancer.

A "subject" refers to either a human or non-human, such as primates, mammals, and vertebrates. In particular embodiments, the subject is a human.

The term "therapeutic benefit" or "therapeutically effective" as used herein refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a NK cell, thereby allowing a large number of specific NK cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In particular embodiments, one can target malignant B cells by redirecting the specificity of NK cells by using a CAR specific for the B-lineage molecule, CD19. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the NK cells upon addition of a pro-drug, homing receptors, chemokines, chemokine receptors, cytokines, and cytokine receptors.

As used herein, the term "antigen" is a molecule capable of being bound by an antibody or T-cell receptor. An antigen may generally be used to induce a humoral immune response and/or a cellular immune response leading to the production of B and/or T lymphocytes.

The terms "tumor-associated antigen" and "cancer cell antigen" are used interchangeably herein. In each case, the terms refer to proteins, glycoproteins or carbohydrates that are specifically or preferentially expressed by cancer cells.

As used herein, "KIR" refers to a killer immunoglobulin-like receptor that serves as a regulator of NK cell function.

II. NATURAL KILLER CELLS

Natural killer (NK) cells are a subpopulation of lymphocytes that have spontaneous cytotoxicity against a variety of tumor cells, virus-infected cells, and some normal cells in the bone marrow and thymus. NK cells are critical effectors of the early innate immune response toward transformed and virus-infected cells. NK cells constitute about 10% of the lymphocytes in human peripheral blood. When lymphocytes are cultured in the presence of interleukin 2 (IL-2), strong cytotoxic reactivity develops. NK cells are effector cells known as large granular lymphocytes because of their larger size and the presence of characteristic azurophilic granules in their cytoplasm (Herberman, 1986). NK cells differentiate and mature in the bone marrow, lymph nodes, spleen, tonsils, and thymus. NK cells can be detected by specific surface markers, such as CD16, CD56, and CD8 in humans. NK cells do not express T-cell antigen receptors, the pan T marker CD3, or surface immunoglobulin B cell receptors.

Stimulation of NK cells is achieved through a cross-talk of signals derived from cell surface activating and inhibitory receptors. The activation status of NK cells is regulated by a balance of intracellular signals received from an array of germ-line-encoded activating and inhibitory receptors (Campbell, 2006). When NK cells encounter an abnormal cell (e.g., tumor or virus-infected cell) and activating signals predominate, the NK cells can rapidly induce apoptosis of the target cell through directed secretion of cytolytic granules containing perforin and granzymes or engagement of death domain-containing receptors. Activated NK cells can also secrete type I cytokines, such as interferon-γ, tumor necrosis factor-α and granulocyte-macrophage colony-stimulating factor (GM-CSF), which activate both innate and adaptive immune cells as well as other cytokines and chemokines (Wu et al., 2003). Production of these soluble factors by NK cells in early innate immune responses significantly influences the recruitment and function of other hematopoietic cells. Also, through physical contacts and production of cytokines, NK cells are central players in a regulatory crosstalk network with dendritic cells and neutrophils to promote or restrain immune responses.

NK cell responses are mediated by two major effector functions: direct cytolysis of target cells and production of chemokines and cytokines. Through the latter mechanism (e.g., interferon-γ), NK cells participate in the shaping of the adaptive T cell response, possibly by a direct interaction between naïve T cells and NK cells migrating to secondary lymphoid compartments from inflamed peripheral tissues and by an indirect effect on dendritic cells (DC).

Major histocompatibility complex (MHC) class I (HLA-A, -B, and -C) molecules are expressed on the surface of nearly every normal nucleated cell in the human body, are encoded by the most polymorphic genes in humans, and define immune "self." The function of MHC class I molecules is to display fragments of non-self proteins to cytotoxic T cells. Tolerance of NK cells toward normal cells is achieved through NK cell expression of MHC-I-binding inhibitory receptors, which include KIR, Ly49, and CD85j (also known as ILT2 or LIR1). Activating receptors of NK cells include Ly49, natural cytotoxicity receptors (NCR), CD94/NKG2, and CD16. NK cells preferentially attack abnormal cells that have down-regulated surface MHC-I molecules, termed "missing self recognition" (Ljunggren et al., 1990). For example, when the inhibitory receptors encounter MHC class I on normal cells, they recruit SHP-1 and SHP-2 protein tyrosine phosphates at immunoreceptor tyrosine-based inhibitory motifs (ITIMs) to dominantly arrest tyrosine kinase-based-activation signals. However, when a mature NK cell encounters an abnormal cell lacking MHC class I, inhibitory receptors are not engaged and unsuppressed activating signals trigger targeted attack. Thus, the combinatorial engagement of activating and inhibitory cell-surface receptors determines whether NK cells will or will not kill target cells and/or produce cytokines during their effector phase of activation.

The expression of self MHC-I-reactive killer cell immunoglobulin-like receptors (KIRs) is critical for the maturation of functionally responsive NK cells, through a process referred to as "education," "licensing," or "arming" (Anfossi et al., 2006). This process refers to the changes in NK cells responsiveness induced by the environment, especially as a result of variations in the expression of MHC class I molecules or activating ligands.

KIRs are a family of highly polymorphic activating and inhibitory receptors that serve as key regulators of human NK cell development, tolerance, and activation. They are transmembrane glycoproteins expressed on NK cells and a subset of T cells with conserved extracellular, transmembrane, and cytoplasmic domains (Vilches et al., 2002). Distinct structural domains in different KIRs determine function by providing docking sites for ligands. The MR family is encoded by 14 highly polymorphic genes including 2DL1 to 2DL5, 3DL1 to 3DL3, 2DS1 to 2DS5, and 3DS1. Nomenclature of MRs is based upon the number of C2-type immunoglobulin-like domains in the extracellular region (i.e., 2D for two domains, 3D for three domains) and by the length of the cytoplasmic domain (i.e., L for long-tailed receptors and S for short-tailed receptors) (Marsh et al., 2003). All inhibitory KIRs have long cytoplasmic domains with immunoreceptor-based inhibitory motifs, which recruit protein tyrosine phosphatases. KIRs with short cytoplasmic domains associated with a transmembrane signaling adaptor protein, DAP12. There is extensive natural polymorphism associated with MRs and their ligands, MHC class I molecules (Campbell et al., 2011).

III. EXPANSION AND GENETIC ENGINEERING OF NK CELLS

In certain embodiments, NK cells are derived from human peripheral blood mononuclear cells (PBMC), unstimulated leukapheresis products (PBSC), human embryonic stem cells (hESCs), induced pluripotent stem cells (iPSCs), bone marrow, or umbilical cord blood by methods well known in the art. Particularly, umbilical CB is used to derive NK cells. In certain aspects, the NK cells are isolated and expanded by the previously described method of ex vivo expansion of NK cells (Spanholtz et al., 2011; Shah et al., 2013). In this method, CB mononuclear cells are isolated by ficoll density gradient centrifugation and cultured in a bioreactor with IL-2 and artificial antigen presenting cells (aAPCs). After 7 days, the cell culture is depleted of any cells expressing CD3 and re-cultured for an additional 7 days. The cells are again CD3-depleted and characterized to determine the percentage of CD56$^+$/CD3$^-$ cells or NK cells. In other methods, umbilical CB is used to derive NK cells by the isolation of CD34$^+$ cells and differentiation into CD56$^+$/CD3$^-$ cells by culturing in medium contain SCF, IL-7, IL-15, and IL-2.

A. Chimeric Antigen Receptors

In certain embodiments, the derived NK cells are genetically modified to express a chimeric antigen receptor. In some embodiments, the chimeric antigen receptor comprises: a) an intracellular signaling domain, b) a transmembrane domain, and c) an extracellular domain comprising an antigen binding region.

A CAR recognizes cell-surface tumor-associated antigen independent of human leukocyte antigen (HLA) and employs one or more signaling molecules to activate genetically modified NK cells for killing, proliferation, and cytokine production (Jena et al., 2010). In certain embodiments, the platform technologies disclosed herein to genetically modify NK cells comprise (i) non-viral gene transfer using an electroporation device (e.g., a nucleofector), (ii) CARs that signal through endodomains (e.g., CD28/CD3-ζ, CD137/CD3-ζ, or other combinations), (iii) CARs with variable lengths of extracellular domains connecting the antigen-recognition domain to the cell surface, and, in some cases, (iv) artificial antigen presenting cells (aAPC) derived from K562 to be able to robustly and numerically expand CAR+ NK cells (Singh et al., 2008; Singh et al., 2011).

Embodiments of the present disclosure concern the use of nucleic acids, including nucleic acids encoding an antigen-specific chimeric antigen receptor (CAR) polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be human genes used to enhance cellular immunotherapy for human patients. In a specific embodiment, the invention includes a full-length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, and 4-1BB (CD137). In addition to a primary signal initiated by CD3ζ, an additional signal provided by a human costimulatory receptor inserted in a human CAR is important for full activation of NK cells and could help improve in vivo persistence and the therapeutic success of the adoptive immunotherapy.

The intracellular signaling domain of a chimeric antigen receptor is responsible for activation of at least one of the normal effector functions of the immune cell in which the chimeric antigen receptor has been placed. The term "effector function" refers to a specialized function of a differentiated cell, such as a NK cell. In specific embodiments, intracellular receptor signaling domains in the CAR include those of the T-cell antigen receptor complex, such as the zeta chain of CD3, also Fcγ RIII costimulatory signaling domains, CD28, CD27, DAP10, CD137, OX40, CD2, alone or in a series with CD3zeta, for example. In specific embodiments, the intracellular domain (which may be referred to as the cytoplasmic domain) comprises part or all of one or more of TCR zeta chain, CD28, CD27, OX40/CD134, 4-1BB/CD137, FcεRIγ, ICOS/CD278, IL-2Rbeta/CD122, IL-2Ralpha/CD132, DAP10, DAP12, and CD40. In some embodiments, one employs any part of the endogenous T-cell receptor complex in the intracellular domain. One or multiple cytoplasmic domains may be employed, as so-called third generation CARs have at least two or three signaling domains fused together for additive or synergistic effect, for example.

In certain embodiments of the chimeric antigen receptor, the antigen-specific portion of the receptor (which may be referred to as an extracellular domain comprising an antigen binding region) comprises a tumor associated antigen or a pathogen-specific antigen binding domain. Antigens include carbohydrate antigens recognized by pattern-recognition receptors, such as Dectin-1. A tumor associated antigen may be of any kind so long as it is expressed on the cell surface of tumor cells. Exemplary embodiments of tumor associated antigens include CD19, CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, and so forth. In certain embodiments, the CAR may be co-expressed with a cytokine to improve persistence when there is a low amount of tumor-associated antigen. For example, CAR may be co-expressed with IL-15.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into NK cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into NK cells. Suitable vectors for use in accordance with the method of the present invention are non-replicating in the NK cells. A large number of vectors are known that are based on viruses, where the copy number of the virus maintained in the cell is low enough to maintain the viability of the cell, such as, for example, vectors based on HIV, SV40, EBV, HSV, or BPV.

B. CD19-specific Chimeric Antigen Receptors

CD19, a cell surface glycoprotein of the immunoglobulin superfamily, is a potentially attractive target for antibody therapy of B cell-associated malignancies. This antigen is absent from hematopoietic stem cells, and in healthy individuals its presence is exclusively restricted to the B-lineage and possibly some follicular dendritic cells (Scheuermann et al., 1995). In fact, it is present on B cells from the earliest recognizable B-lineage cells during development to B-cell blasts but is lost on maturation to plasma cells. Furthermore, CD19 is not shed from the cell surface and rarely lost during neoplastic transformation (Scheuermann et al., 1995). The protein is expressed on most malignant B-lineage cells, including cells from patients with chronic lymphocytic leukemia (CLL), non-Hodgkin lymphoma (NHL), and acute lymphoblastic leukemia (ALL) (Uckun et al., 1988). CD19 primarily acts as a B cell co-receptor in conjunction with CD21 and CD81. Upon activation, the cytoplasmic tail of CD19 becomes phosphorylated, which leads to binding by Src-family kinases and recruitment of PI-3 kinase.

In one aspect, methods of the embodiments concern human CD19-specific chimeric T-cell receptor (or chimeric antigen receptor, CAR) polypeptide (designated hCD19CAR) comprising an intracellular signaling domain, a transmembrane domain, and an extracellular domain, the extracellular domain comprising a human CD19 binding region. In another aspect, the CD19 binding region is a F(ab')2, Fab', Fab, Fv, or scFv. The binding region may comprise an amino acid sequence that is at least, at most, or about 70%, 75%, 80%, 85%, 90%, 95%, 96%, 97%, 98%, 99%, or 100% identical to the wild-type amino acid sequence. The intracellular domain may comprise an intracellular signaling domain of human CD3ζ and may further comprise human CD28 intracellular segment. In certain aspects the transmembrane domain is a CD28 transmembrane domain.

C. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

In some cases, aAPCs are useful in preparing therapeutic compositions and cell therapy products of the embodiments. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009.

aAPC systems may comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD86, CD64 (FcγRI), 41BB ligand, and IL-21. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), which promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

In some embodiments, the presently disclosed process can be used to genetically modify NK cells derived from peripheral blood and/or umbilical cord blood to express CAR(s) that can be numerically expanded in vitro using aAPC (Singh et al., 2008; Singh et al., 2011; Shah et al., 2013). The process has implications for cell and gene therapy, due to the relative ease of DNA plasmid production, electroporation, use of thawed γ-irradiated master-bank aAPC, and can be readily transferred to facilities operating in compliance with current good manufacturing practice (cGMP) for clinical trials.

In one embodiment, aAPCs are also subjected to a freeze-thaw cycle. In an exemplary freeze-thaw cycle, the aAPCs may be frozen by contacting a suitable receptacle containing the aAPCs with an appropriate amount of liquid nitrogen, solid carbon dioxide (i.e., dry ice), or similar low-temperature material, such that freezing occurs rapidly. The frozen aAPCs are then thawed, either by removal of the aAPCs from the low-temperature material and exposure to ambient room temperature conditions, or by a facilitated thawing process in which a lukewarm water bath or warm hand is employed to facilitate a shorter thawing time. Additionally, aAPCs may be frozen and stored for an extended period of time prior to thawing. Frozen aAPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing aAPCs that undergo the freeze-thaw cycle, or are essentially removed, such as by transfer of aAPCs to media that is essentially devoid of such preservatives.

D. Interleukin-15

Interleukin-15 (IL-15) is tissue restricted and only under pathologic conditions is it observed at any level in the serum, or systemically. IL-15 possesses several attributes that are desirable for adoptive therapy. IL-15 is a homeostatic cytokine that induces development and cell proliferation of natural killer cells, promotes the eradication of established tumors via alleviating functional suppression of tumor-resident cells, and inhibits AICD.

In one embodiment, the disclosure provides a method of generating chimeric antigen receptor (CAR)-modified NK cells with long-lived in vivo potential for the purpose of treating, for example, leukemia patients. In aggregate, this method describes how soluble molecules such as cytokines can be fused to the cell surface to augment therapeutic potential. Certain aspects concern co-modifying CAR NK cells with IL-15. In addition to IL-15, other cytokines are envisioned. These include, but are not limited to, cytokines, chemokines, and other molecules that contribute to the activation and proliferation of cells used for human application. NK cells expressing IL-15 are capable of continued supportive cytokine signaling, which is critical to their survival post-infusion.

In certain embodiments, K562 aAPC were developed, expressing the desired antigen (e.g., CD19) along with costimulatory molecules, such as CD28, IL-15, and CD3ζ, to select for NK cells in vitro that are capable of sustained CAR-mediated propagation. This powerful technology allows the manufacture of clinically relevant numbers (up to $10^{10}$) of CAR$^+$ NK cells suitable for human application. As needed, additional stimulation cycles can be undertaken to generate larger numbers of genetically modified NK cells. Typically, at least 90% of the propagated NK cells express CAR and can be cryopreserved for infusion. Furthermore, this approach can be harnessed to generate NK cells to diverse tumor types by pairing the specificity of the introduced CAR with expression of the tumor-associated antigen (TAA) recognized by the CAR on the aAPC.

Following genetic modification the cells may be immediately infused or may be stored. In certain aspects, following genetic modification, the cells may be propagated for days, weeks, or months ex vivo as a bulk population within about 1, 2, 3, 4, 5 days or more following gene transfer into cells. In a further aspect, following g, the transfectants are cloned and a clone demonstrating presence of a single integrated or episomally maintained expression cassette or plasmid, and expression of the chimeric receptor is expanded ex vivo. The clone selected for expansion demonstrates the capacity to specifically recognize and lyse CD19 expressing target cells. The recombinant NK cells may be expanded by stimulation with IL-2, or other cytokines that bind the common gamma-chain (e.g., IL-7, IL-12, IL-15, IL-21, and others). The recombinant NK cells may be expanded by stimulation with artificial antigen presenting cells. In a further aspect, the genetically modified cells may be cryopreserved.

E. Genotyping

Embodiments concern the NK cell genotype of the killer immunoglobulin-like receptors (KIRs). The KIRs are one of the main types of MHC class I-specific receptors utilized by NK cells. Certain aspects concern the genotype of both the inhibitory and activating KIRs that are encoded by highly homologous sequences. For example, the genotyping of the NK cell MR can be performed to identify the presence or absence of MR genes including 2DL1, 2DL2, 2DL3, 2DL4, 2DL5, 2DS1, 2DS2, 2DS3, 2DS4, 3DL1, 3DL2, 3DL3, 3DS1, 2DP1, 3DP1, as well as common variants 2DL5, 2DS4, and 3DP1. Genotyping can be performed by methodologies such as polymerase chain reaction (PCR), restriction fragment polymorphism identification (RFPLI), random amplified polymorphic detection (RAPD), amplified fragment length polymorphism detection (AFLPD), DNA sequencing, allele specific oligonucleotide (ASO) probes, and hybridization to DNA microarrays or beads. For example, PCR uses specific primer sets to amplify genomic DNA and gel electrophoresis can be used for detection. In this method, DNA is isolated from tissues or cells using previously described protocols. Oligonucleotide primer mixes containing forward and reverse primers for the MR genes are used to amplify DNA. The DNA can then be run on an agarose gel to determine the genotype for the MR genes.

In another aspect, multiplex PCR-SSP (sequence-specific priming) can be performed using agarose gel electrophoresis (Kulkarni et al., 2010). In yet another method, matrix-assisted laser desorption-ionization time-of-flight (MALDI-TOF) mass spectrometry is used to detect the presence or absence of SNPs of the MR genes by MALDI-TOF mass spectrometry after amplifying the target sequences of KIR genes (see Houtchens et al., 2007). Another method can use sequence specific oligonucleotide probes (SSOP) developed for the locus-specific resolution of the KIR genes. In this method, genomic DNA is amplified at four MR domains, PCR products are denatured and vacuum blotted onto replicated nylon membranes. The replicated membranes are then hybridized to sequence-specific probes, washed under stringent conditions to remove the unbound probes and are then decoded using a computer program.

In another aspect, HLA-C locus genotyping is performed. For example, genotyping is performed to determine if a subject has the HLA-C genotype of C1/C1, C1/C2, or C2/C2. In this aspect, genotyping can be performed by methodologies previously described. In certain aspects, the DNA can be isolated from fresh or cryopreserved cells, tissue, or blood. In one method, PCR is followed by sequence specific oligonucleotide probe-hybridization of the HLA-C locus.

Embodiments concern the matching of a specific MR genotype with a specific HLA-C genotype. In certain embodiments, the NK cells are identified to express a HLA-C1-licensed KIR2DL2, KIR2DL3, and KIR2DS2. In this embodiment, the HLA-C1-licensed NK cells are administered to a subject identified to have an HLA-C genotype either homozygous or heterozygous for the C1 allele (i.e., C1/C1 or C1/C2). In another embodiment, the NK cells are identified to express a HLA-C2-licensed KIR2DL1 and KIR2DS1 genotype. In this embodiment, the HLA-C2-licensed NK cells are administered to a subject identified to have an HLA-C genotype homozygous for the C2 allele (i.e., C2/C2).

IV. METHODS OF TREATMENT

In some embodiments, a medical disease or disorder is treated by transfer of a NK cell population that elicits an immune response. In certain embodiments of the present disclosure, cancer or infection is treated by transfer of a NK cell population that elicits an immune response. NK cells are innate lymphoid cells that hold tremendous potential for effective immunotherapy for a broad range of cancers. NK cells require one-to-one target engagement and site-directed release of cytolytic granules. Their ability to precisely kill antibody coated cells, cancer stem cells, and genotoxically altered cells, while maintaining tolerance to healthy cells makes them appealing for all cancer forms, including metastasis (Navarro et al., 2015). Due to their release of proinflammatory cytokines, NK cells may reverse the anti-inflammatory tumor microenvironment and increase adaptive immune responses by promoting differentiation, activation, and/or recruitment of accessory immune cell to sites of malignancy.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma;

adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

Particular embodiments concern methods of treatment of leukemia. Leukemia is a cancer of the blood or bone marrow and is characterized by an abnormal proliferation (production by multiplication) of blood cells, usually white blood cells (leukocytes). It is part of the broad group of diseases called hematological neoplasms. Leukemia is a broad term covering a spectrum of diseases. Leukemia is clinically and pathologically split into its acute and chronic forms.

Acute leukemia is characterized by the rapid proliferation of immature blood cells. This crowding makes the bone marrow unable to produce healthy blood cells. Acute forms of leukemia can occur in children and young adults. In fact, it is a more common cause of death for children in the U.S. than any other type of malignant disease. Immediate treatment is required in acute leukemia due to the rapid progression and accumulation of the malignant cells, which then spill over into the bloodstream and spread to other organs of the body. Central nervous system (CNS) involvement is uncommon, although the disease can occasionally cause cranial nerve palsies. Chronic leukemia is distinguished by the excessive build up of relatively mature, but still abnormal, blood cells. Typically taking months to years to progress, the cells are produced at a much higher rate than normal cells, resulting in many abnormal white blood cells in the blood. Chronic leukemia mostly occurs in older people, but can theoretically occur in any age group. Whereas acute leukemia must be treated immediately, chronic forms are sometimes monitored for some time before treatment to ensure maximum effectiveness of therapy.

Furthermore, the diseases are classified into lymphocytic or lymphoblastic, which indicate that the cancerous change took place in a type of marrow cell that normally goes on to form lymphocytes, and myelogenous or myeloid, which indicate that the cancerous change took place in a type of marrow cell that normally goes on to form red cells, some types of white cells, and platelets (see lymphoid cells vs. myeloid cells).

Acute lymphocytic leukemia (also known as acute lymphoblastic leukemia, or ALL) is the most common type of leukemia in young children. This disease also affects adults, especially those aged 65 and older. Chronic lymphocytic leukemia (CLL) most often affects adults over the age of 55. It sometimes occurs in younger adults, but it almost never affects children. Acute myelogenous leukemia (also known as acute myeloid leukemia, or AML) occurs more commonly in adults than in children. This type of leukemia was previously called "acute nonlymphocytic leukemia." Chronic myelogenous leukemia (CML) occurs mainly in adults. A very small number of children also develop this disease.

Lymphoma is a type of cancer that originates in lymphocytes (a type of white blood cell in the vertebrate immune system). There are many types of lymphoma. According to the U.S. National Institutes of Health, lymphomas account for about five percent of all cases of cancer in the United States, and Hodgkin's lymphoma in particular accounts for less than one percent of all cases of cancer in the United States. Because the lymphatic system is part of the body's immune system, patients with a weakened immune system, such as from HIV infection or from certain drugs or medication, also have a higher incidence of lymphoma.

In certain embodiments of the invention, NK cells are delivered to an individual in need thereof, such as an individual that has cancer or an infection. The cells then enhance the individual's immune system to attack the respective cancer or pathogenic cells. In some cases, the individual is provided with one or more doses of the NK-cells. In cases where the individual is provided with two or more doses of the NK-cells, the duration between the administrations should be sufficient to allow time for propagation in the individual, and in specific embodiments the duration between doses is 1, 2, 3, 4, 5, 6, 7, or more days.

The source of NK cells that are modified to include a chimeric antigen receptor and are licensed to a specific MR genotype may be of any kind, but in specific embodiments the cells are obtained from a bank of umbilical cord blood, peripheral blood, human embryonic stem cells, or induced pluripotent stem cells, for example. Suitable doses for a therapeutic effect would be at least $10^5$ or between about $10^5$ and about $10^{10}$ cells per dose, for example, preferably in a series of dosing cycles. An exemplary dosing regimen consists of four one-week dosing cycles of escalating doses, starting at least at about $10^5$ cells on Day 0, for example increasing incrementally up to a target dose of about $10^{10}$ cells within several weeks of initiating an intra-patient dose escalation scheme. Suitable modes of administration include intravenous, subcutaneous, intracavitary (for example by reservoir-access device), intraperitoneal, and direct injection into a tumor mass.

A pharmaceutical composition of the present invention can be used alone or in combination with other well-established agents useful for treating cancer. Whether delivered alone or in combination with other agents, the pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

In certain embodiments, the NK cells are administered in combination with a second therapeutic agent. For example, the second therapeutic agent may comprise T cells, an immunomodulatory agent, a monoclonal antibody, or a chemotherapeutic agent. In non-limiting examples, the immunomodulatory agent is lenolidomide, the monoclonal antibody is rituximab, ofatumab, or lumiliximab, and the chemotherapeutic agent is fludarabine or cyclophosphamide.

A composition of the present invention can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular subject.

Desirably an effective amount or sufficient number of the isolated transduced NK cells is present in the composition and introduced into the subject such that long-term, specific, anti-tumor responses are established to reduce the size of a tumor or eliminate tumor growth or regrowth than would otherwise result in the absence of such treatment. Desirably, the amount of NK cells reintroduced into the subject causes a 10%, 20%, 30%, 40%, 50%, 60%, 70%, 80%, 90%, 95%, 98%, or 100% decrease in tumor size when compared to otherwise same conditions wherein the NK cells are not present.

Accordingly, the amount of NK cells administered should take into account the route of administration and should be such that a sufficient number of the NK cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of NK cells desirably should be sufficient to provide in the subject being treated at least from about $1 \times 10^6$ to about $1 \times 10^9$ NK cells, even more desirably, from about $1 \times 10^7$ to about $5 \times 10^8$ NK cells, although any suitable amount can be utilized either above, e.g., greater than $5 \times 10^8$ cells, or below, e.g., less than $1 \times 10^7$ cells. The dosing schedule can be based on well-established cell-based therapies (see, e.g., Topalian and Rosenberg, 1987; U.S. Pat. No. 4,690,915), or an alternate continuous infusion strategy can be employed.

These values provide general guidance of the range of NK cells to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Genetic Engineering of Cord Blood-Derived NK Cells

Figure 1B:
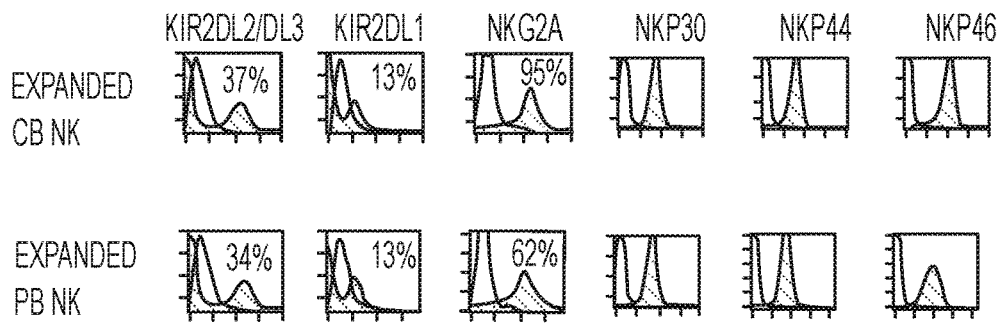
Figure 1C:
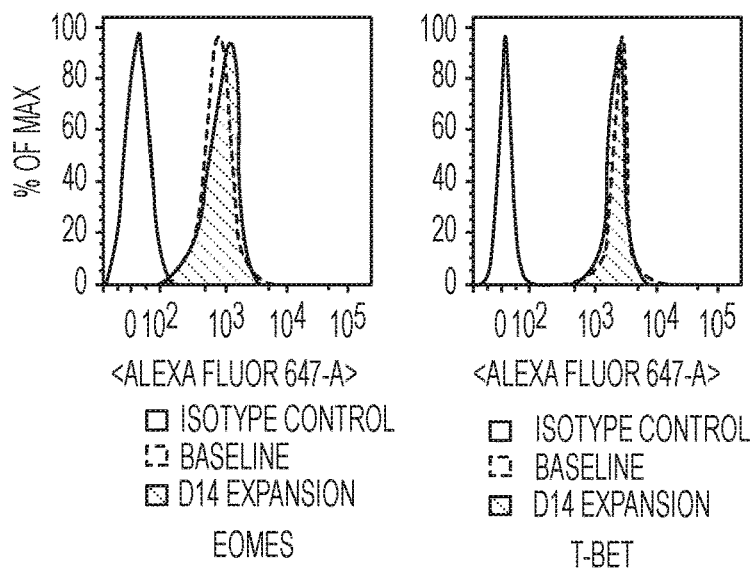
Figure 1D:
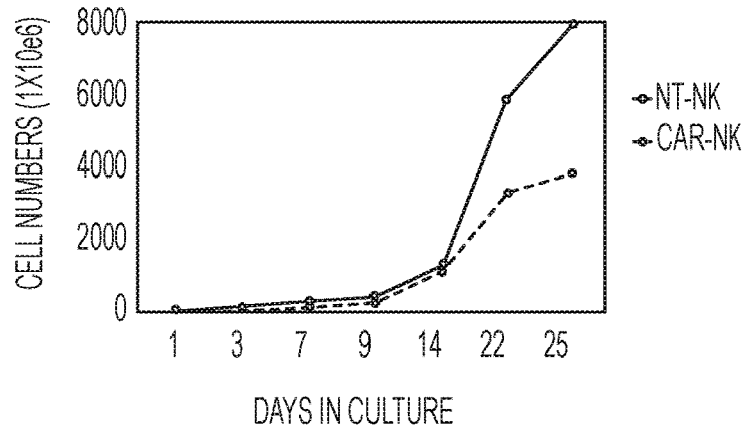
Figure 1E:
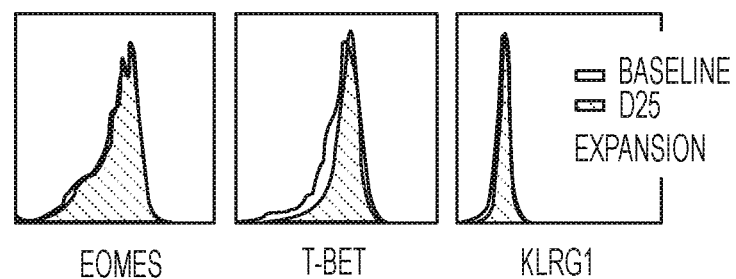
Figure 1F:
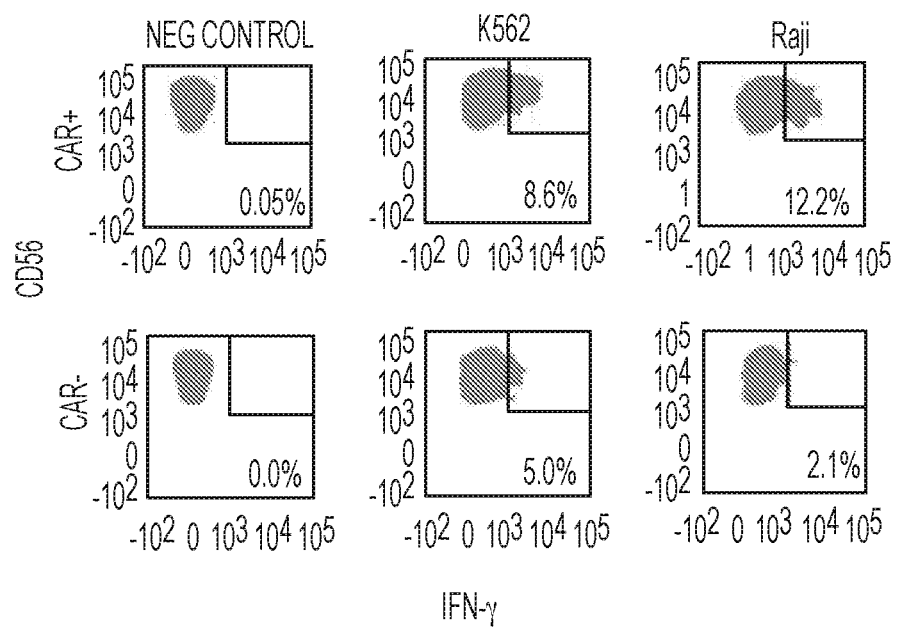

NK cells were derived from cord blood and their specificity was redirected by genetically engineering them to express tumor-specific chimeric antigen receptors (CARs) that could enhance their anti-tumor activity without increasing the risk of graft-versus-host disease (GVHD), thus providing an 'off-the-shelf' source of cells for therapy, such as immunotherapy of CLL. For genetic modification, CB-NK cells were transduced with a retroviral construct (CD19-CD28-zeta-2A-iCasp9-IL15) to redirect their specificity to recognize the tumor antigen CD-19. The transduction efficiency of the CB-NK cells transduced with the retroviral vector was monitored over 44 days and transgene expression was found to be stable (FIG. 1A). The CB-NK cells displayed a mature array of activating and inhibitory receptors (FIG. 1B) and did not undergo exhaustion (FIG. 1E). Also, the CB-NK cells expanded by aAPCs maintained an Eomes$^{hi}$ and T-bet$^{hi}$ phenotype (FIG. 1C) and showed increased IFN-γ cytokine production against K562 or CD19$^+$ cells (FIG. 1F).

Figure 1G:
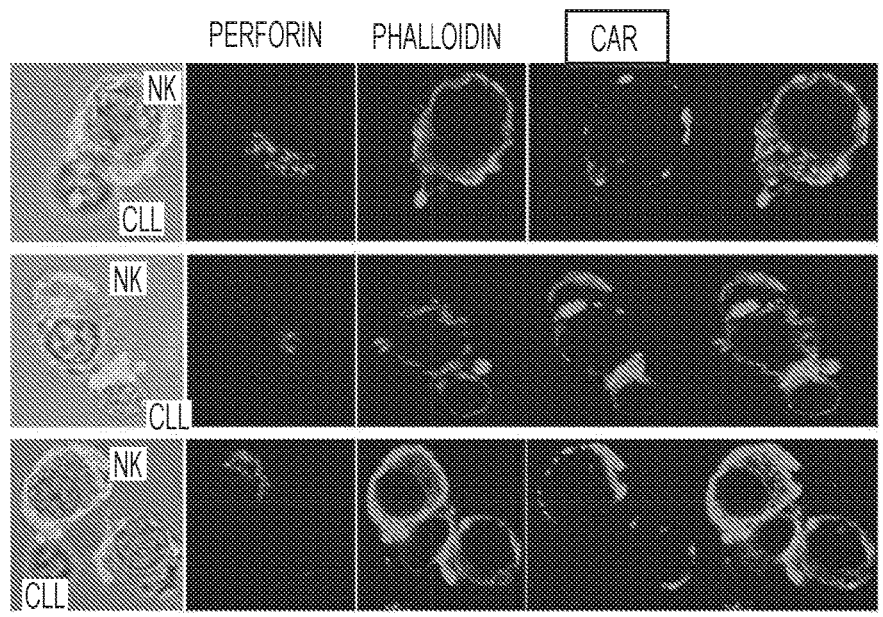
Figure 1H:
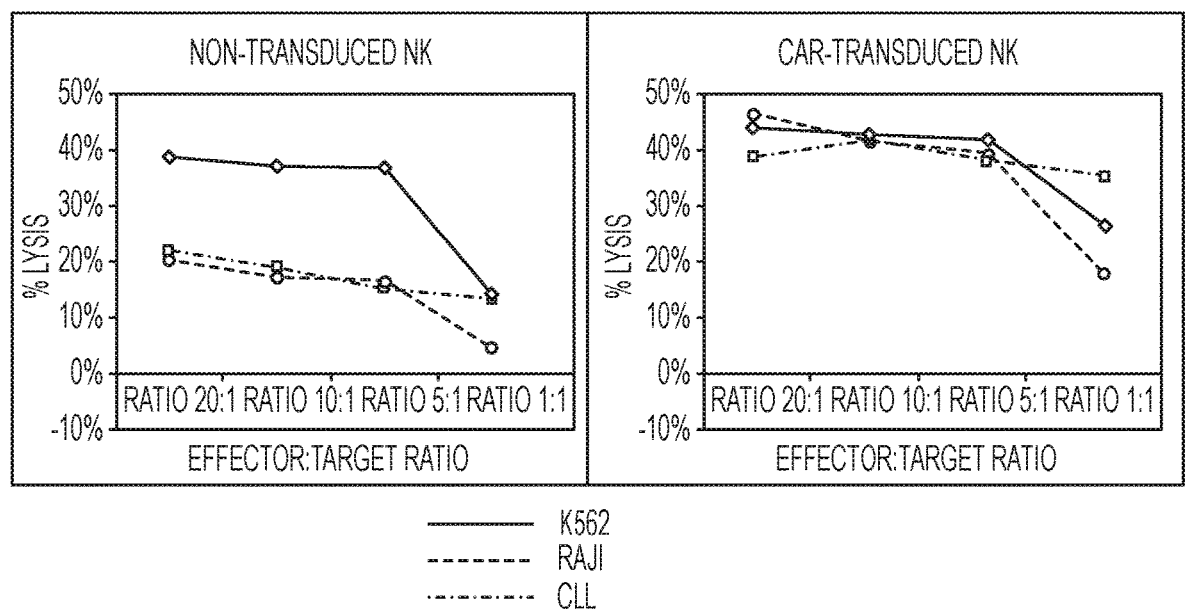
Figure 1I:
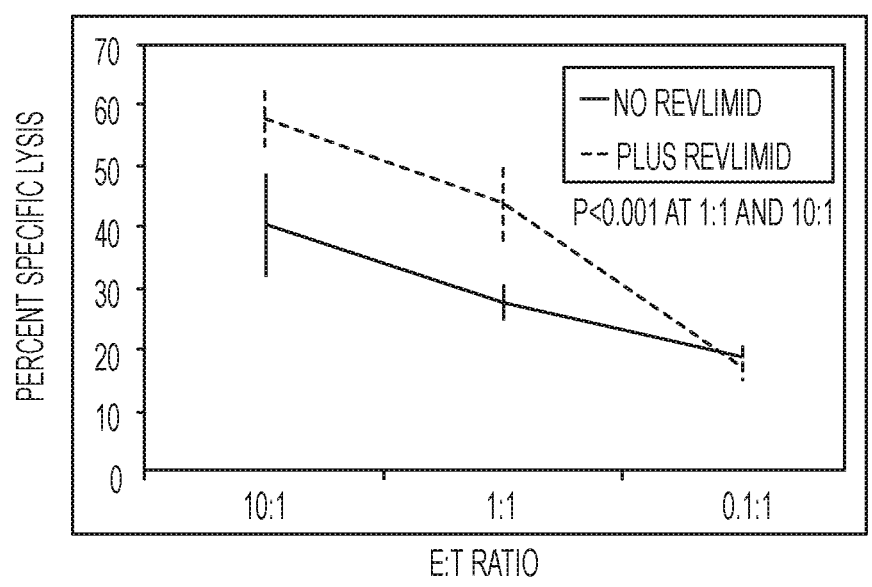

The immunological synapse in immune cells is a discrete structural entity that forms after the ligation of a specific activation receptor and enables the cell to progress through a series of biological steps that allow it to destroy cancer cells through the elaboration of the contents of NK cells lytic granules. To determine if the CAR-transduced NK cells formed immunological synapses with CD19$^+$ targets, the cells were stained with antiperforin, Phalloidin-F-actin and anti-CD19-CAR. The staining was imaged by confocal microscopy on the NK cells conjugated with primary CLL cells and CD19-CAR transduced unconjugated NK cells, and an accumulation of synapses was seen in CAR-transduced NK cells (FIG. 1G). In addition, the CAR-transduced NK cells were found to be more cytotoxic to primary CD19$^+$ tumor cells than NK cells without CAR (FIG. 1H) and have enhanced activity against patient-derived CLL cells, which is enhanced synergistically by the addition of lenalidomide (FIG. 1I).

Example 2—In Vivo Evaluation of Cord Blood-Derived NK Cells

Figure 2A:
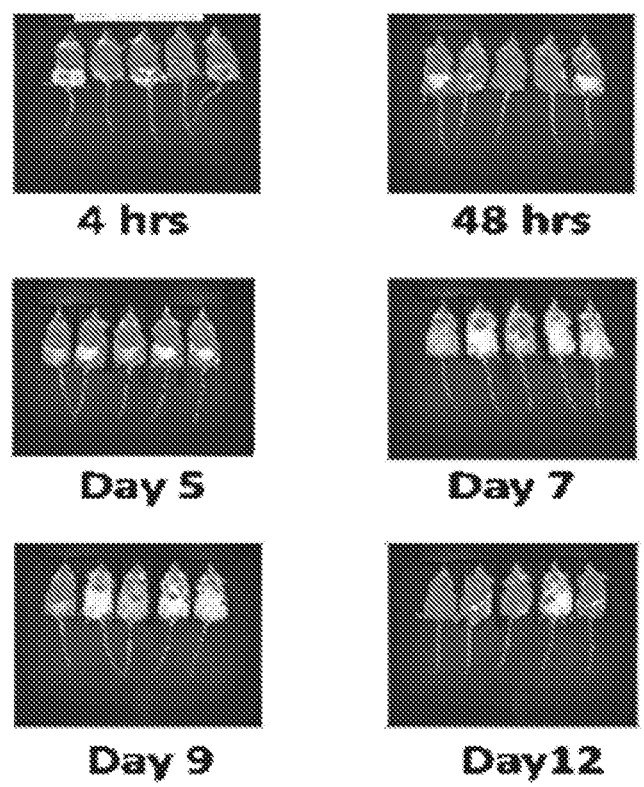
FIGS. 2A-2I: (A) Infusion of luciferase-expressing expanded CB-NK cells into Raji engrafted mice reveals trafficking to the spleen and BM, as evidenced by in vivo bioluminescence imaging. (B) Spleen from NK cell-untreated compared to cell-treated Raji engrafted mice shows eradication of leukemia. (C) CAR-NK cells home to sites of disease, such as the spleen, bone marrow, and liver, in a Raji engrafted mouse at Day 16 post-infusion. (D) CAR-NK cells persist in Raji engrafted mice at Day 70 post infusion. (E) CAR-transduced CB-NK cells show an anti-tumor effect in vivo in Raji-FFLuc mice from Day 0 to Day 14. (F) CAR-transduced CB-NK cells show an anti-tumor effect in vivo in Raji-FFLuc mice from Day 21 to Day 35. (G) Raji engrafted mice transduced with CAR-NK cells show increased IL-15, IL1-b, and IL-4. (H) Survival curve with different NK cell treatments. (I) CAR.19.IL15-iCasp9 transduced CB-NK cells are eliminated after activation of the suicide gene by exposure to the small molecule AP1903 after 4 hours.
Figure 2B:
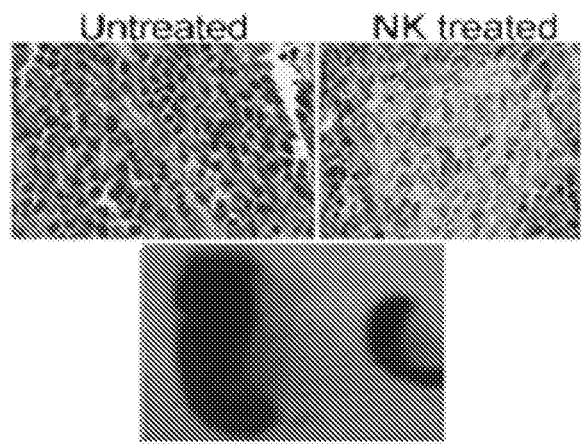
Figure 2C:
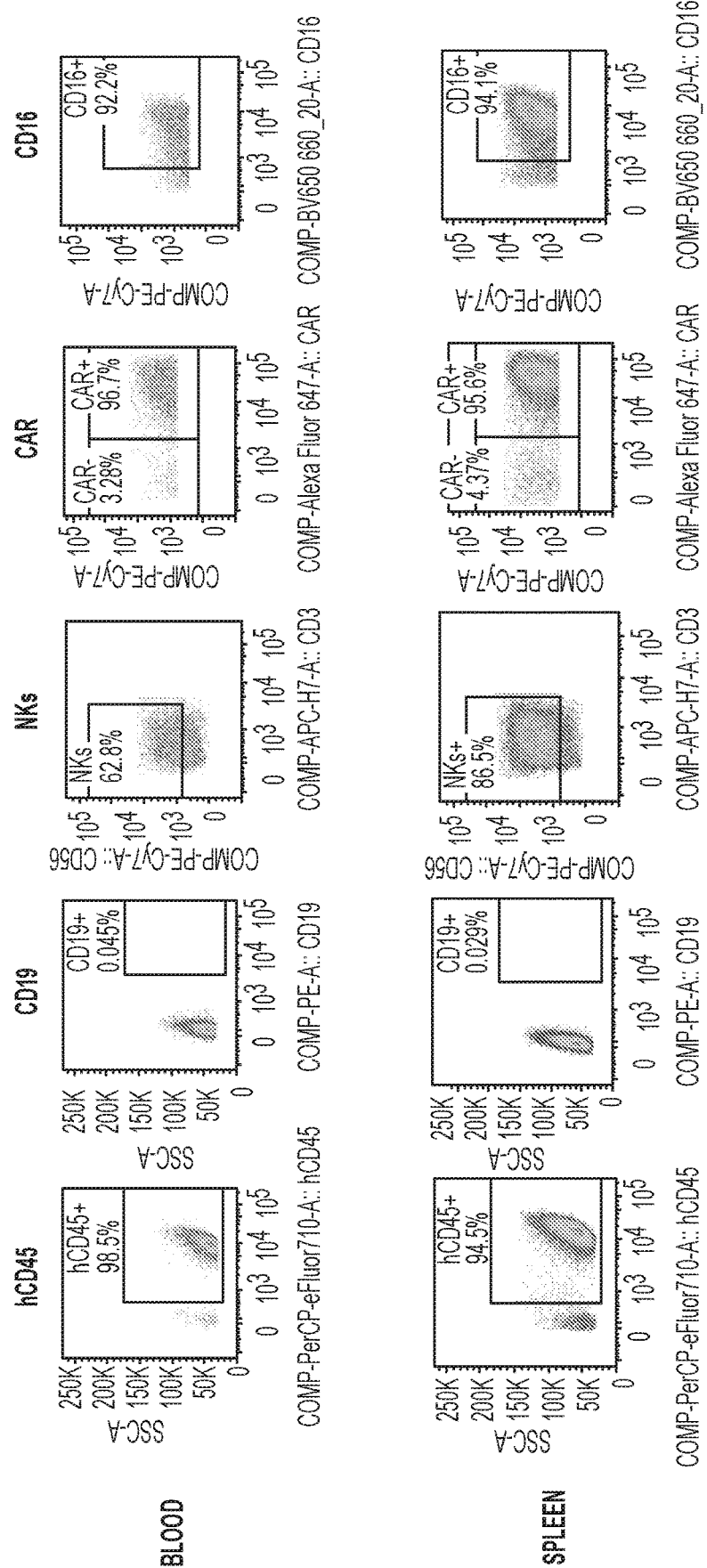
Figure 2C:
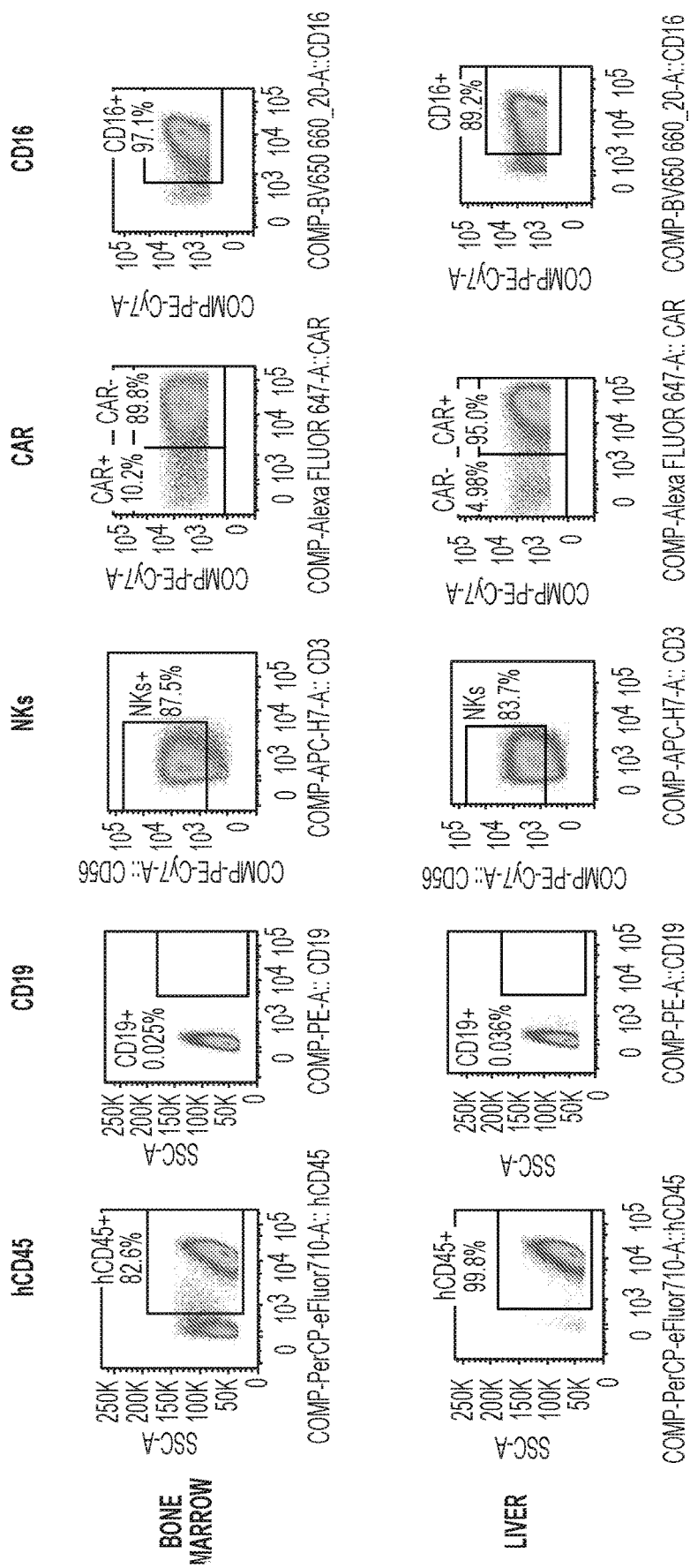
Figure 2D:
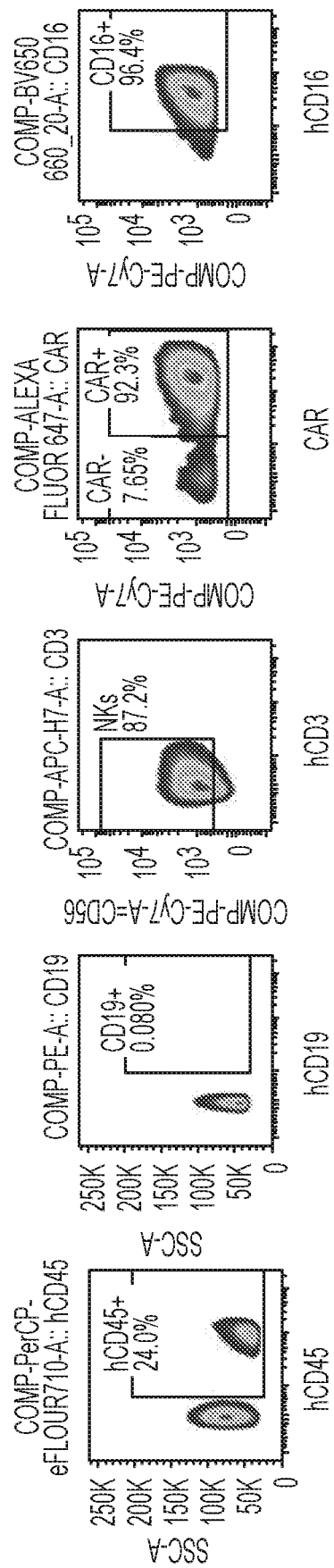
Figure 2E:
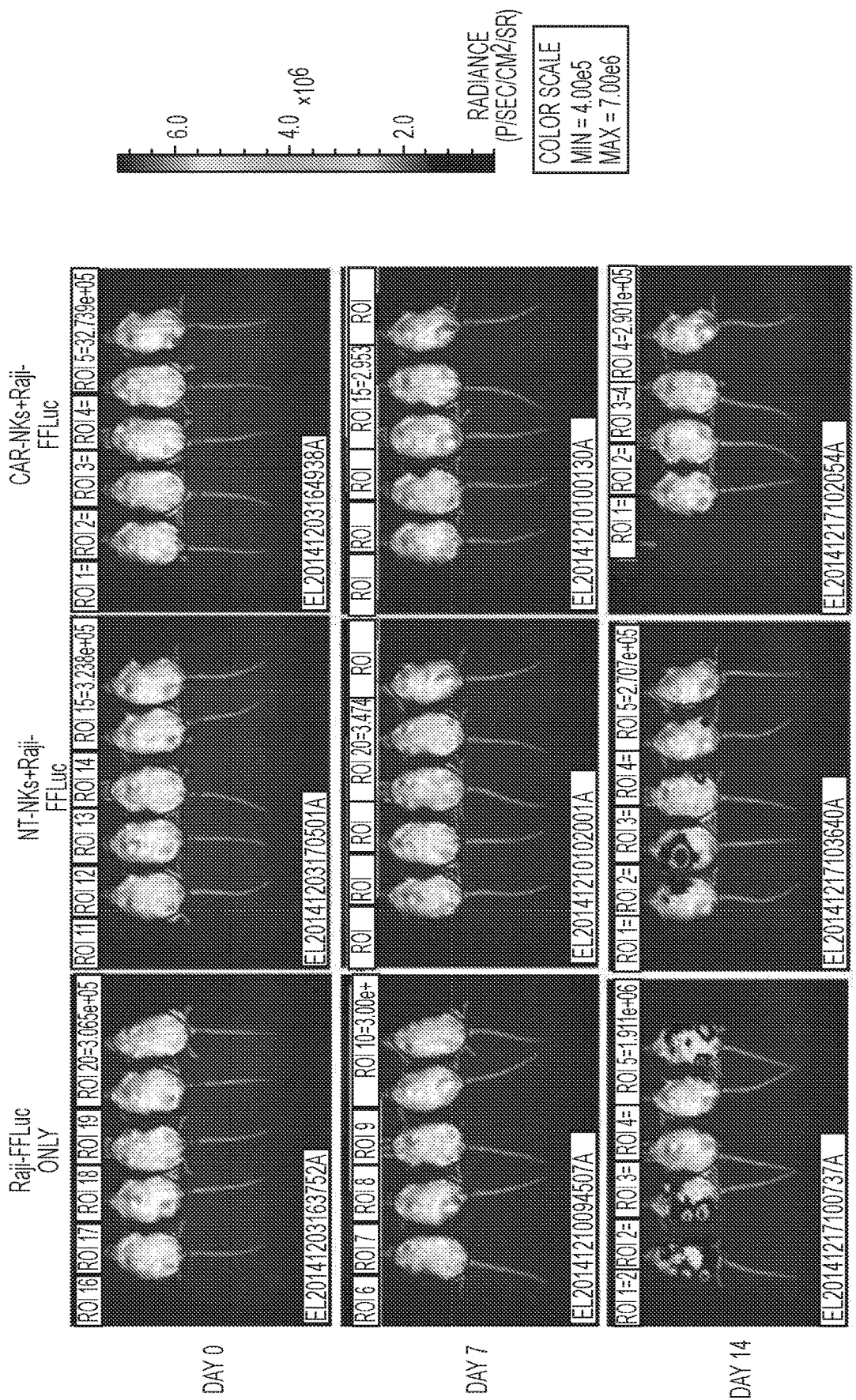
Figure 2F:
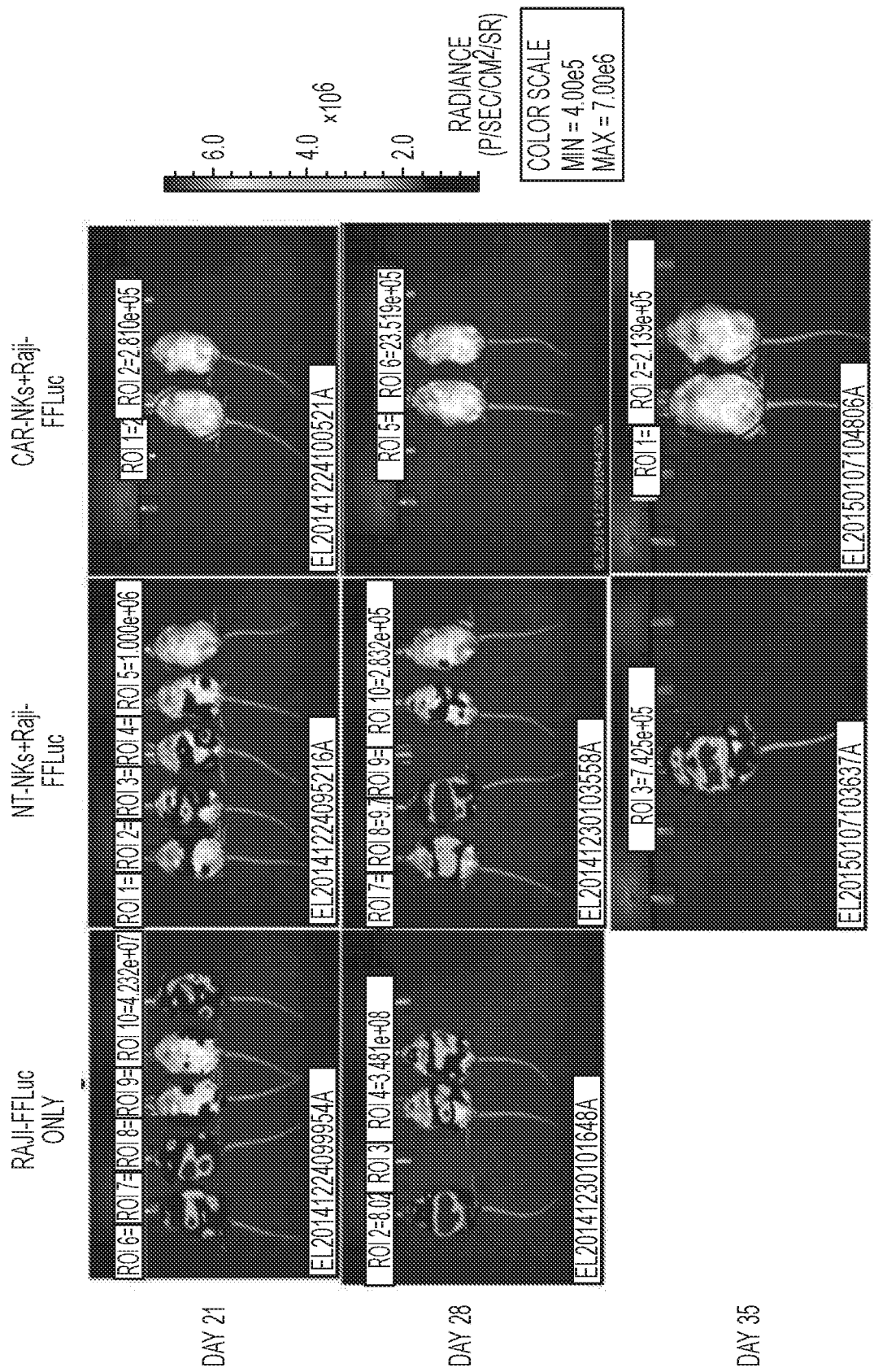
Figure 2G:
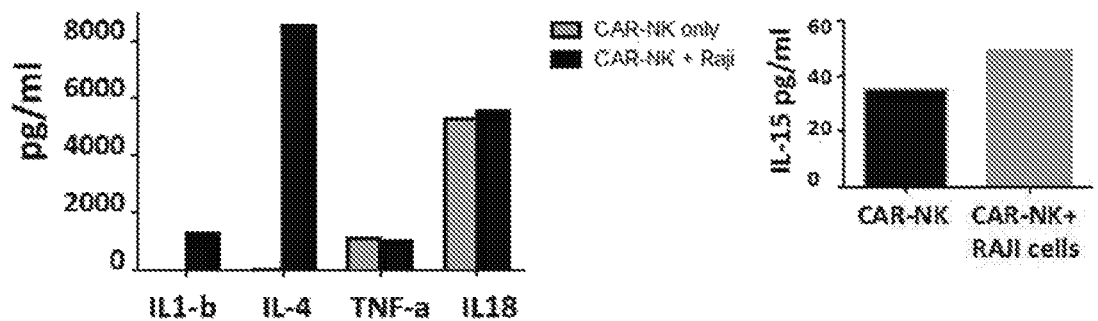
Figure 2H:
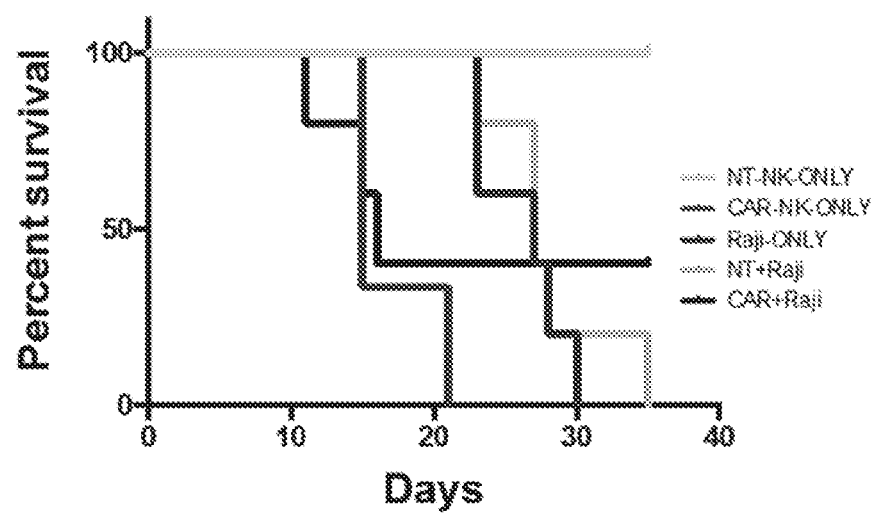

To determine the anti-leukemic effect of the CAR-transduced NK cells, they were infused into a "humanized" mouse model of lymphoblastic leukemia, the luciferase-expressing Raji NSG mouse model. To monitor the trafficking of CAR-CD19+ CB-NK cells to tumor sites in vivo, the cells were labeled with the FFLuc vector, enabling monitoring by bioluminescence imaging. Engrafted mice received CD19$^+$ Raji leukemic B cells (2×10$^6$) injected intravenously and labeled with the RLuc vector to monitor tumor growth. Six to 10 days after tumor engraftment, mice were infused intravenously with 2×10$^7$ expanded CB-NK cells that were unmodified or expressed transgenic CD19/CD28 or IL-15 alone as controls, or CAR19-CD28-zeta-2A-IL15 CB-NK cells labeled with FFLuc. All imaging was performed once a week for 3 weeks. Four groups of animals (n=10 per group) were studied, and the spleens, blood and lymph nodes of the mice were collected after they were euthanized. The adoptively infused CAR-transduced CB-NK cells homed to sites of disease (liver, spleen, bone marrow) (FIGS. 2A-2C) and persisted for up to 90 days post-infusion, supporting the hypothesis that IL-15 will enhance the proliferation and survival of the engineered NK cells (FIG. 2D). Importantly, human CAR-transduced CB-NK cells did not induce xenogenic GVHD. The CAR-transduced cells resulted in strong anti-tumor response, as evidenced by in vivo bioluminescence imaging (FIGS. 2E-2F). The CAR.CD19.IL15-transduced CB-NK cells were found to proliferate, expand and persist long-term in blood following infusion into the NSG Raji mouse model. The infusion of CAR.CD19.IL15-transduced CB NK cells into the Raji mouse model resulted in long-term anti-tumor responses, associated with a "cytokine-release syndrome" (FIGS. 2G-2H).

Figure 2I:
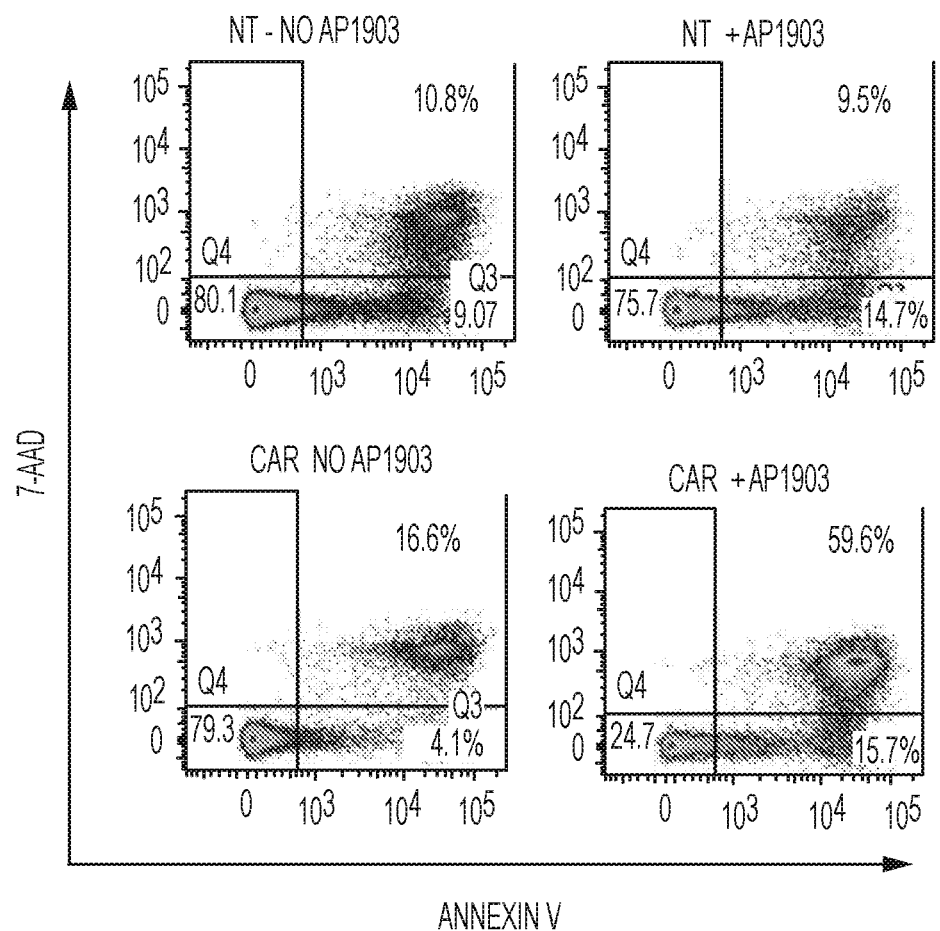

Because of concerns over autonomous, uncontrolled NK-cell growth due to autocrine production of IL-15, a suicide gene based on the inducible caspase-9 (IC9) gene was incorporated into the construct. To test the inducible caspase-9 suicide gene that was incorporated into the retroviral vector, 10 nM of CID AP20187 was added to cultures of iC9/CAR19/IL15+ NK cells. The AP20187 induced apoptosis/necrosis of transgenic cells within 4 hours as assessed by annexin-V-7AAD staining (FIG. 2I).

Figure 3A:
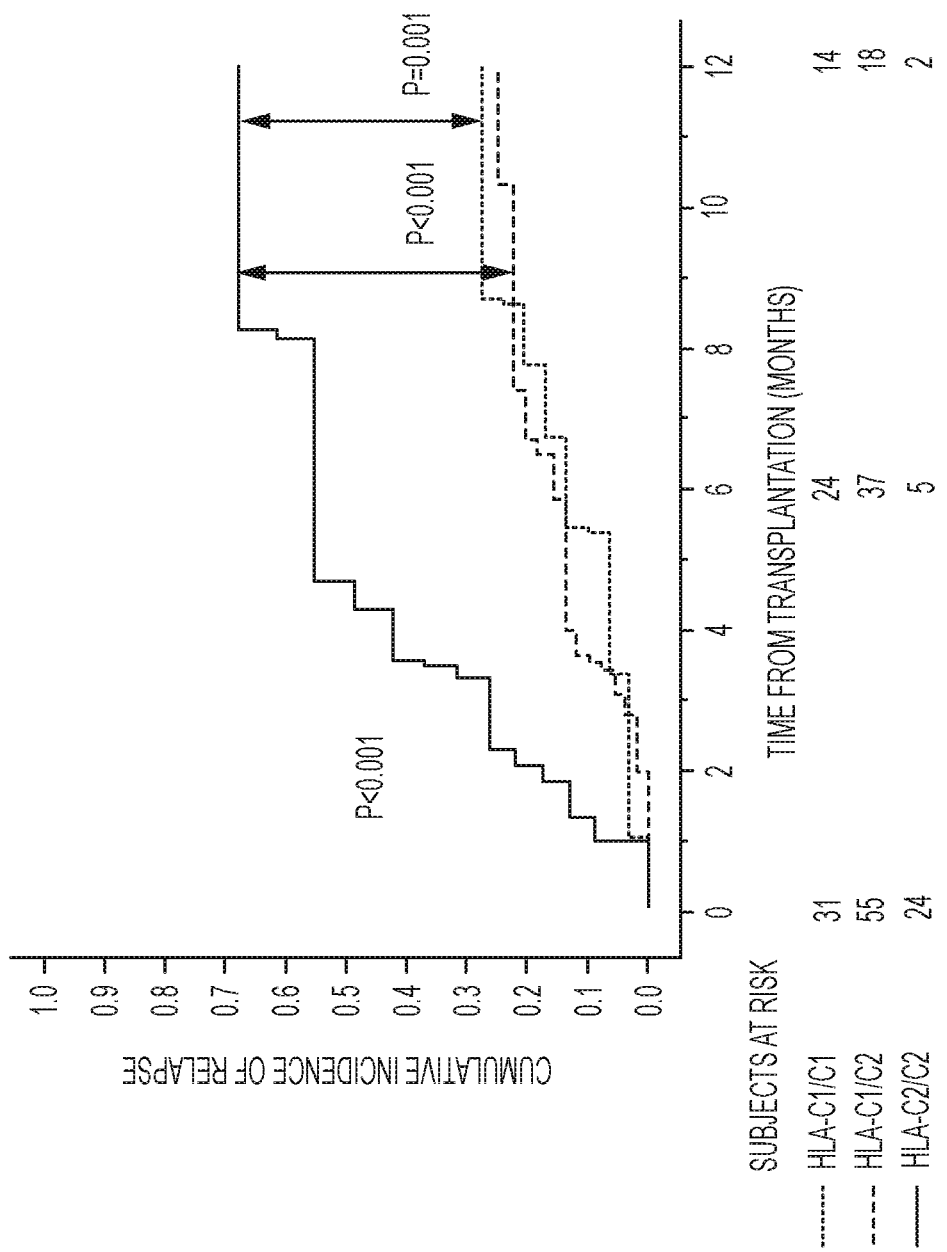
FIGS. 3A-3B: Effect of recipient HLA-C genotype on clinical outcome after CBT in the 110 patients in the discovery cohort. (A) One-year cumulative incidence of relapse. (B) one-year probability of OS.
Figure 3B:
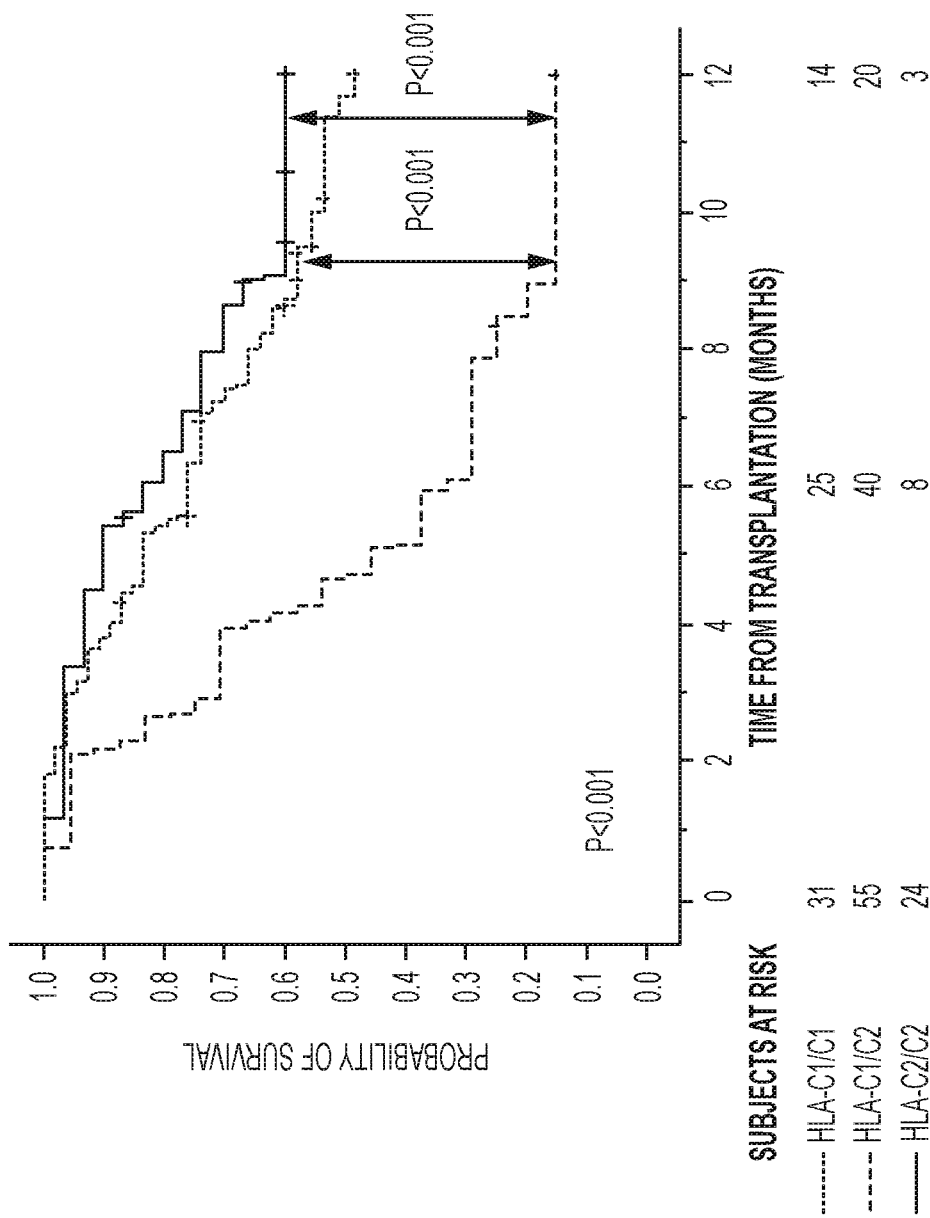

Example 3—Recipient HLA-C Genotypes Associated with Distinct Outcomes in Patients Undergoing CBT Patients were classified according to the presence of genes encoding recipient HLA-C ligands for donor inhibitory KIRs. Table 2 summarizes the HLA-C group 1 (C1) and group 2 (C2)-related alleles. The 24 patients who were HLA-C2 homozygous had a significantly higher risk of relapse and a worse OS than the 31 patients with HLA-C1/C1 or the 55 patients with HLA-C1/C2 genotypes (Table 1A and FIG. 3), regardless of whether the underlying malignancy was of myeloid or lymphoid origin (Table 3). These findings were validated in an independent cohort of 94 CBT patients (Table 1B).

TABLE 1

Patient characteristics and outcomes in the discovery (n = 110) and validation (n = 94) cohorts.

A. Discovery cohort

| | | 1-year overall survival | | 1-year relapse rate | |
|---|---|---|---|---|---|
| | | | | Cumulative | |
| | n | Probability (%) | HR (95% CI) (risk of death) | incidence (%) | HR (95% CI) (risk of relapse) |
| Age$^f$ | | p = 0.08 | | p = 0.74 | |
| ≤40 yr | 59 | 52.4 | 1 | 32.7 | 1 |
| >40 yr | 51 | 35.6 | 1.57 (0.94-2.63) | 36.0 | 1.12 (0.56-2.22) |
| Sex | | p = 0.23 | | p = 0.24 | |
| Male | 48 | 40.6 | 1 | 40.5 | 1 |
| Female | 62 | 47.9 | 0.73 (0.44-1.22) | 35.1 | 0.66 (0.23-1.61) |
| Diagnosis | | p = 0.75 | | p = 0.40 | |
| Acute myeloid leukemia | 44 | 41.5 | 1 | 41.0 | 1 |

TABLE 1-continued

Patient characteristics and outcomes in the discovery (n = 110) and validation (n = 94) cohorts.

| | n | Probability (%) | HR (95% CI) (risk of death) | incidence (%) | HR (95% CI) (risk of relapse) |
|---|---|---|---|---|---|
| Acute lymphoblastic leukemia | 24 | 41.7 | 0.95 (0.49-1.84) | 23.1 | 0.51 (0.18-1.38) |
| Myelodysplastic syndromes | 19 | 40.6 | 1.00 (0.49-2.0) | 47.6 | 1.06 (0.45-2.48) |
| Lymphoproliferative disorder [II] | 22 | 43.3 | 0.75 (0.28-1.51) | 30.3 | 0.44 (0.13-1.50) |
| Chronic myeloid leukemia | 1 | 100.0 | — | 0.0 | — |
| Disease status at transplant | | p = 0.06 | | P = 0.006 | |
| Complete remission | 67 | 52.9 | 1 | 23.2 | 1 |
| Refractory/relapsed disease | 43 | 31.9 | 1.63 (0.97-2.73) | 51.3 | 2.55 (1.27-5.10) |
| Conditioning regimen | | p = 0.20 | | p = 0.55 | |
| Myeloablative | 79 | 38.1 | 1 | 46.3 | 1 |
| Non-myeloablative | 31 | 22.1 | 1.19 (0.67-2.09) | 40.9 | 0.56 (0.23-1.36) |
| Graft | | p = 0.22 | | p = 0.20 | |
| Double cord | 105 | 45.9 | 1 | 32.6 | 1 |
| Single cord | 5 | 20.0 | 1.36 (0.82-2.27) | 0.60 | 1.51 (0.84-2.74) |
| CMV status[III] | | p = 0.84 | | p = 0.43 | |
| Seronegative | 11 | 53.0 | 1 | 56.2 | 1 |
| Seropositive | 97 | 43.6 | 1.10 (0.44-2.75) | 32.0 | 0.66 (0.23-1.89) |
| HLA match between recipient and dominant CB unit[IV] | | p = 0.50 | | p = 0.34 | |
| 7-8/8 | 16 | 61.4 | 1 | 25.1 | 1 |
| 5-6/8 | 46 | 47.1 | 1.41 (0.48-4.13) | 30.1 | 1.33 (0.42-6.01) |
| ≤4/8 | 38 | 40.8 | 1.80 (0.61-5.27) | 39.6 | 1.60 (0.61-4.81) |
| Total mononuclear cells infused[V] | | p = 0.90 | | p = 0.99 | |
| ≤4.1 × 10$^8$/kg | 56 | 46.1 | 1 | 34.2 | 1 |
| >4.1 × 10$^8$/kg | 54 | 42.6 | 1.035 (0.62-1.73) | 33.5 | 0.99 (0.50-1.96) |
| Patient HLA C group | | p < 0.001 | | p < 0.001 | |
| C1/C1 | 31 | 59.9 | 1 | 27.3 | 1 |
| C1/C2 | 55 | 48.7 | 1.35 (0.68-2.67) | 24.9 | 0.92 (0.38-2.26) |
| C2/C2 | 24 | 15.0 | 4.33 (2.10-8.94) | 67.8 | 4.05 (1.66-9.87) |
| Patient HLA C group | | p < 0.001 | | p < 0.001 | |
| C1/x | 86 | 52.9 | 1 | 26.0 | 1 |
| C2/C2 | 24 | 15.0 | 3.56 (2.05-6.18) | 67.8 | 4.25 (2.09-8.63) |
| Patients receiving CB grafts with the combined HLA-C1-KIR2DL2/L3/S2 genotype [VI] | | p = 0.002 | | p = 0.009 | |
| Yes | 67 | 64.6 | 1 | 46.9 | 1 |
| No | 37 | 34.3 | 2.65 (1.39-5.03) | 16.0 | 3.07 (1.26-7.47) |
| HLA-C1/x patients receiving CB grafts with the combined HLA-C1-KIR2DL2/L3/S2 genotype [VI] | | p = 0.003 | | p = 0.002 | |
| Yes | 31 | 74.2 | 1 | 6.7 | 1 |
| No | 49 | 41.3 | 3.31 (1.45-7.50) | 40.1 | 6.98 (1.61-30.25) |
| Patients receiving CB grafts with the combined HLA-C2-KIR2DL1/S1 genotype [VI] | | p = 0.17 | | p = 0.72 | |
| Yes | 47 | 51.9 | 1 | 35.2 | 1 |
| No | 57 | 39.1 | 1.45 (0.85-2.49) | 34.0 | 1.13 (0.56-2.27) |
| Number of CB units with haplotype B [VI] | | p = 0.45 | | p = 0.30 | |
| 2 CB units | 88 | 44.9 | 1 | 31.2 | 1 |
| 1 CB units | 14 | 42.9 | 0.961 (0.45-2.03) | 43.6 | 1.37 (0.18-10.15) |
| 0 CB units | 2 | 50.0 | 1.12 (0.09-16.27) | 50.0 | 2.12 (0.91-4.93) |

[I] The median age was 38 years (range 2-73)
[II] Six patients had Hodgkin disease, 4 had chronic lymphocytic leukemia and 12 had non-Hodgkin lymphoma
[III] Two patients had missing data
[IV] The identity of the dominant CB unit could not be ascertained in 14 cases
[V] The median value for the total nucleated cells infused was 4.1 × 10$^8$/kg, range (2.0 × 10$^8$/kg to 19.5 × 10$^8$/kg)
[VI] Six patients had missing data B. Validation cohort

| | | 1-year overall survival | | 1-year relapse Cumulative | |
|---|---|---|---|---|---|
| | n | Probability (%) | HR (95% CI) (risk of death) | incidence (%) | HR (95% CI) (risk of relapse) |
| Age [I] | | p = 0.09 | | p = 0.35 | |
| ≤40 yr | 44 | 55.0 | 1 | 21.1 | 1 |
| >40 yr | 50 | 31.1 | 1.27 (0.72-1.90) | 25.5 | 1.02 (0.45-2.30) |
| Sex | | p = 0.61 | | p = 0.19 | |
| Male | 54 | 40.0 | 1 | 19.5 | 1 |
| Female | 40 | 43.7 | 0.78 (.45-1.37) | 27.3 | 1.67 (0.77-3.61) |
| Diagnosis | | p = 0.51 | | p = 0.23 | |
| Acute myeloid leukemia | 39 | 43.6 | 1 | 33.3 | 1 |
| Acute lymphoblastic leukemia | 25 | 40.0 | 0.96 (0.50-18.5) | 40.1 | 1.27 (0.53-2.78) |
| Myelodysplastic syndromes | 5 | 80.0 | 0.26 (0.21-1.81) | 20.0 | 0.55 (0.07-4.20) |
| Lymphoproliferative disorder [II] | 16 | 37.5 | 1.19 (0.57-2.53) | 16.2 | 0.14 (0.2-1.18) |
| Chronic myeloid leukemia | 9 | 56.6 | 0.62 (.21-1.81) | 12.5 | 0.30 (0.04-2.32) |
| Disease status at transplant | | p = 0.04 | | p = 0.02 | |
| Complete remission | 52 | 48.9 | 1 | 17.8 | 1 |
| Refractory/relapsed disease | 42 | 34.2 | 1.47 (1.09-2.56) | 33.2 | 1.84 (1.13-4.22) |

TABLE 1-continued

Patient characteristics and outcomes in the discovery (n = 110) and validation (n = 94) cohorts.

| | | | | | |
|---|---|---|---|---|---|
| Conditioning regimen | | $p = 0.87$ | | $p = 0.65$ | |
| Myeloablative | 73 | 40.9 | 1 | 25.1 | 1 |
| Non-myeloablative | 21 | 47.4 | 1.09 (0.63-1.71) | 17.6 | 0.85 (0.42-1.88) |
| Graft | | $p = 0.73$ | | $p = 0.73$ | |
| Double cord | 88 | 40.5 | 1 | 31.9 | 1 |
| Single cord | 6 | 66.7 | 0.91 (0.50-1.68) | 16.7 | 0.84 (0.23-1.86) |
| CMV status [III] | | $p = 0.78$ | | $p = 0.44$ | |
| Seronegative | 16 | 42.9 | 1 | 43.2 | 1 |
| Seropositive | 76 | 42.3 | 0.99 (0.77-1.36) | 29.1 | 0.65 (0.20-1.91) |
| HLA match between recipient and dominant CB unit [IV] | | $p = 0.11$ | | $p = 0.26$ | |
| 7-8/8 | 10 | 75.1 | 1 | 20.1 | 1 |
| 5-6/8 | 31 | 36.8 | 1.61 (0.96-4.71) | 36.8 | 1.4 (0.84-2.33) |
| ≤4/8 | 43 | 38.2 | 1.79 (0.91-3.54) | 18.6 | 0.99 (0.70-1.24) |
| Total mononuclear cells infused [V] | | $p = 0.91$ | | $p = 0.73$ | |
| ≤3.8 × $10^8$/kg | | 42.9 | 1 | 26.8 | 1 |
| >3.8 × $10^8$/kg | | 39.0 | 0.97 (0.55-1.70) | 24.4 | 0.862 (0.37-2.03) |
| Patient HLA C group [VI, VII] | | $p = 0.002$ | | $p < 0.001$ | |
| C1/C1 | 38 | 50.0 | 1 | 22.2 | 1 |
| C1/C2 | 40 | 52.0 | 0.91 (0.47-1.76) | 18.1 | 0.83 (0.30-2.34) |
| C2/C2 | 16 | 12.5 | 2.73 (1.30-5.75) | 68.7 | 5.34 (1.96-14.50) |
| Patient HLA C group | | $p < 0.001$ | | $p < 0.001$ | |
| C1/x | 78 | 51.3 | 1 | 19.5 | 1 |
| C2/C2 | 16 | 12.5 | 2.90 (1.56-5.38) | 68.7 | 5.98 (2.73-13.10) |
| Patients receiving CB grafts with the combined HLA-C1-KIR2DL2/L3/S2 genotype | | $p = 0.07$ | | $p = 0.05$ | |
| Yes | 37 | 56.8 | 1 | 16.2 | 1 |
| No | 57 | 36.8 | 1.70 (0.94-3.07) | 35.7 | 2.38 (0.96-5.94) |
| HLA-C1/x patients receiving CB grafts with the combined HLA-C1-KIR2DL2/L3/S2 genotype | | $p = 0.02$ | | $p = 0.01$ | |
| Yes | 31 | 67.7 | 1 | 6.5 | 1 |
| No | 47 | 40.4 | 2.33 (1.13-4.81) | 28.3 | 5.02 (1.13-22.26) |
| HLA match between recipient and dominant CB unit [IV] | | $p = 0.11$ | | $p = 0.26$ | |
| 7-8/8 | 10 | 75.1 | 1 | 20.1 | 1 |
| 5-6/8 | 31 | 36.8 | 1.61 (0.96-4.71) | 36.8 | 1.4 (0.84-2.33) |
| ≤4/8 | 43 | 38.2 | 1.79 (0.91-3.54) | 18.6 | 0.99 (0.70-1.24) |
| Patients received CB grafts with the combined HLA-C2-KIR2DL1/S1 genotype | | $p = 0.54$ | | $p = 0.20$ | |
| Yes | 35 | 46.6 | 1 | 23.1 | 1 |
| No | 59 | 41.7 | 1.19 (0.68-2.07) | 34.1 | 1.31 (0.76-2.01) |

[I] Median age was 41.0 years (range 1-73)
[II] Five patients had chronic lymphocytic leukemia, 5 patients had Hodgkin's disease and 6 patients had non-Hodgkin's lymphoma
[III] Two patients had missing data
[IV] The identity of the dominant CB unit could not be ascertained in 10 cases
[V] The median value for the total of nucleated cells infused was 3.8 × $10^8$/kg, range (1.5 × $10^8$/kg-34.2 × $10^8$/kg)
[VI] The p values for the comparisons of outcomes in C1/C1 vs C2/C2 patients were $p = 0.007$ for OS and $p < 0.001$ for cumulative incidence of progression.
[VII] The p values for the comparisons of outcomes in C1/C2 vs C2/C2 patients were $p = 0.001$ for OS and $p < 0.001$ for cumulative incidence of progression.

Figure 4A:
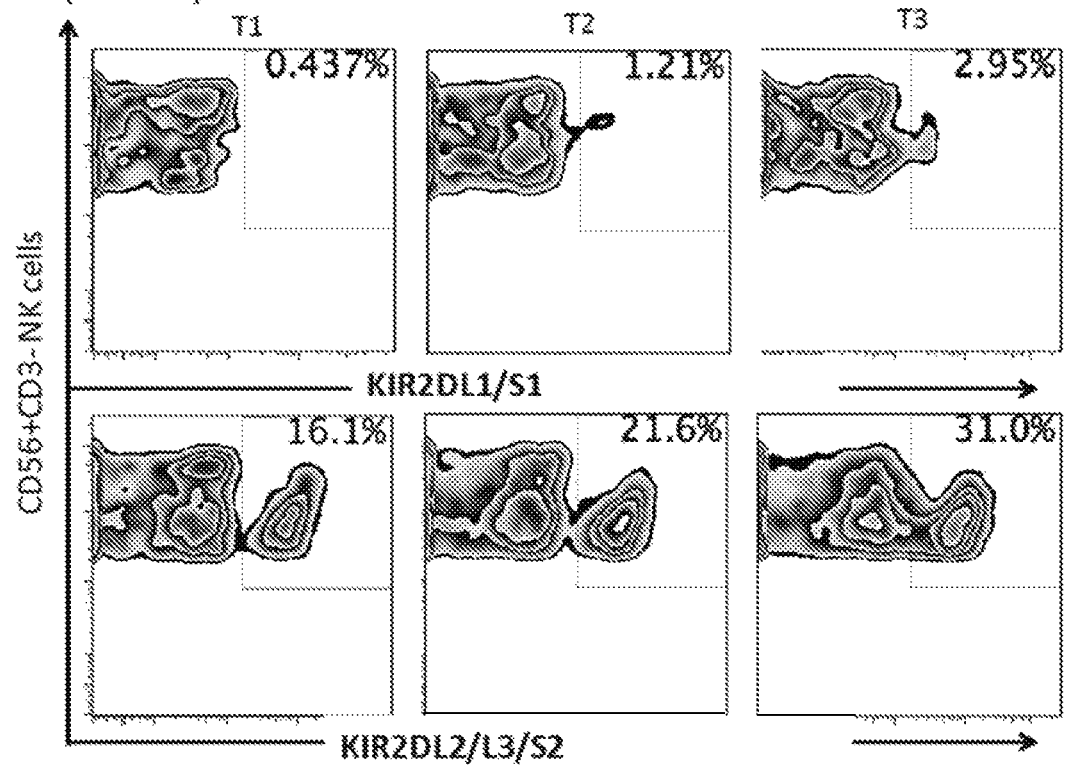
FIGS. 4A-4B: (A) Representative FACS plots of reconstituting KIR2DL1/S1 and KIR2DL2/L3/S2 expressing NK cells in PBMCs from 7 HLA-C1/C1, 9 HLA-C1/C2 and 4 HLA-C2/C2 patients collected at different post-CBT intervals (median times 50.0 [T1], 97.5 [T2] and 189.5 [T3] days). (B) Frequency of KIR2DL2/L3/S2 vs. KIR2DL1/S1 expressing NK cells at different time points post CBT. Box plots represent the first and third quartiles and lines inside the boxes the median values; whiskers extend to 1.5 times the interquartile range.
Figure 4B:
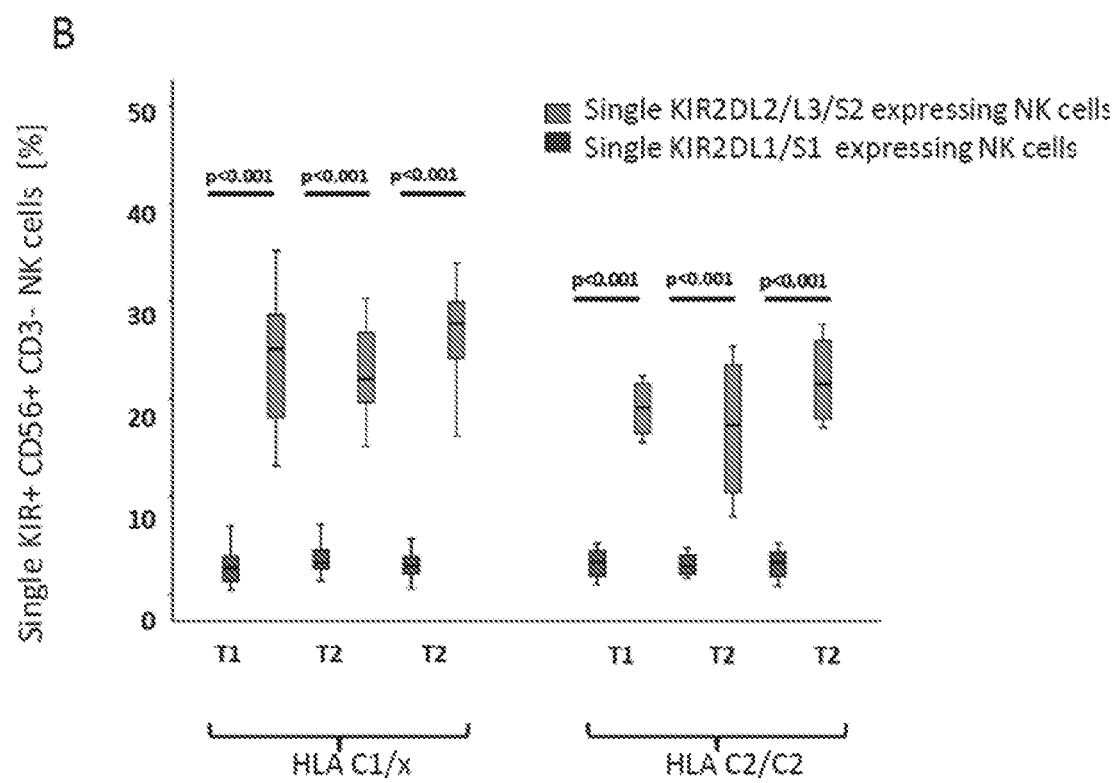
Figure 10A:
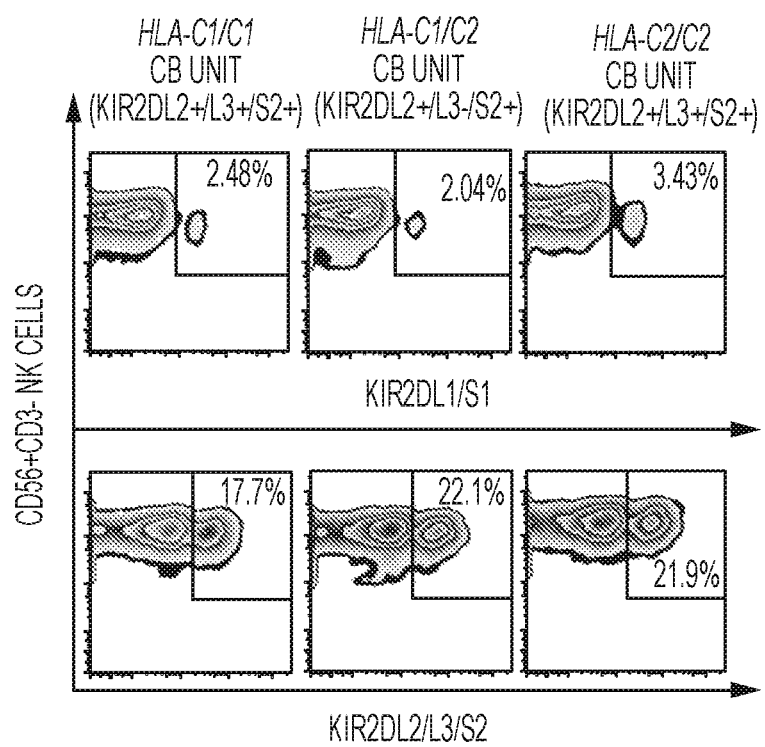
FIGS. 10A-10B: (A) Flow cytometric analysis of the phenotype of NK cells differentiated from CB-derived CD34+ hematopoietic progenitor cells. Examples from CB units with HLA-C1/C1, HLA-C1/C2 and HLA-C2/C2 genotype are presented. KIR2DL2/L3/S2 receptors emerge earlier and at a higher frequency on CD56+CD3− NK cells, irrespective of the cord HLA-C genotype. The KIR genotype of the CB units used for NK cell differentiation is included in parentheses above each FACS plot. (B) Comparison of the frequencies of KIR2DL1/S1 and KIR2DL2/L3/S2 expressing NK cells differentiated in vitro from CD34+ hematopoietic progenitor cells according to HLA-C genotype of the CB unit (n=8).
Figure 10B:
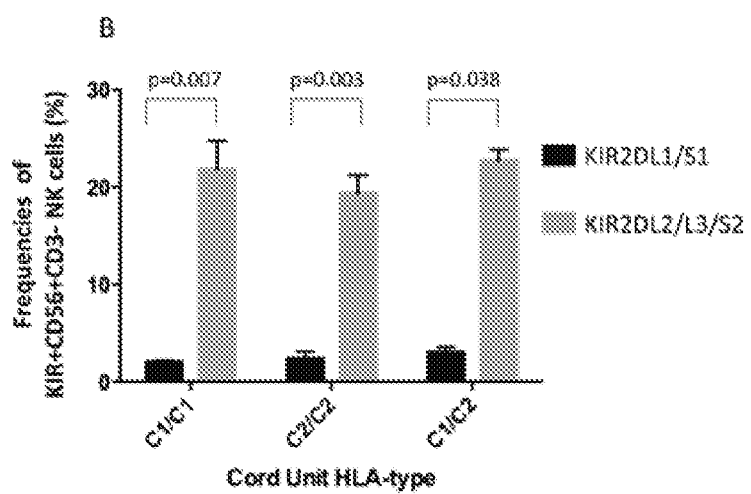

KIR2DL2/L3/S2-Expressing NK Cells Emerge as the Dominant NK Cell Subset after CBT Regardless of Recipient HLA-C Genotype:

To determine whether the effect of the HLA-C genotype on outcome is related to biased expression of HLA-C-specific KIRs during NK cell development, NK cells were differentiated from CB-derived CD34+ hematopoietic progenitors (n=8) in vitro and the order of MR acquisition was determined. HLA-C1-specific KIR2DL2/L3/S2-expressing NK cells appeared significantly earlier and in greater numbers than C2-specific KIR2DL1/S1-expressing cells, irrespective of the HLA-C or the KIR genotype of the CB units used for NK cell differentiation (FIG. 10). Using 14-color multiparameter flow cytometry, MR expression was then studied on single cells in peripheral blood samples from 20 patients at three post-CBT intervals. As shown in FIGS. 4A-B, KIR2DL2/L3/S2-expressing NK cells dominated the NK cell repertoire, regardless of the recipient's HLA-C group. These findings supported the in vitro model favoring the generation of C1-specific NK cells early after CBT.

TABLE 2

Classification of patients into HLA-C1 and C2 groups based on HLA type

| HLA-C1 group | HLA-C2 group |
|---|---|
| C*01 | C*01: 14 |
| C*02: 27/65 | C*02 |
| C*3 | C*3: 07/10/15/29/45/163 |
| C*04: 11/29/36/55/114 | C*04 |
| C*05: 20 | C*05 |
| C*06: 11/82 | C*06 |
| C*07 | C*07: 07/09/76/315/328 |
| C*08 | C*08: 10 |
| C*12: 02/03 . . . | C*12: 04/05/09/21/33/41/60/72 |
| C*14 | C*14: 12/49 |

TABLE 2-continued

Classification of patients into HLA-C1 and C2 groups based on HLA type

| HLA-C1 group | HLA-C2 group |
| --- | --- |
| C*15: 07/25/43 | C*15 |
| C*16: 01/04+ | C*16: 02/09/12/19/25/37/46-48/60 |
| C*17: 22 | C*17 |
| | C*18 |

TABLE 3

Effect of recipient HLA-C genotype on clinical outcome after CBT according to type of malignancy (discovery cohort).

| | N | 1-year risk of death HR (95% CI) | 1-year relapse risk HR (95% CI) |
| --- | --- | --- | --- |
| Lymphoid | | p = 0.002 | p = 0.002 |
| HLA-C1/x | 37 | 1 | 1 |
| HLA-C2-C2 | 9 | 4.14 (1.72-9.97) | 8.37 (2.19-31.91) |
| Myeloid | | p = 0.002 | p = 0.01 |
| HLA-C1/x | 49 | 1 | 1 |
| HLA-C2-C2 | 15 | 3.14 (1.55-6.37) | 2.93 (1.24-6.93) |

Figure 5A:
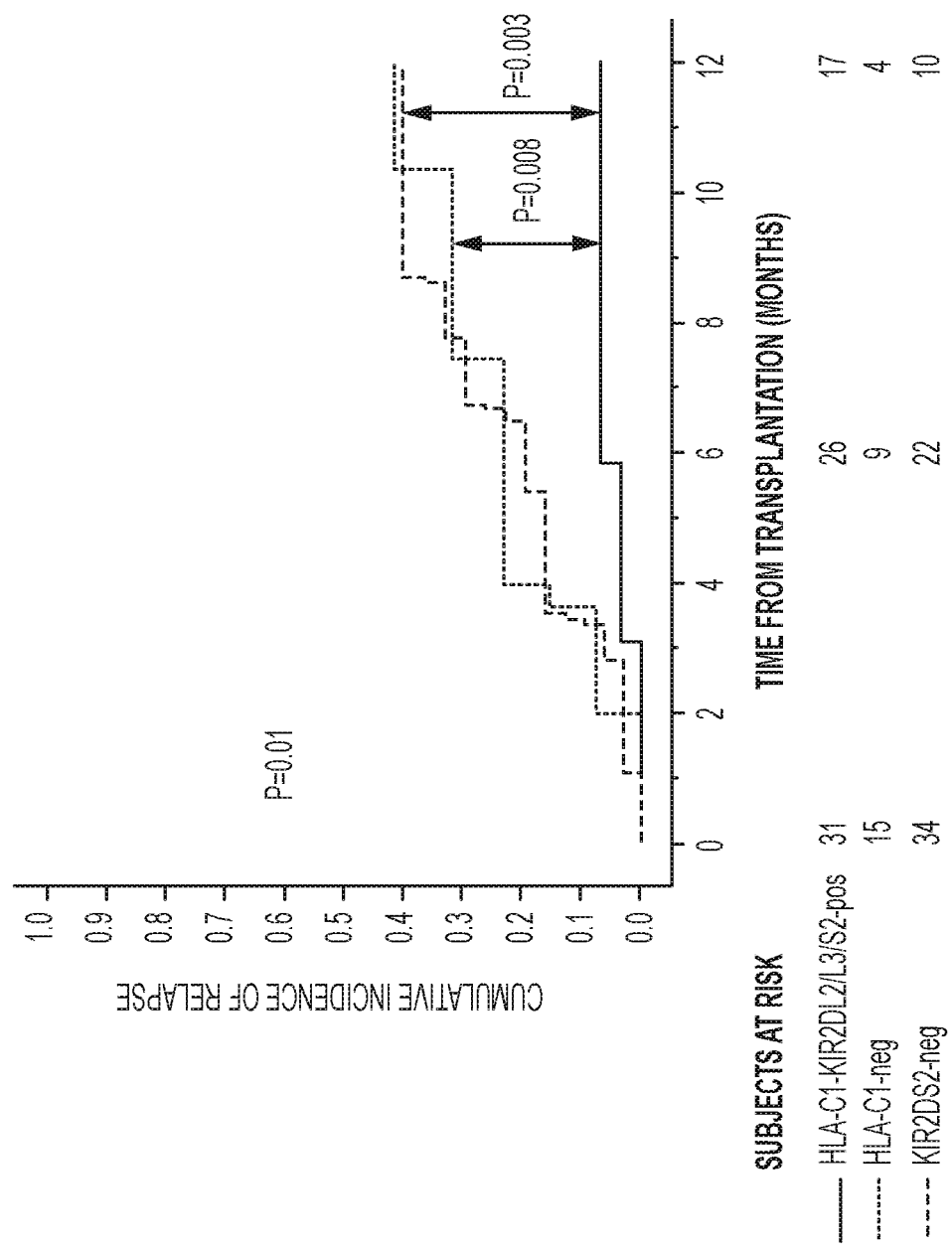
FIGS. 5A-5B: One-year cumulative incidence of relapse and probability of OS in the 80 HLA-C1/x patients grouped according to the KIR-HLA genotype of the donor CB graft. The 31 HLA-C1/x patients receiving at least one CB unit with the HLA-C1-KIR2DL2/L3/S2 have a significantly lower incidence of relapse (A) and better OS (B) compared to the 15 patients receiving CB grafts that were predicted to be unlicensed (HLA-C1-negative) and to the 34 patients receiving KIR2DS2-negative grafts. Tick marks on the lines indicate censored patients.
Figure 5B:
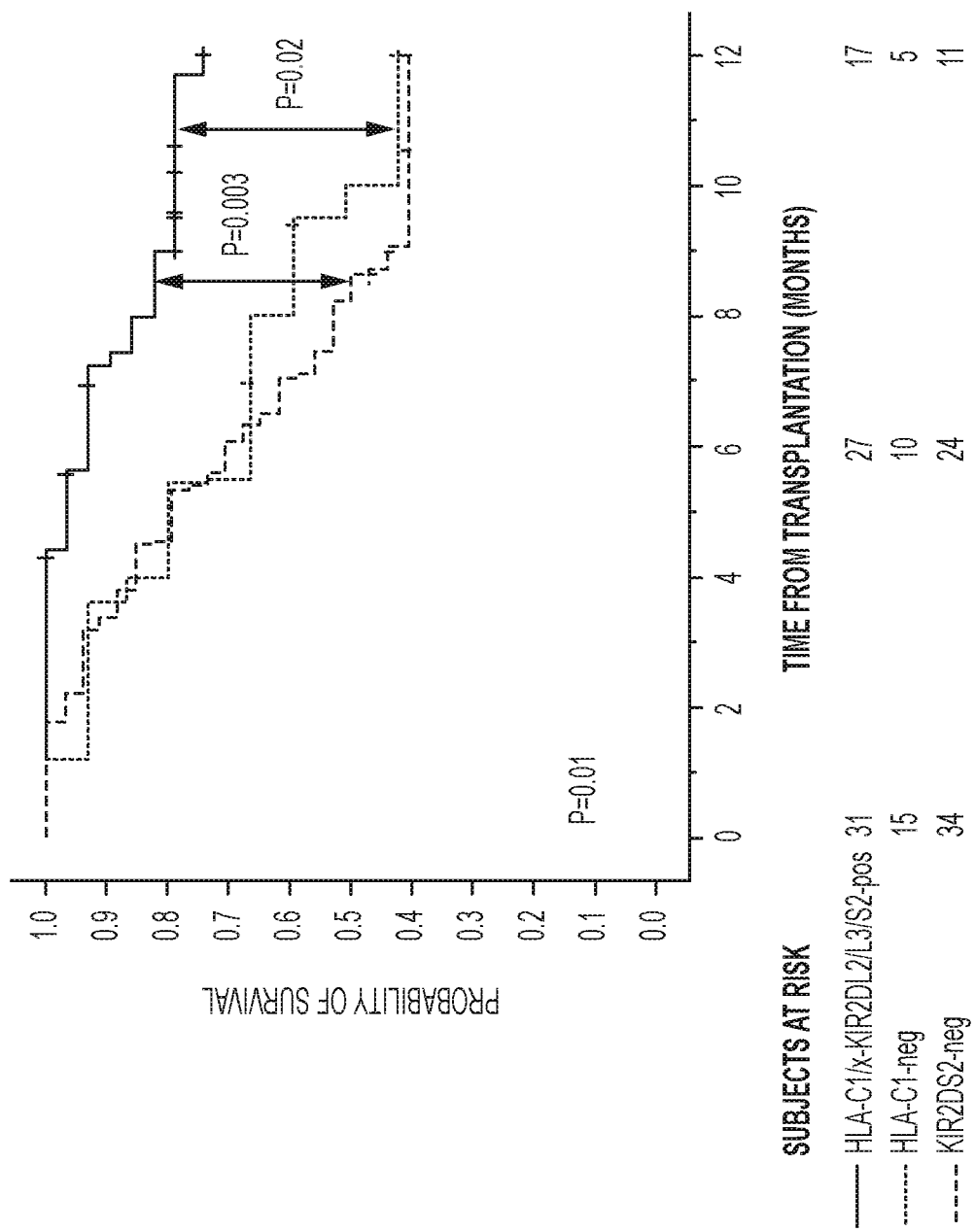

Combined HLA-C1-KIR2DL2/L3 and KIR2DS2 genotype in the CB graft is associated with a lower risk of relapse and superior OS in HLA-C1/x CBT recipients: Licensed NK cells are functionally more responsive to their targets (Kim et al., 2005). It was therefore hypothesized that protection from relapse in HLA-C1/x (HLA-C1/C1 or HLA-C1/C2) recipients would be improved if the donor NK cells are predicted to be licensed for KIR2DL2 or KIR2DL3 (i.e.; HLA-C1 positive) and the activating KIR2DS2 is present (combined genotype KIR2DL2 or KIR2DL3 positive [or both] and KIR2DS2 positive, referred to as KIR2DL2/L3/S2 herein). To test this hypothesis, the outcome of CBT was analyzed in the 80 HLA-C1/x patients in the discovery cohort. The 34 patients who received units with the genotype HLA-C1-KIR2DL2/L3 but lacking KIR2DS2 and the 15 patients who received HLA-C1-negative (unlicensed) grafts had a significantly higher relapse rate and a worse OS than the 31 patients receiving at least one CB unit with the combined donor genotype of HLA-C1-KIR2DL2/L3/S2. The hazard ratios (HR) for relapse were HR=7.04 (CI 1.57-31.47, p=0.002) and HR=6.87 (CI 1.33-35.37, p=0.01) respectively. The HR for OS were HR=3.46 (CI 1.46-8.20, p=0.005) and HR=3.00 (CI 1.109-8.431; p=0.03) respectively. FIG. 5 shows the plots for the 1 year cumulative incidence of relapse and probability of OS. TRM rates among the three groups were similar. Since patients who received KIR2DS2-negative or unlicensed grafts had a similar outcome, they were combined them into a single cohort for the remainder of the analysis. These 49 patients had a higher risk of relapse (HR=6.98, CI 1.61-30.25; p=0.002) and a worse OS, (HR=3.31, CI 1.45-7.50; p=0.003) than the 31 who received HLA-C1-KIR2DL2/L3/S2 grafts (Table 1). There was no impact of either donor HLA-C or KIR2DL2/L3/S2 alone, or indeed other hapolotype B defining genes on outcomes after CBT (Table 4).

TABLE 4

Donor characteristics and outcomes in the discovery cohort.

| | 1-year relapse risk HR, (95% CI) | 1-year risk of death HR, (95% CI) |
| --- | --- | --- |
| Donor HLA C group | p = 0.45 | p = 0.66 |
| Both units C1/C1 | 1 | 1 |
| At least one unit C1/C2 | 0.98 (0.46-1.21) | 0.89 (0.51-1.30) |
| Both units C2/C2 | 1.28 (0.95-1.93) | 1.11 (0.46-1.45) |
| At least one unit positive for KIR2DS2 | 0.87 (0.63-2.32), p = 0.23 | 0.91 (0.51-2.17) p = 0.31 |
| At least one unit positive for KIR2DL2 | 1.01 (0.34-15.63) p = 0.97 | 1.02 (0.09-31.44) p = 0.95 |
| At least one unit positive for KIR2DL3 | 0.98 (0.20-116.39) p = 1.0 | 0.97 (0.15-148.22), p = 1.0 |
| At least one unit positive for KIRL2/L3/S2 | 0.77 (0.32-2.46), p = 0.14 | 0.84 (0.37-1.81) p = 0.19 |
| At least one unit positive for KIR2DS1 | 1.11 (0.83-1.63) p = 0.44 | 1.09 (0.85-2.01) p = 0.67 |
| At least one unit positive for KIR2DS3 | 0.91 (0.60-1.23) p = 0.89 | 0.99 (0.76-1.41) p = 0.98 |
| At least one unit positive for KIR2DS5 | 1.02 (0.85-1.76), p = 0.38 | 1.12 (0.86-1.84) p = 0.51 |
| At least one unit positive for KIR3DS1 | 1.09 (0.77-1.62) p = 0.69 | 1.01 (0.95-1.20) p = 0.98 |

These findings were confirmed in the 78 HLA-C1/x CBT recipients of the validation cohort. The 47 patients who received KIR2DS2-negative or unlicensed grafts had a higher risk of relapse (HR=5.02, CI 1.13-22.26; p=0.01) and a worse OS (HR=2.33, CI 1.13-4.81; p=0.02) than the 31 who received a HLA-C1-KIR2DL2/L3/S2 graft (Table 1B).

Combined Donor HLA-C2-KIR2DL1 and KIR2DS1 Genotype May Improve Outcome in HLA-C2 Homozygous CBT Recipients:

Based on the above results, it was reasoned that HLA-C2 homozygous patients would have a better outcome if they received a CB unit predicted to be licensed for KIR2DL1 (HLA-C2/x) and positive for KIR2DS1. Because of the relatively small number of HLA-C2 homozygous patients in the series, the discovery and validation cohorts were combined to address this question.

Figure 6A:
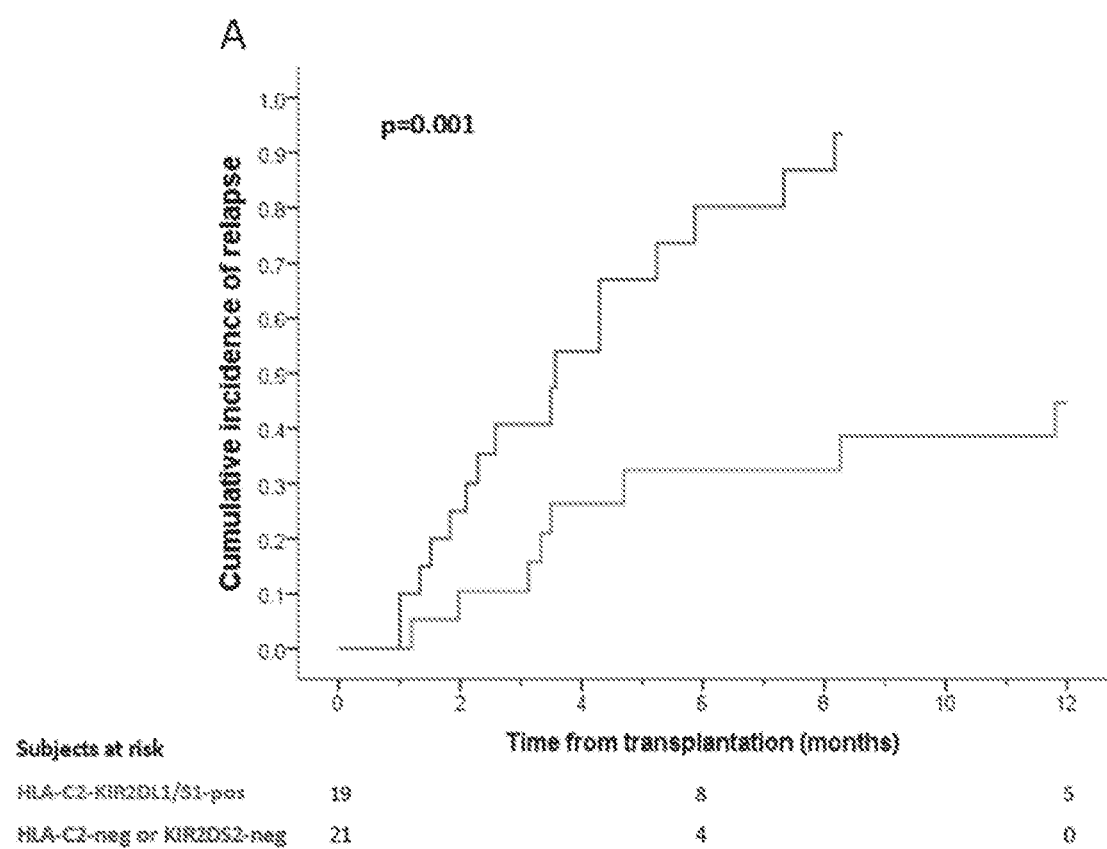
FIGS. 6A-6B: HLA-C2 homozygous patients receiving a CB graft with the combined HLA-C2-KIR2DL1/S1 genotype have a lower 1-year cumulative incidence of relapse and better probability of OS. We combined HLA-C2 homozygous patients in the discovery and validation cohorts (n=40) for this analysis. The 19 HLA-C1/x patients receiving at least one CB unit with the combined HLA-C2-KIR2DL1/S1 genotype have a significantly lower incidence of relapse (A) and a better OS (B) compared to the 21 patients receiving CB grafts that were either KIR2DS1-negative or predicted to be unlicensed (HLA-C2-negative). Tick marks on the lines indicate censored patients.
Figure 6B:
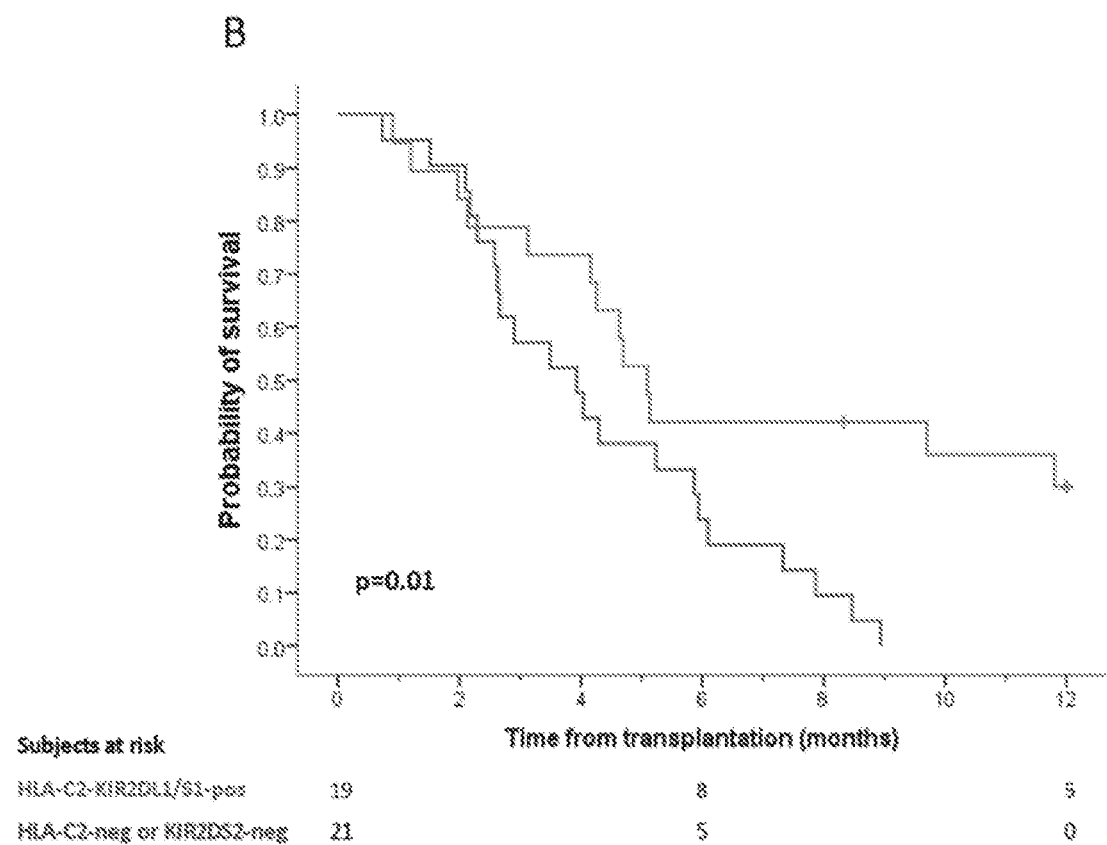

The 21 of the 40 HLA-C2 homozygous patients who received grafts that were either HLA-C2-negative or KIR2DS1-negative had a significantly higher relapse rate (HR=4.21, CI 1.67-10.61; p=0.002) and worse OS (HR=2.48, CI 1.18-5.25; p=0.01) than the 19 patients who received at least one CB unit possessing the combined genotype of HLA-C2-KIR2DL1 and KIR2DS1. FIG. 6A-B shows the curves for the 1-year cumulative incidence of relapse and probability of OS. There was no protective effect identified for the donor HLA-C1-KIR2DL2/L3/S2 genotype on outcome in HLA-C2 homozygous recipients (FIG. 9).

The Combined HLA-KIR Genotype of the Dominant CB Graft Determines Outcome after Double CBT:

In double cord HSCT, one CB unit becomes dominant as the main source of hematopoiesis (Saliba et al., 2015). A 6-month landmark analysis was performed to examine the influence of the dominant CB unit's KIR-HLA genotype on outcome. The 25 HLA-C1/x patients, in whom the dominant unit was negative for HLA-C1/x or KIR2DS2, had a significantly greater risk of relapse (HR=5.05, CI 1.15-30.99; p=0.03) and a trend towards worse OS (HR=2.50, CI 0.89-36.51; p=0.08) than the 23 HLA-C1/x patients in whom the dominant unit was positive for the combined genotype of HLA-C1-KIR2DL2/L3/S2. By 6 months the majority of HLA-C2 homozygous patient had relapsed, preventing any further analysis of this subset.

Combined HLA-C1-KIR2DL2/L3/S2 genotype in the CB graft, recipient HLA-C2 homozygosity and disease status at transplant are major factors associated with outcome: To identify key contributors to outcome, a multivariate analysis was performed that included the variables emerging from the univariate analysis (Table 1). Active disease at transplantation, recipient HLA-C2 homozygosity and not receiving a graft with a HLA-C1-KIR2DL2/L3/S2 genotype were the only independent predictors of relapse and OS. The influence of HLA-C1-KIR2DL2/L3/S2 was only observed in HLA-C1/x patients. Briefly, receiving a graft lacking the HLA-C1-KIR2DL2/L3/S2 genotype had a significant impact on relapse (HR=6.27, CI 1.44-17.29; p=0.01) and OS, (HR=3.06, 95% CI 1.32-7.09, p=0.009) in HLA-C1/x patients but did not influence relapse (HR=0.87, CI 0.41-1.84; p=0.72) or OS (HR=0.66 CI 0.17-3.11; p=0.84) in HLA-C2 homozygous patients (FIG. 9).

Figure 7A:
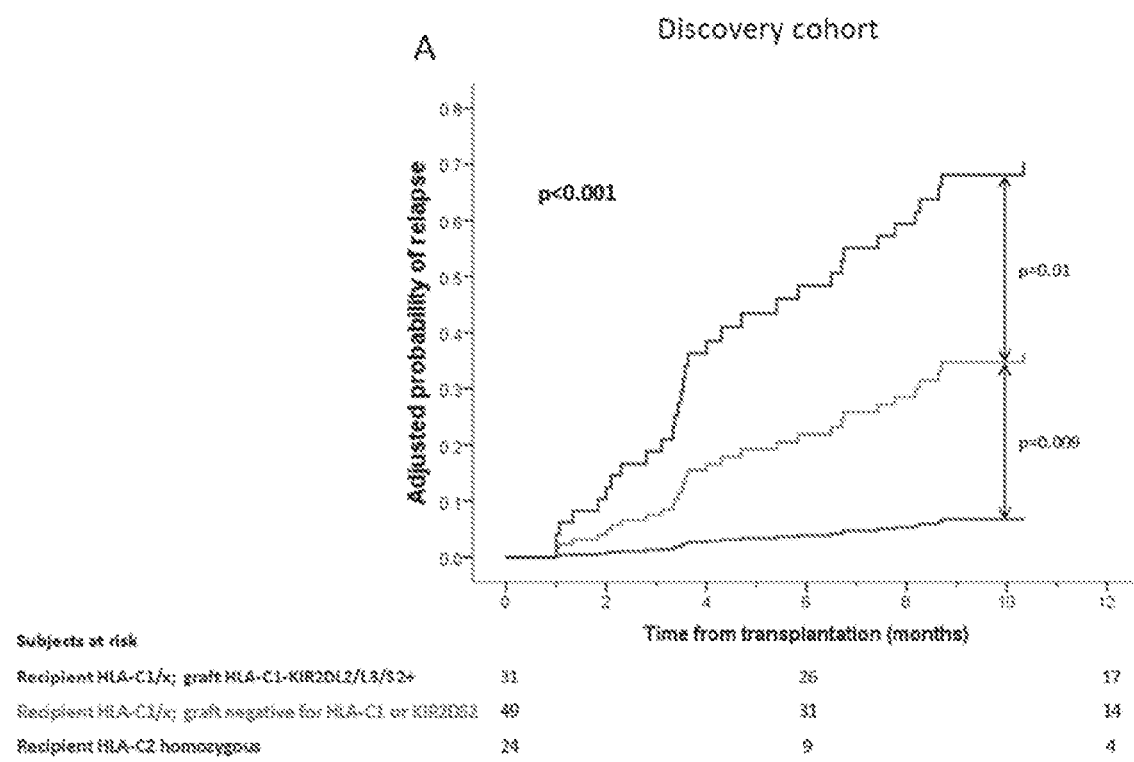
FIGS. 7A-7H: Adjusted (A, B and C, D) and unadjusted (E, F and G, H) 1-year probabilities of relapse and OS in the discovery vs. validation cohorts according to HLA and MR genotype. Patients in each cohort were classified into three categories: HLA-C1/x receiving an HLA-C1-KIR2DL2/L3/S2 graft, HLA-C1/x receiving an HLA-C1-KIR2DL2/L3/S2 graft and HLA-C2 homozygous patients.
Figure 7B:
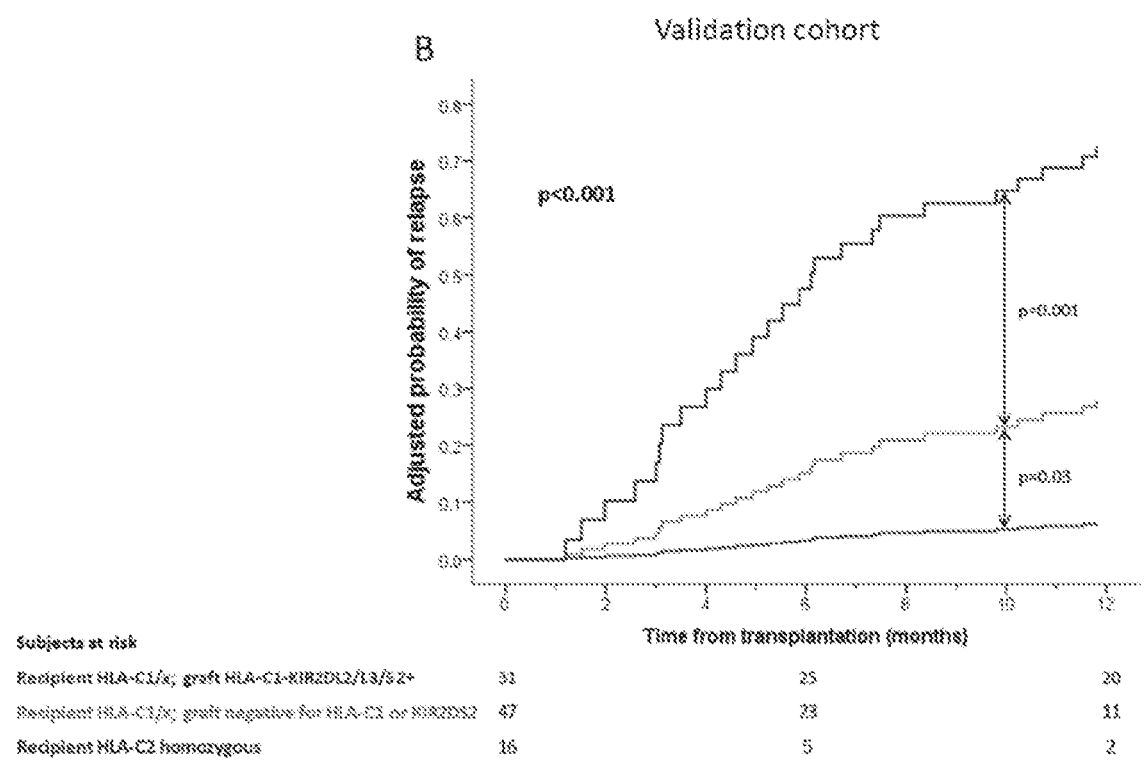
Figure 7C:
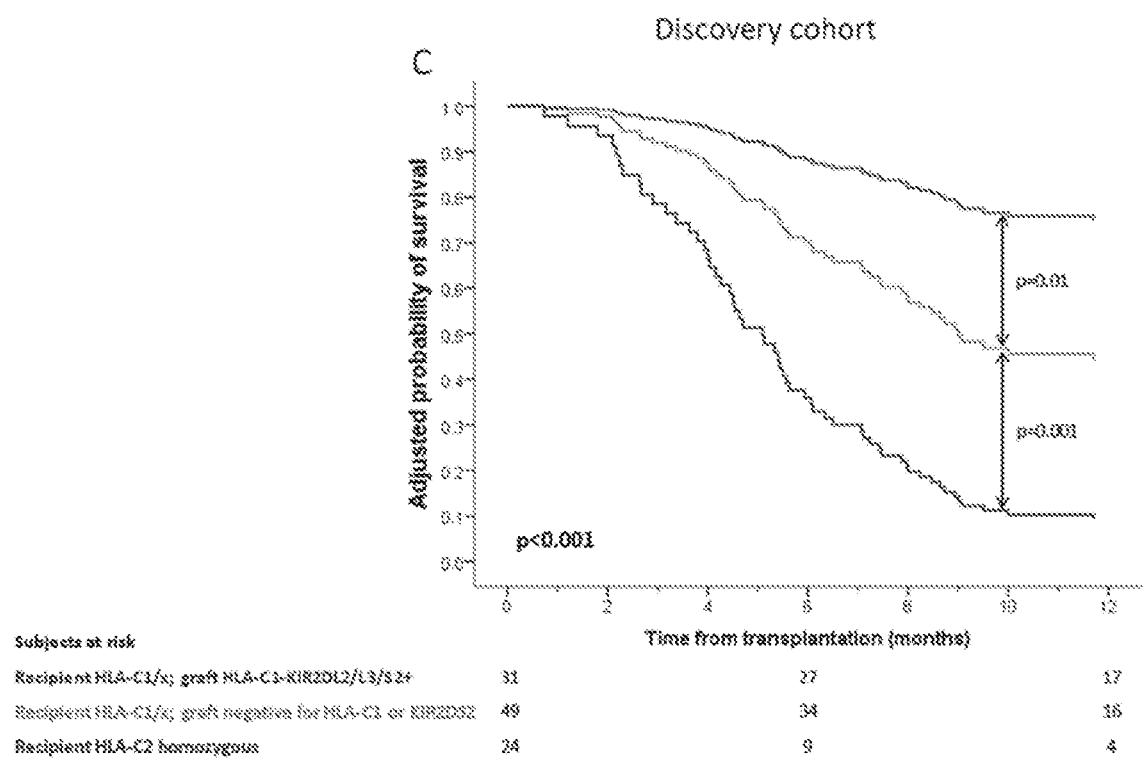
Figure 7D:
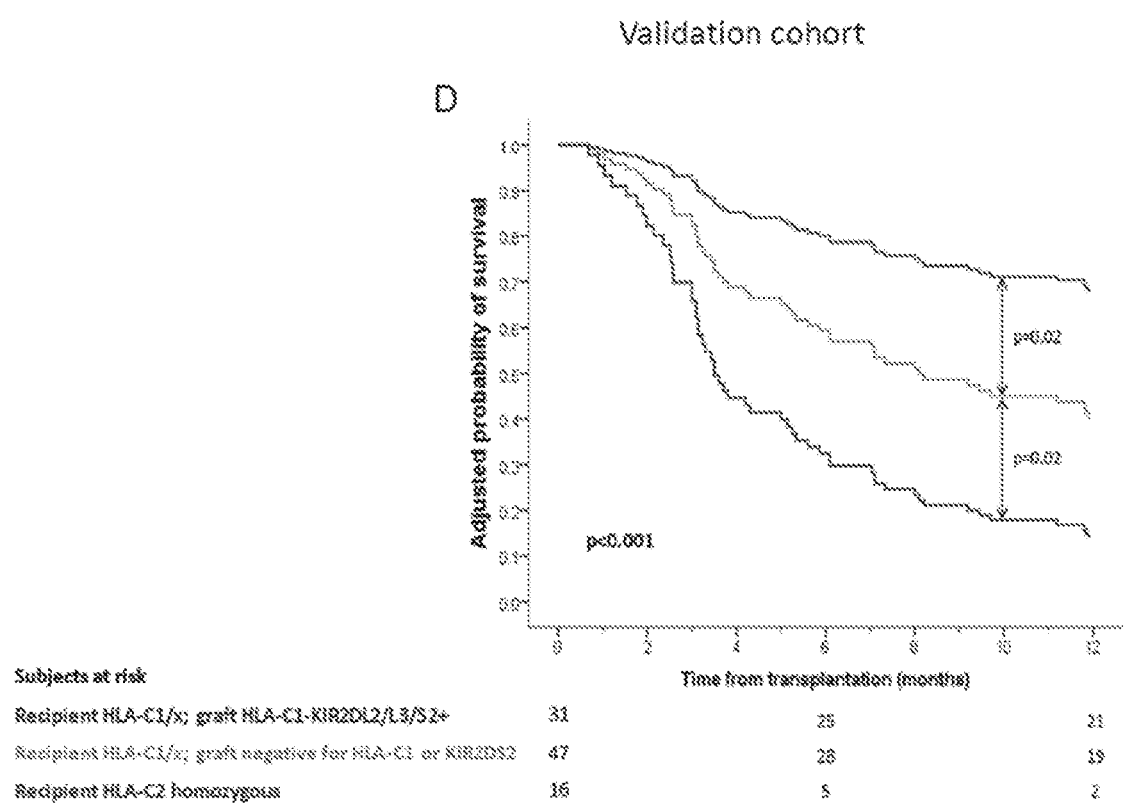
Figure 7E:
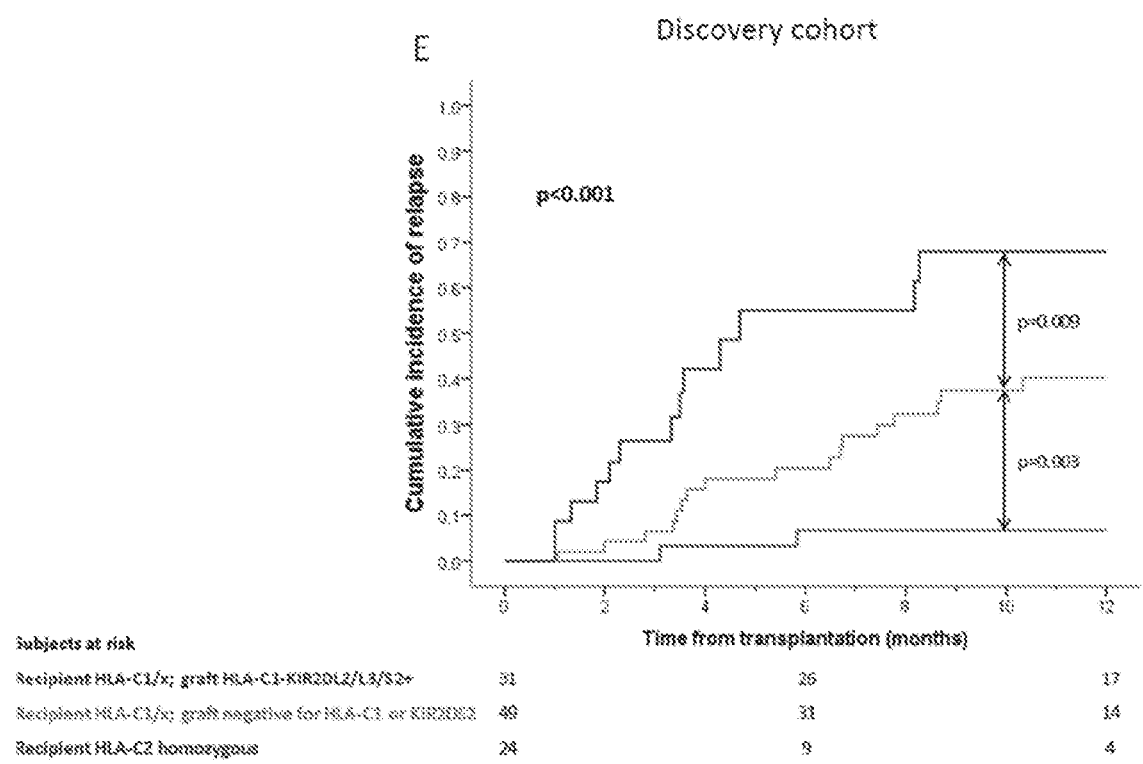
Figure 7F:
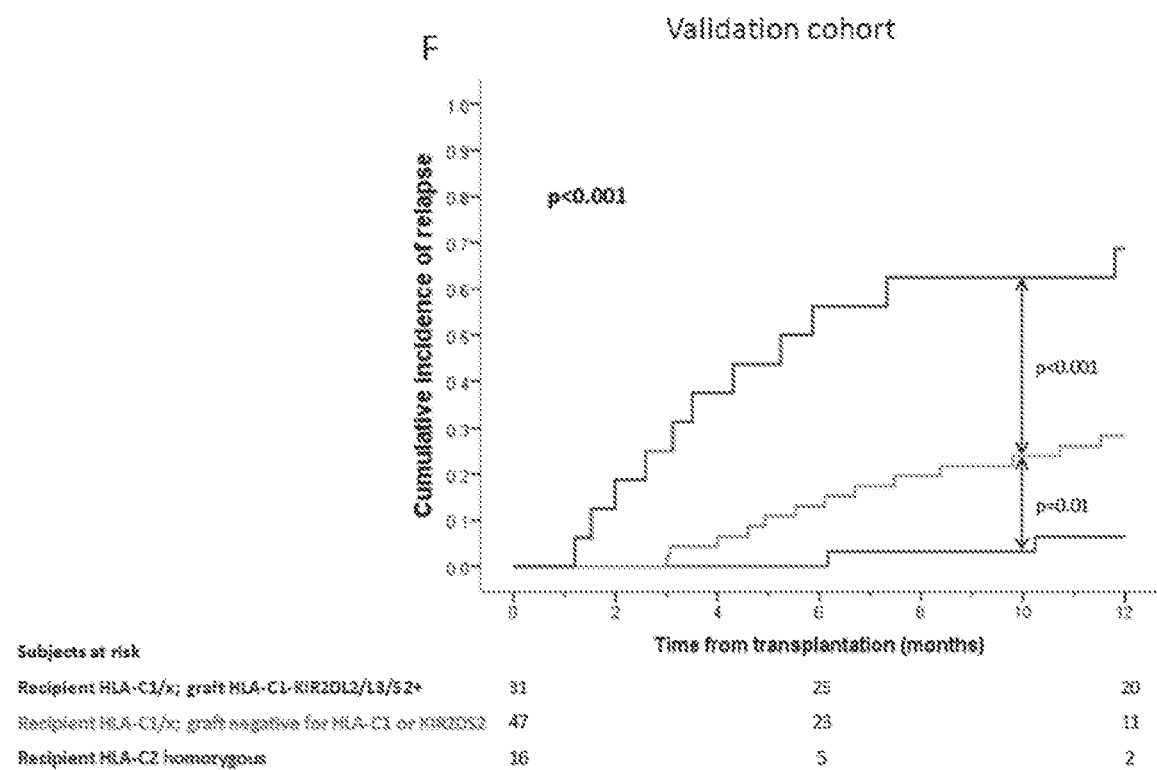
Figure 7G:
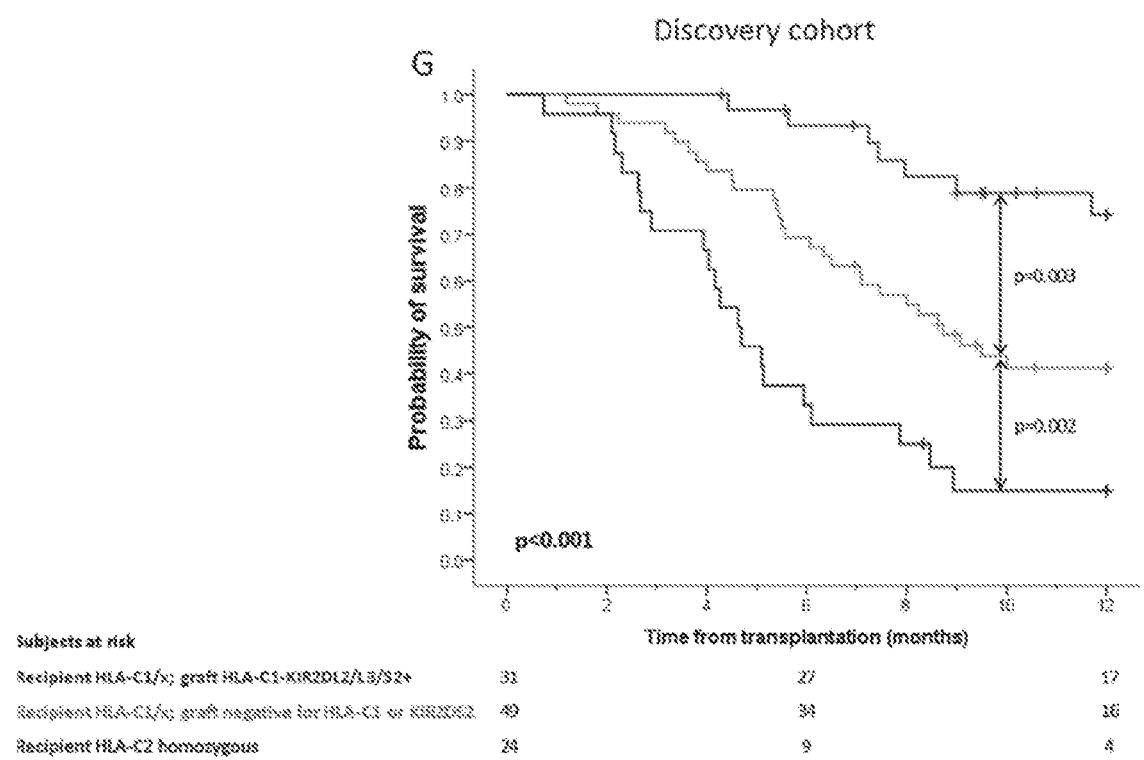
Figure 7H:
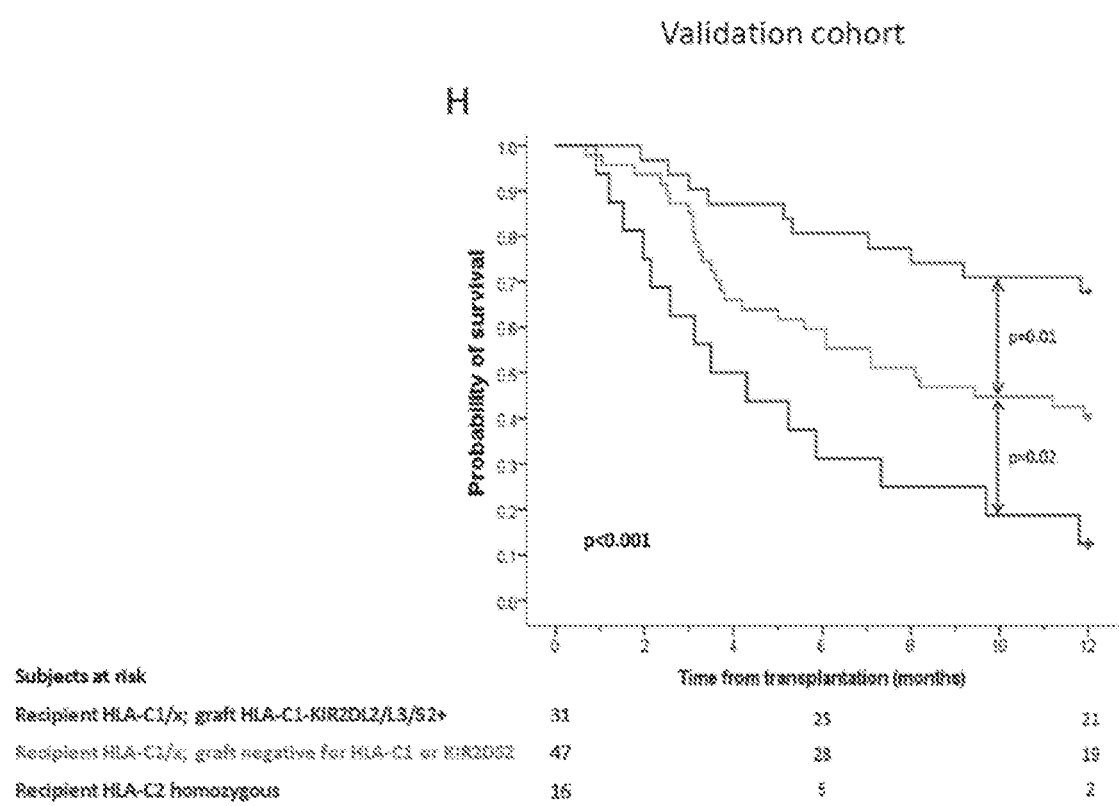

As the influence of HLA-C1-KIR2DL2/L3/S2 on both outcomes was only observed in HLA-C1/x individuals, patients were classified into three categories that were associated with distinct outcomes: HLA-C1/x patients who received an HLA-C1-KIR2DL2/L3/S2 graft, HLA-C1/x patients who did not receive an HLA-C1-KIR2DL2/L3/S2 graft and HLA-C2 homozygous patients. The adjusted hazard ratios for relapse for the 49 HLA-C1/x patients who did not receive an HLA-C1-KIR2DL2/L3/S2 graft and the 24 HLA-C2 homozygous patients compared to the 31 HLA-C1/x patients who received an HLA-C1-KIR2DL2/L3/S2 graft were 6.18 (CI 1.42-21.85; p=0.01) and 16.55 (CI 3.69-74.21; p<0.001) respectively. Similarly the adjusted hazard ratios for OS were 2.85 (CI 1.22-6.63; p=0.01) and 8.21 (CI 3.44-19.60; p<0.001) respectively. The adjusted HRs for relapse and OS of the 24 HLA-C2 homozygous patients compared to the 49 HLA-C1/x patients who did not receive an HLA-C1-KIR2DL2/L3/S2 graft were 2.68 (CI 1.28-5.59, p=0.009) and 2.88 (CI 1.57-5.30, p=0.001) respectively. Patients with relapsed/refractory disease at CBT had a higher risk of relapse and a worse OS: adjusted HR 2.34 (CI 1.14-4.75; p=0.02) and adjusted HR 1.60 (1.09-2.79; p=0.04), respectively. These relationships are shown graphically in FIGS. 7A, C, E, and G together with side-by-side confirmation from analysis of the validation cohort (FIGS. 7B, D, F, and H).

The clinical characteristics of patients were similar whether stratified by their HLA-C group (Table 5) or their CB graft HLA-KIR genotype (Table 6).

TABLE 5

Patient characteristics according to recipient HLA-C genotype (n = 110).

| | HLA-C1/C1 n (%) | HLA-C1/C2 n (%) | HLA-C2/C2 n (%) | P |
|---|---|---|---|---|
| Age | | | | 0.11 |
| ≤40 yr | 20 (60.6) | 23 (43.4) | 16 (66.7) | |
| >40 yr | 13 (39.4) | 30 (56.6) | 8 (15.7) | |
| Sex | | | | 0.44 |
| Male | 17 (51.5) | 20 (37.7) | 11 (45.8) | |
| Female | 16 (48.5) | 33 (62.3) | 13 (54.2) | |
| Diagnosis [I] | | | | 0.48 |
| ALL | 7 (21.2) | 13 (24.5) | 4 (16.7) | |
| AML | 13 (39.4) | 20 (37.7) | 11 (45.8) | |
| MDS | 9 (27.3) | 6 (11.3) | 4 (16.7) | |
| Others | 4 (12.1) | 14 (26.4) | 5 (20.8) | |
| Disease status at transplant | | | | 0.60 |
| Complete remission | 22 (66.7) | 32 (60.4) | 13 (54.2) | |
| Active disease | 11 (33.3) | 21 (39.6) | 11 (45.8) | |
| Conditioning regimen | | | | 1.0 |
| Myeloablative | 24 (72.7) | 38 (71.7) | 17 (70.8) | |
| Non-myeloablative | 9 (27.3) | 15 (28.3) | 7 (29.2) | |
| Graft | | | | 0.85 |
| Single cord | 31 (93.9) | 51 (96.2) | 23 (95.8) | |
| Double cord | 2 (6.1) | 2 (3.8) | 1 (4.2) | |
| Patient CMV status [II] | | | | 0.92 |
| Seronegative | 4 (12.5) | 5 (9.4) | 2 (8.7) | |
| Seropositive | 28 (85.5) | 48 (90.6) | 21 (91.3) | |
| HLA match between recipient and dominant CB unit [III] | | | | 0.55 |
| ≤4/6 | 12 (40.0) | 19 (41.7) | 9 (45.0) | |
| 5/6 | 16 (53.3) | 18 (39.1) | 9 (45.0) | |
| 6/6 | 2 (6.7) | 9 (16.6) | 2 (10.0) | |

[I] ALL, acute lymphoblastic leukemia; AML, acute myeloid leukemia; MDS, myelodysplastic syndromes.
[II] Two patients had missing data
[III] In 14 cases it was not possible to establish the origin of the dominant unit

TABLE 6

Patient characteristics according to HLA-KIR genotype of the CB graft (n = 104). Patients were stratified based on whether or not they received a CB unit with the combined HLA-C1-KIR2DL2/L3/S2 genotype.

| | HLA-C1-KIR2DL2/L3/S2 positive CB graft n (%) | HLA-C1-KIR2DL2/L3/S2 negative CB graft n (%) | P |
|---|---|---|---|
| Age | | | 0.83 |
| ≤40 yr | 21 (56.8) | 36 (53.7) | |
| >40 yr | 16 (43.2) | 31 (46.3) | |
| Sex | | | 0.54 |
| Male | 15 (40.5) | 32 (47.8) | |
| Female | 22 (59.5) | 35 (52.2) | |
| Diagnosis [I] | | | 0.38 |
| ALL | 10 (27.0) | 13 (19.4) | |
| AML | 13 (35.2) | 26 (38.8) | |
| MDS | 4 (10.8) | 15 (22.4) | |
| Others | 10 (27.0) | 13 (19.5) | |
| Disease status at transplant | | | 1.0 |
| Complete remission | 22 (40.5) | 41 (31.2) | |
| Refractory/Relapsed | 15 (40.5) | 26 (38.8) | |
| Conditioning regimen | | | 0.81 |
| Myeloablative | 26 (70.3) | 49 (73.1) | |
| Non-myeloablative | 11 (29.7) | 18 (26.9) | |
| Graft | | | 1.0 |
| Single cord | 2 (5.4) | 3 (4.5) | |
| Double cord | 35 (94.6) | 64 (95.5) | |
| Patient CMV status [II] | | | 0.74 |
| Seronegative | 3 (8.3) | 8 (11.9) | |
| Seropositive | 33 (91.7) | 58 (86.6) | |
| HLA match between recipient and dominant CB unit [III] | | | 0.22 |
| ≤4/6 | 17 (48.6) | 23 (38.4) | |
| 5/6 | 16 (45.7) | 26 (43.3) | |
| 6/6 | 2 (5.7) | 11 (18.3) | |
| Patient HLA-C group[3] | | | 0.49 |
| C1/C1 | 11 (29.7) | 17 (25.4) | |
| C1/C2 | 20 (54.1) | 32 (47.8) | |
| C2/C2 | 6 (16.2) | 18 (26.9) | |

Figure 8A:
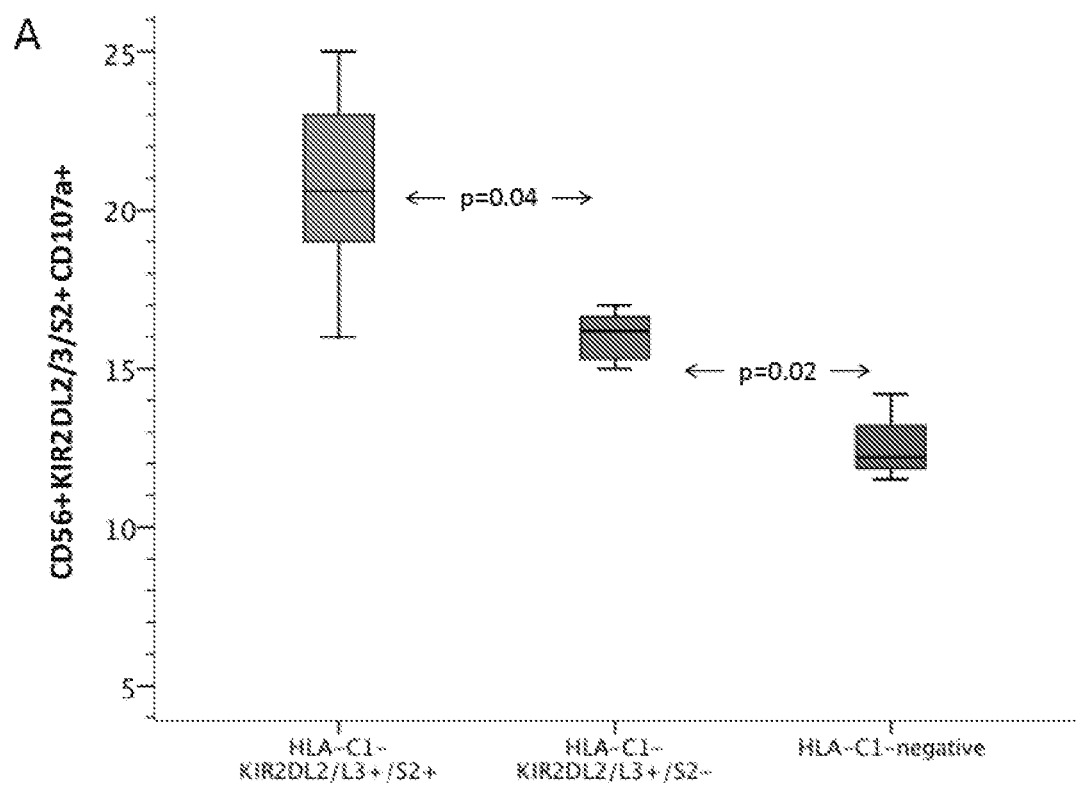
FIGS. 8A-8B: Box plots showing that recovering NK cells from CB units with a combined HLA-C1-KIR2DL2/L3/2DS2 genotype express more CD107a (A) and IFN-γ (B) in response to stimulation with K562 targets than those from CB units that were either predicted to be unlicensed (HLA-C1 negative) or were KIR2DS2 negative.
Figure 8B:
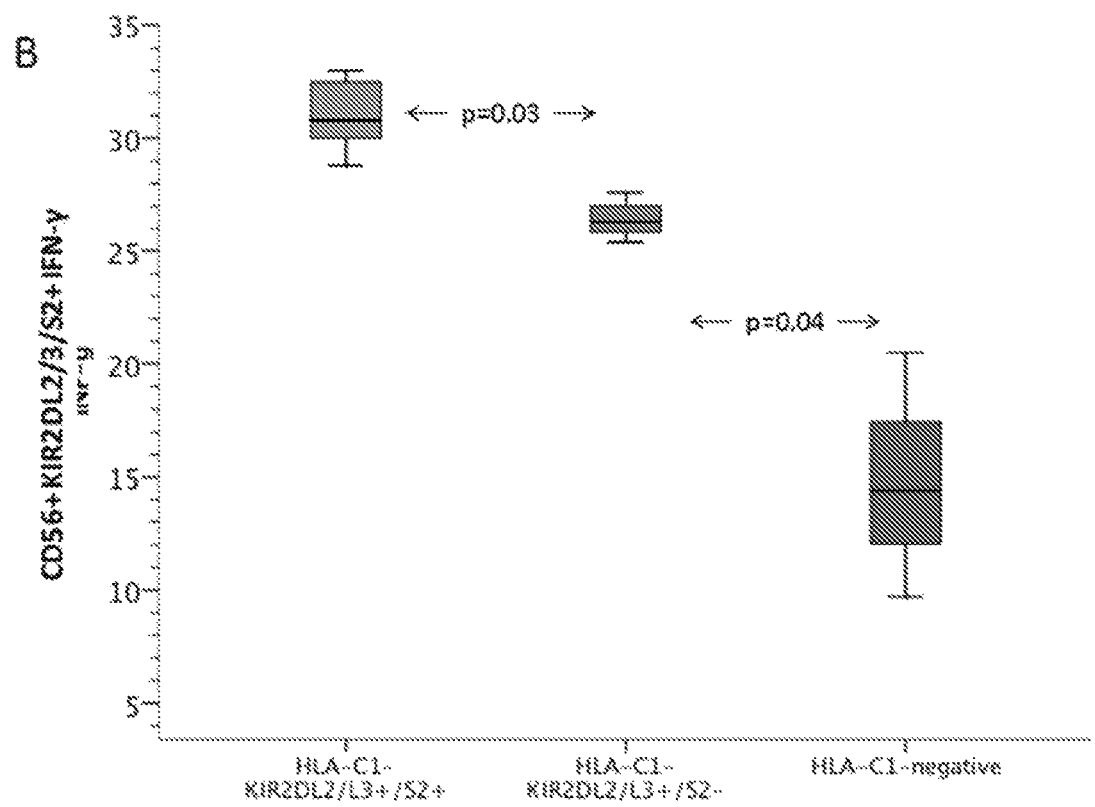
Figure 9A:
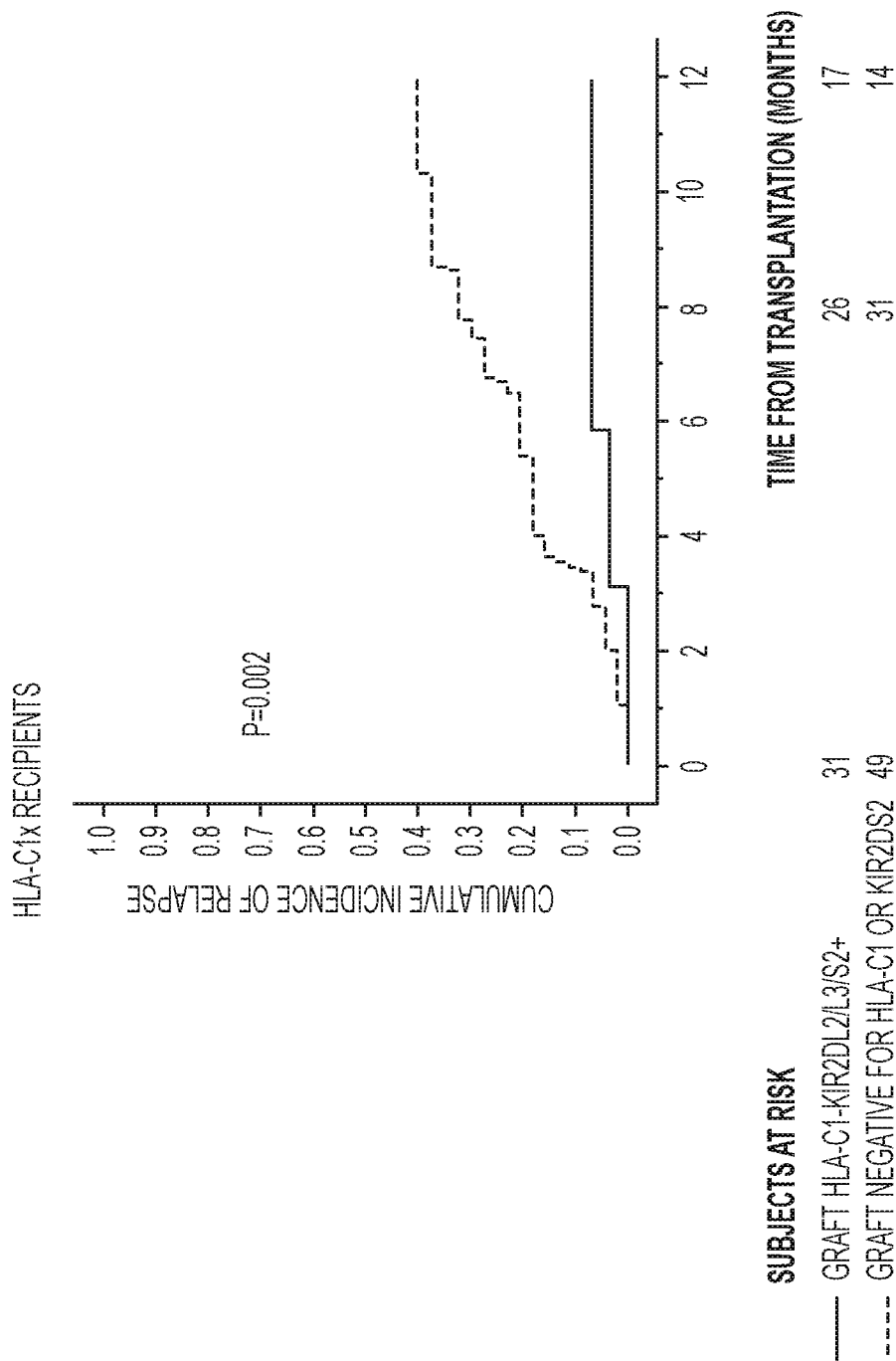
FIGS. 9A-9D: Impact of graft HLA-C1-KIR2DL2/L3/S2 genotype on outcome in HLA-C1/x and HLA-C2 homozygous patients (discovery cohort). The 31 HLA-C1/x patients who received a graft with the HLA-C1-KIR2DL2/L3/S2 genotype had significantly lower cumulative incidence of relapse (A) and better OS (C) than the 49 HLA-C1/x patients who received grafts without this specific genotype. This effect was not observed in the 24 HLA-C2 homozygous recipients (B and D).
Figure 9B:
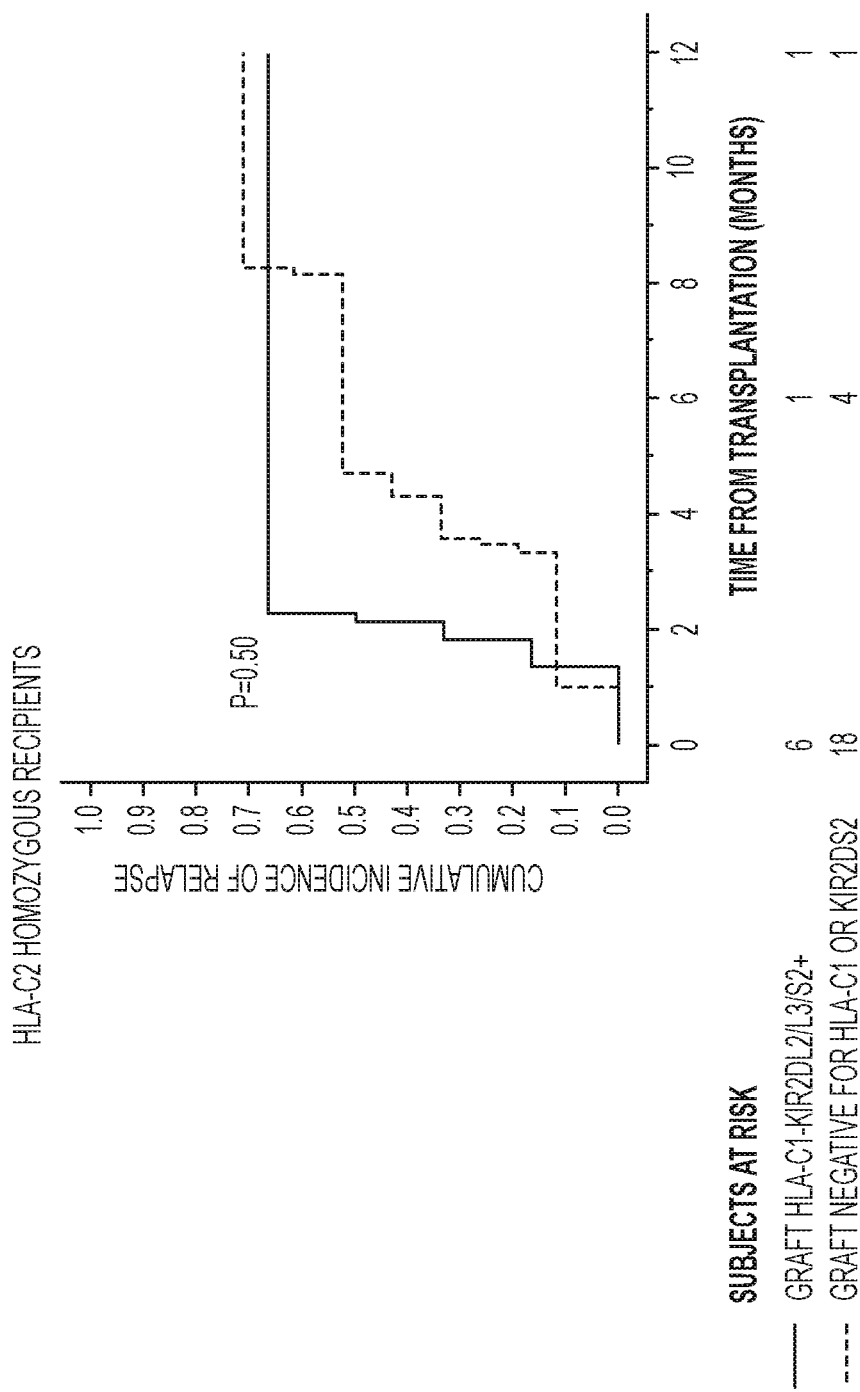
Figure 9C:
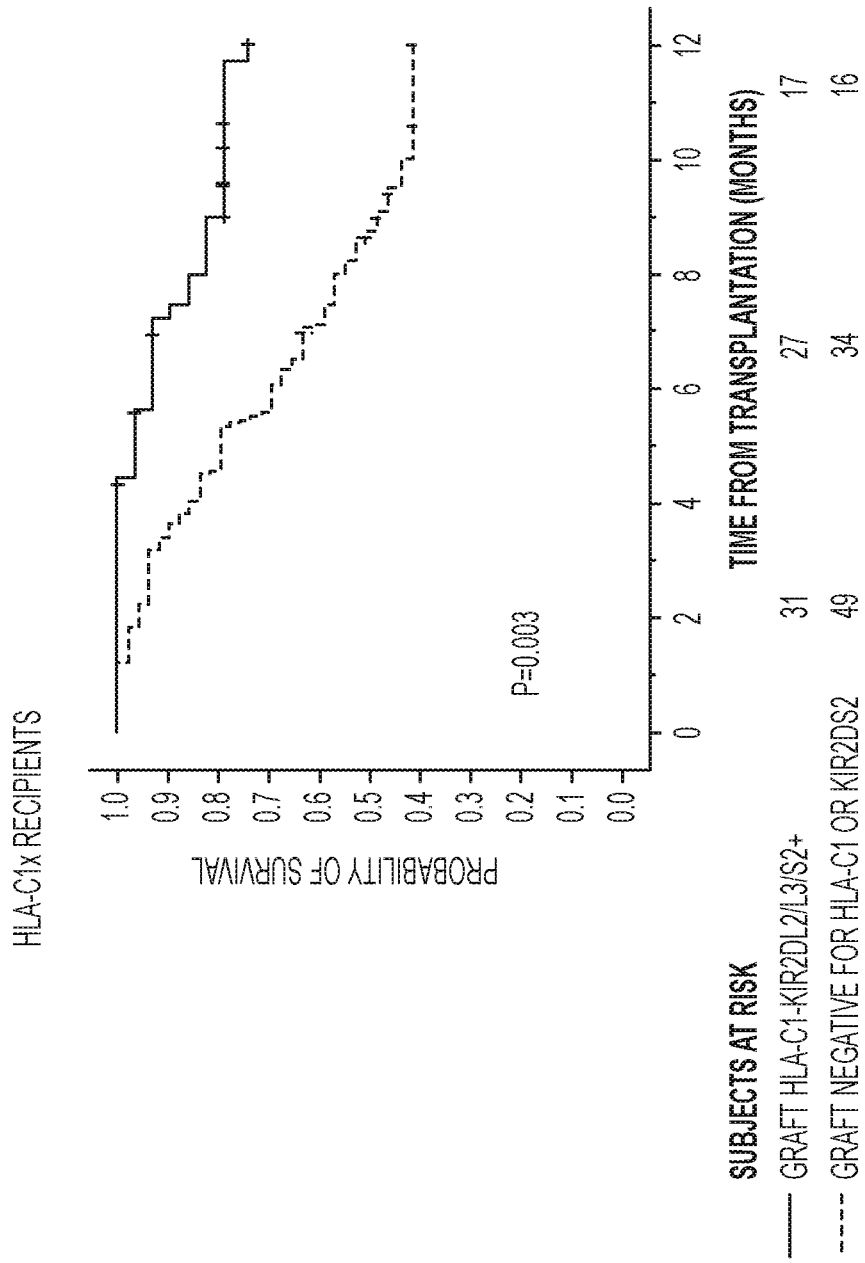
Figure 9D:
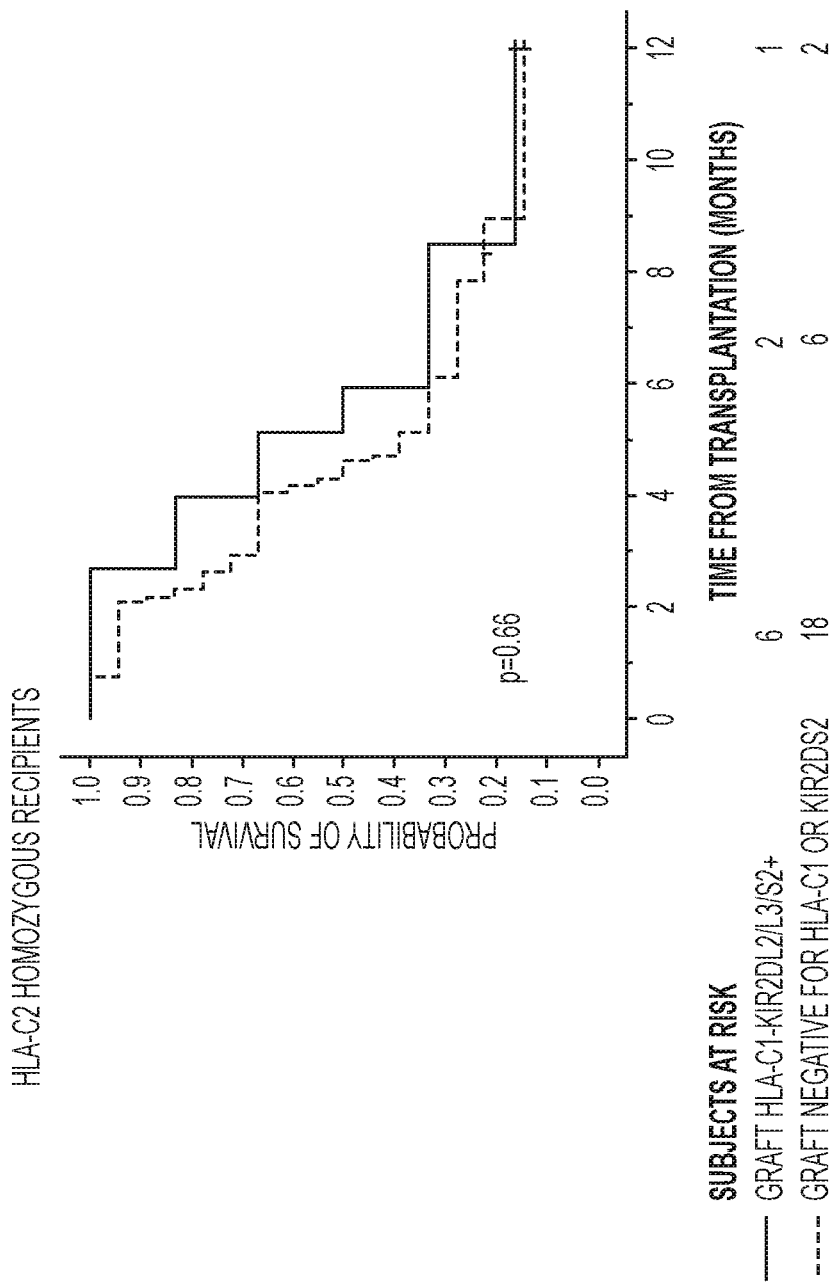
Figure 11A:
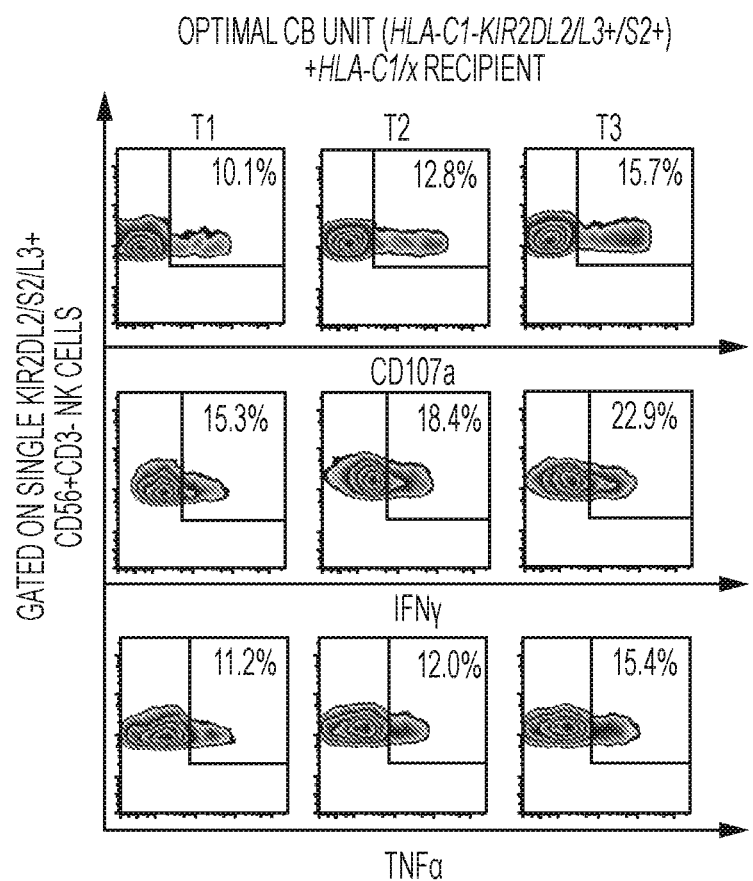
FIGS. 11A-11C: Representative FACS plots, showing that recovering NK cells from CB units with a combined HLA-C1-KIR2DL2/L3/2DS2 genotype possess enhanced effector function (A) compared to CB units that were either predicted to be unlicensed (HLA-C1 negative) (B) or were KIR2DS2 negative (C).
Figure 11C:
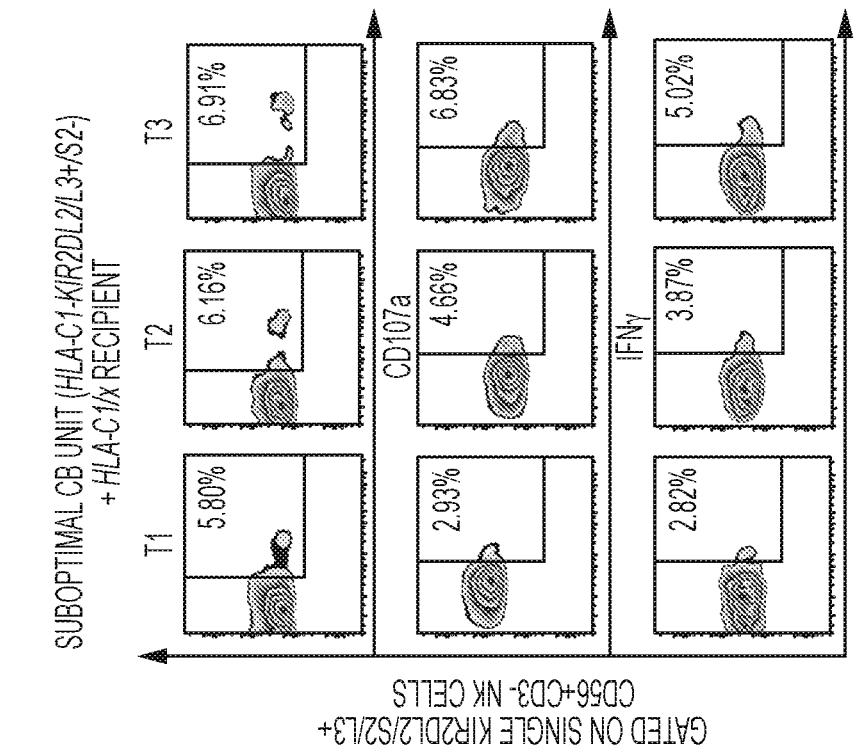
Figure 11B:
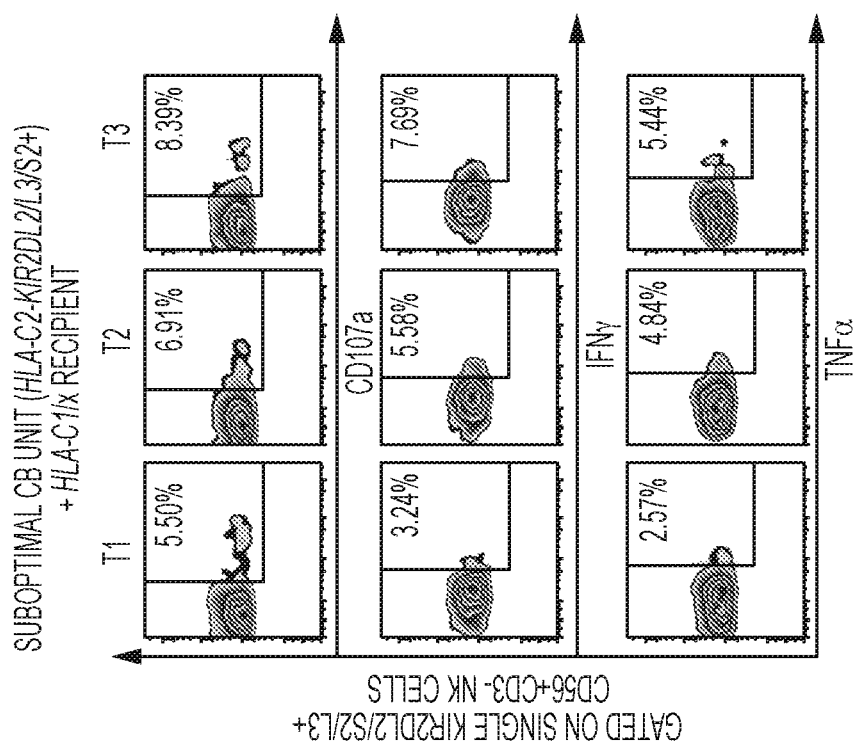
Figure 12A:
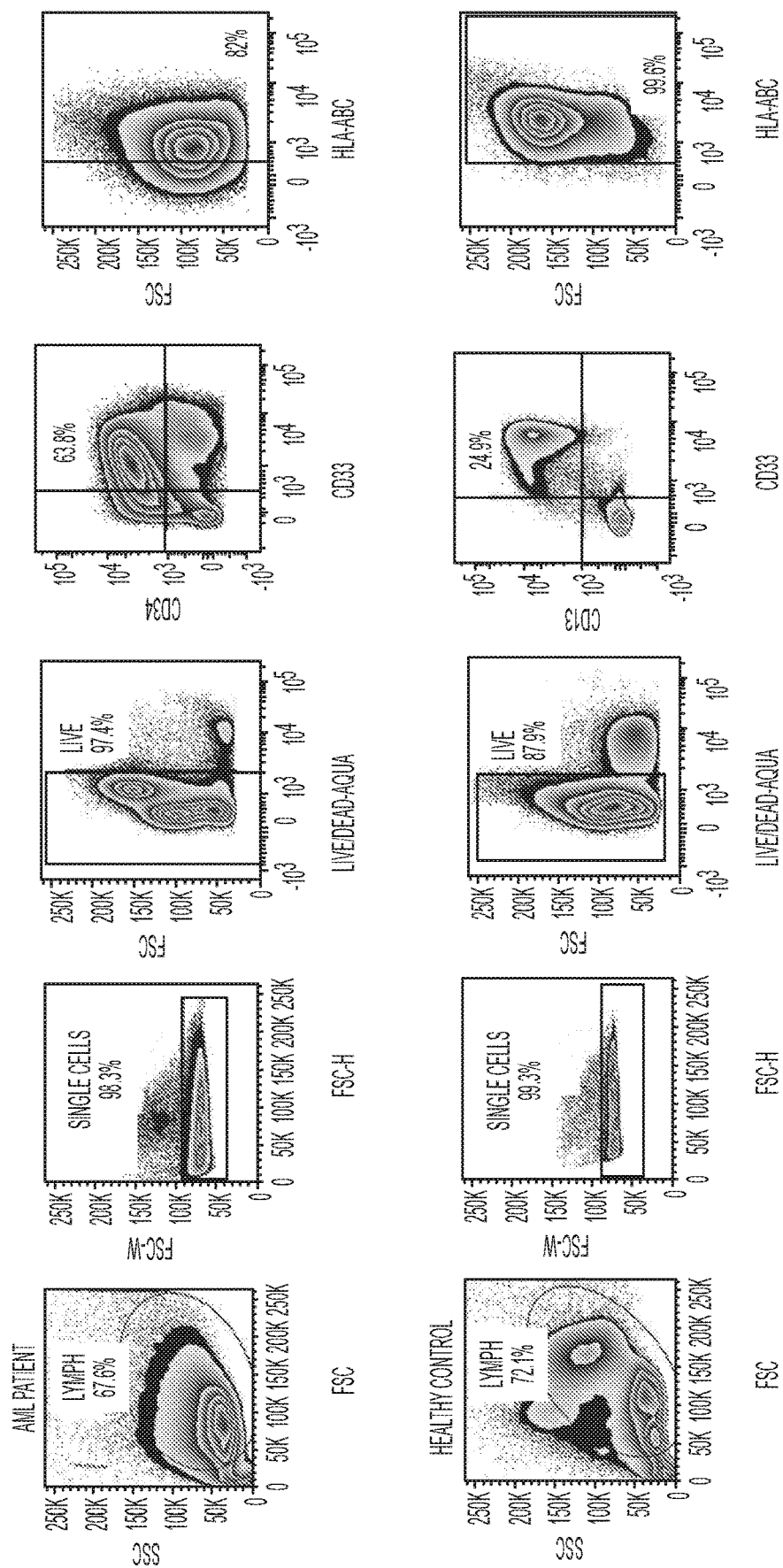
FIGS. 12A-12B: HLA class I molecules are downregulated on the surface of leukemic blasts. (A) Gating strategy is presented for the phenotyping of AML blasts and healthy control myeloid cells. Cells are gated on the myeloid lineage based on co-expression of CD13 and CD33. CD34 coexpression is included for AML blasts. (B) We analyzed HLA class I expression on the surface of myeloid cells for 10 healthy controls and 10 AML patient samples collected at diagnosis. The HLA class I expression per cell, measured by MFI (mean fluorescence intensity), is significantly lower on the surface of AML blasts compared to healthy control myeloid lineage cells. Box plots represent the first and third quartiles and lines inside boxes the median values; whiskers extend to 1.5 times the interquartile range.
Figure 12B:
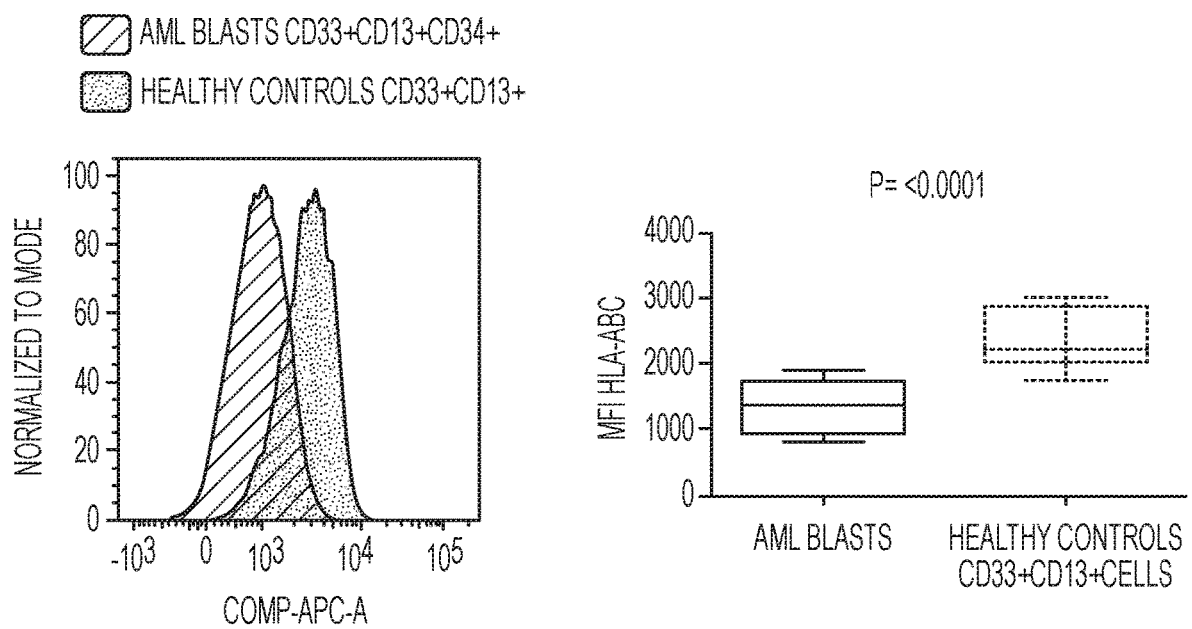

[I] ALL, acute lymphoblastic leukemia; AML, acute myeloid leukemia; MDS, myelodysplastic syndromes.
[II] Two patients had missing data
[III] In 9 cases it was not possible to establish the origin of the dominant unit KIR2DL2/L3/S2-expressing NK cells reconstituting from CB units with the combined HLA-C1-KIR2L2/L3/S2 genotype possess enhanced effector function in HLA-C1/x recipients: It was hypothesized that NK cells from an HLA-C1-KIR2DL2/L3/S2 CB unit are more effective in preventing relapse in HLA-C1/x recipients because they have enhanced effector function. This idea was tested by analyzing NK effector function in 27 samples from HLA-C1/x patients in the first 100 days post-CBT. The median frequency of CD107+ KIR2DL2/L3/S2+ NK cells in the 9 samples from HLA-C1-KIR2DL2/L3/S2 CB recipients was 20.6% (range 16-25%), compared to 16.2% (range 13-17%; p=0.041) in the 15 samples from recipients of HLA-C1-KIR2DL2/L3-positive but KIR2DS2-negative grafts, and to 12.2% (11.5-14.2%; p=0.018) for the 3 samples from recipients of unlicensed (HLA-C1-negative) units. Similar results were obtained when we examined the interferon-gamma response in the three groups: 30.8% (range 28.8-33.0%) compared to 26.3% (range 25.4-27.6%; p=0.029) and to 14.4% (range 9.7-20.5%; p=0.036) respectively, (FIG. 8 and FIG. 11).

The study assessed the impact of NK licensing and activating KIRs in combination with functional measures of NK reconstitution after CBT, using an independent cohort to validate results. It was found that patients with an HLA-C1/C1 or HLA-C1/C2 genotype have a significantly lower relapse rate and higher OS when they receive CB grafts with an HLA-C1/KIR2DL2/L3/S2 genotype. This protective effect was lost if the CB grafts were HLA-C1-KIR2DL2/L3-positive but lacked the activating KIR2DS2, or if they were unlicensed (HLA-C1-negative). All these results were validated in an independent cohort of patients. Conversely, patients homozygous for HLA-C2 had a superior outcome when transplanted with an HLA-C2/KIR2DL1/S1-positive CB graft. Of note, there was no impact of KIR-HLA genotype on TRM or the risk of acute or chronic GVHD.

It was also found that KIR2DS2 and KIR2DS1 positivity in the CB graft was associated with a lower relapse rate in specific cohorts of patients. The protective effect of KIR2DS2 was limited to patients with the HLA-C1/x genotype, while that of KIR2DS1 was limited to HLA-C2 homozygous patients. Notably, this protection was seen only in the presence of NK licensing, consistent with studies in both humans and murine models showing that unlicensed NK cells are hyporesponsive to activating stimuli, and that this hyporesponsiveness can only be partially reversed by the expression of an activating receptor. Indeed, it was shown that in HLA-C1/x recipients, the effector function of donor NK cells from HLA-C1-KIR2DL2/L3/S2-positive CB grafts is superior to that of NK cells that were either unlicensed (HLA-C1/x negative) or lacked KIR2DS2 (FIGS. 9 and 11). Thus, these observations emphasize the importance of the combination of NK licensing and activating KIRs, as opposed to only KIR-ligand mismatch or the presence of an activating MR per se, to alloreactivity in the post-CBT setting. Moreover, HLA class-I molecules may be downregulated on leukemic cells, creating a situation of de-facto KIR-ligand mismatch, irrespective of whether such a mismatch exists at the genotype level. In the absence of a KIR-ligand mismatch, NK cells are capable of killing leukemic blasts with low expression of HLA class-I molecules more efficiently than cells with high HLA class-I expression.

Example 4—Materials and Methods

Patients:

All patients who received a CBT under standardized protocols for the treatment of different hematologic malignancies were eligible for this analysis. HLA genotypes were provided by the HLA Typing Laboratory at MDACC. KIR genotyping was performed with the SSP MR genotyping kit (Invitrogen) as described previously (Marin et al., 2011), based on the availability of specimens and without preference for patients with particular clinical characteristics. For the discovery and validation studies, patients were selected sequentially, and no patient was included in both studies.

The discovery cohort included 110 patients who had undergone CBT between 2009 and 2012 and had available genomic DNA from both the recipient and the CB graft (Table 1A). The median follow-up for surviving patients at the time of analysis was 14 months (range, 2-64 months). An independent cohort of 94 consecutive patients who received CBT between 2005 and 2009 and had features similar to those of the study group (Table 1B) was used to validate the results. This study was performed in accord with the Declaration of Helsinki following informed consent and was approved by the local institutional review board (IRB).

Cord unit dominance, achieved by most patients, was defined as the unit with >90% chimerism in the total DNA fraction at the time the assay was performed.

In vitro NK Differentiation from CD34+ CB-Derived Progenitor Cells:

CB units for research were provided by the MDACC Blood Bank under a protocol approved by the IRB. CB mononuclear cells were isolated by density-gradient technique (Ficoll-Histopaque), and CD34+ progenitor cells were selected with the CD34 Progenitor Cell Isolation kit (Miltenyi Biotec). CD34+ purity was confirmed by flow cytometry and was consistently >98%. Isolated $CD34^+$ cells ($5\times10^4$) were cultured in 0.1 mL serum-free media (CellGro) supplemented with 100 U/ml penicillin/streptomycin and 10% FBS, recombinant human SCF (30 ng/ml), Flt3-L (50 ng/ml), IL-15 (50 ng/ml) and IGF-1 (100 ng/ml) in 96-well culture plates at 37° C. in a humidified atmosphere with 5% CO2 for 4 weeks. The culture medium was renewed with cytokines every other day, and MR protein expression was monitored by flow cytometry for 4 weeks with use of anti-CD56-BV605 (clone HCD56), anti-CD3-PECy5 (clone UCHT1), anti-KIR3DL1-AlexaFluor700 (clone DX9; Biolegend), anti-KIR2DL1-APC (clone REA284), anti-KIR2DL3-Biotin (clone REA147 with streptavidin-APC-Cy7; Miltenyi Biotec), anti-NKG2A-PECy7 (clone Z199) and anti-KIR2DL2/L3/S2-PECy5.5 (clone GL183; Beckman Coulter).

NK Cell Phenotyping and Functional Assays:

NK cell cytotoxicity and cytokine production were assessed by preincubating peripheral blood mononuclear cells (PBMCs) either alone (negative control) or with target K562 cells (E:T ratio of 10:1) for 5 hours at 37° C. in the presence of anti-CD107a-PECF594 (clone H4A3), GolgiStop/monensin (both from BD Biosciences) and Brefeldin A (Sigma-Aldrich). PMA/ionomycin stimulation was used as a positive control. After coculture, cells were stained with a live/dead aqua viability marker (Life technologies), anti-CD56-BV605 (clone HCD56), anti-CD3-PECy5 (clone UCHT1), anti-CD16-BV650 (clone 3G8), anti-NKG2A-PECy7 (clone Z199; Beckman Coulter), and with mAbs against activating and inhibitory MR receptors, including anti-KIR2DL1-APC (clone REA284), anti-KIR2DL3-Biotin (clone REA147, combined with streptavidin-APC-Cy7) (Miltenyi Biotec), anti-KIR2DL1/2DS1-PE (clone EB6), anti-KIR2DL2/S2/L3-PECy5.5 (clone GL183), anti-KIR3DL1/DS1 (clone Z27.3.7), anti-KIR3DL1-AlexaFluor700 (clone DX9, Biolegend). Cells were then fixed and permeabilized with FACS lysing and permeablizing solution (both from BD Biosciences). Cytokine production was measured by intracellular staining with anti-IFNγ-V450 (clone B27; BD Biosceinces) and anti-TNFα-PerCPCy5.5

(clone MAB11; Biolegend). All flow cytometry data were acquired on an LSRFortessa (BD Biosciences) and analyzed on Flowjo software (Treestar).

Phenotyping of AML Blasts:

The expression of HLA class I on the surface of AML blasts and normal myeloid cells was assessed with use of anti-CD33-PE-Cy7 (clone P67.6; BD), anti-CD34-PerCP (clone 8G12; BD), anti-CD13-PE (clone WM15; BioLegend) and anti-HLA-ABC-APC (clone G46-2.6; Pharmingen).

Target Cells and Culture Conditions:

K562 cells were cultured in RPMI 1640 medium supplemented with 10% heat-inactivated FBS, 1% penicillin, streptomycin and L-glutamine, and incubated at 37° C. with 5% $CO_2$.

Statistical Methods:

The probability of overall survival (OS) was calculated by the Kaplan-Meier method. The probabilities of disease relapse and transplant related mortality (TRM) were calculated by the cumulative incidence procedure. For disease relapse, relapse was considered the event of interest and death prior to relapse the competitor. For TRM, death not caused by disease relapse was considered the event of interest and death caused by the malignancy the competitor. Univariate analysis was performed with standard statistical methodology. Variables found to be significant at the p<0.10 level were included in the multivariate analysis, where OS was examined with a Cox regression model and relapse by Fine-Gray regression analysis. Categorical data were compared with Fisher's exact test, and quantitative data with the Mann-Whitney or the Kruskal-Wallis test. Hazard ratios (HR) are reported with 95% confidence intervals (CI). All p-values are two-sided.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,225,042
U.S. Pat. No. 6,355,479
U.S. Pat. No. 6,362,001
U.S. Pat. No. 6,410,319
U.S. Pat. No. 6,489,458
U.S. Pat. No. 6,790,662
U.S. Pat. No. 7,109,304
U.S. Patent Application Publication No. 2009/0004142
U.S. Patent Application Publication No. 2009/0017000
PCT Publication No. WO2007/103009
Anfossi et al., *Immunity*, 25: 331-42, 2006.
Campbell et al., *Immunology*, 132: 315-325, 2011.
Campbell, *Curr. Top. Microbiol. Immunol.*, 298: 23-57, 2006.
Denman et al., *PLoS One*, 7: e30264, 2012.
Fernandez et al., *Blood*, 105: 4416-4423, 2005.
Gabriel et al., *Blood*, 116: 2033-2039/
Giebel et al., *Blood*, 102: 814-819, 2003.
Herberman, *Ann. Rev. Med.*, 37: 347-52, 1986.
Houtchens et al., *Immunogenetics*, 59: 525-537, 2007.
Khouri et al., *Exp. Hematol.*, 32: 28-35, 2004.
Kim et al., *Nature*, 436:709-713, 2005.
Kulkarni et al., *Methods Mol. Biol.*, 612: 365-375, 2010.
Ljunggren et al., *Immunol. Today*, 11: 237-44, 1990.
Marin et al., *Leukemia*, 2011.
Marin et al., *Leukemia*, 2011.
Marsh et al., *Immunogenetics*, 55: 220-6, 2003.
Navarro et al., *Front Immunol.*, 6, 2015.
Rocha et al., *N Engl. J. Med.*, 351: 2276-2285, 2004.
Ruggeri et al., *Science*, 295: 2097-2100, 2002.
Saliba et al., *Biol. Blood Marrow Transplant*, 21:1284-1290, 2015.
Shah et al., *PLoS One*, 8:e776781, 2013.
Singh et al., *Cancer Research*, 68:2961-2971, 2008.
Singh et al., *Cancer Research*, 71:3516-3527, 2011.
Singh et al., *PLoS One*, 8:e64138, 2013.
Venstrom et al., *N. Engl. J. Med.*, 367: 805-816, 2012.
Vilches et al., *Annu. Rev. Immunol.*, 20: 217-51, 2002.
Wu et al., *Adv. Cancer Res.*, 90: 127-56, 2003.

What is claimed is:

1. A method of treating a disease or disorder in a subject in need thereof comprising administering to the subject a therapeutically effective amount of natural killer (NK) cells, wherein
   (a) the subject has been determined to have an HLA-C genotype either homozygous or heterozygous for the C1 allele and the NK cells express HLA-C1-licensed KIR2DL2/3 and KIR2DS2; or
   (b) the subject has been determined to have an HLA-C genotype that is homozygous for the C2 allele and the NK cells express HLA-C2-licensed KIR2DL1 and KIR2DS1, wherein the disease or disorder is acute lymphoblastic leukemia (ALL), acute myelogenous leukemia (AML), or myelodysplastic syndrome (MDS) and the subject is a human.

2. The method of claim 1, wherein the subject has been determined to have an HLA-C genotype either homozygous or heterozygous for the C1 allele and the NK cells express HLA-C1-licensed KIR2DL2/3 and KIR2DS2.

3. The method of claim 1, wherein the subject has been determined to have an HLA-C genotype that is homozygous for the C2 allele and the NK cells express HLA-C2-licensed KIR2DL1 and KIR2DS1.

4. The method of claim 1, wherein the NK cells are derived from umbilical cord blood (CB) or peripheral blood.

5. The method of claim 1, wherein the NK cells are genetically modified to express interleukin-15 (IL-15).

6. The method of claim 1, wherein the NK cells are genetically modified to express a recombinant chimeric antigen receptor (CAR) comprising an intracellular signaling domain, a transmembrane domain, and an extracellular domain comprising an antigen binding region.

7. The method of claim 6, wherein the antigen binding region is an F(ab')2, Fab', Fab, Fv, or scFv.

8. The method of claim 6, wherein the intracellular signaling domain comprises CD3ξ, CD28, OX40/CD134, 4-1BB/CD137, FcεRIγ, ICOS/CD278, ILRB/CD122, IL-2RG/CD132, DAP molecules, CD70, cytokine receptor, CD40, or a combination thereof.

9. The method of claim 6, wherein the transmembrane domain comprises CD28 transmembrane domain, IgG4Fc hinge, Fc regions, CD4 transmembrane domain, the CD3ξ transmembrane domain, cysteine mutated human CD3ξ domain, CD16 transmembrane domain, CD8 transmembrane domain, or erythropoietin receptor transmembrane domain.

10. The method of claim 1, wherein NK cells are genetically modified to express an inducible suicide gene.

11. The method of claim 10, wherein the suicide gene is caspase 9.

12. The method of claim 10, further comprising administering AP20187 to the subject to induce apoptosis of the NK cells.

13. The method of claim 1, further comprising administering a second therapeutic agent.

14. The method of claim 13, wherein the second therapeutic agent comprises T cells, an immunomodulatory agent, a monoclonal antibody, or a chemotherapeutic agent.

15. The method of claim 14, wherein the immunomodulatory agent is lenalidomide.

16. The method of claim 14, wherein the monoclonal antibody is rituximab, ofatumumab, or lumiliximab.

17. The method of claim 14, wherein the chemotherapeutic agent is fludarabine or cyclophosphamide.

18. The method of claim 1, wherein the disease or disorder is acute lymphoblastic leukemia (ALL) or acute myelogenous leukemia (AML).

* * * * *